United States Patent
Kotecha et al.

(10) Patent No.: US 12,037,574 B2
(45) Date of Patent: Jul. 16, 2024

(54) CELL VIABILITY APPARATUS, SYSTEM, AND METHODS THEREOF

(71) Applicant: O2M Technologies, LLC, Chicago, IL (US)

(72) Inventors: Mrignayani Kotecha, Chicago, IL (US); Boris Meerovich Epel, Chicago, IL (US); Eliyas Siddiqui, Chicago, IL (US); Safa Hameed, Chicago, IL (US)

(73) Assignee: O2M Technologies, LLC, Chicago, IL (US)

( * ) Notice: Subject to any disclaimer, the term of this patent is extended or adjusted under 35 U.S.C. 154(b) by 0 days.

(21) Appl. No.: 18/506,801

(22) Filed: Nov. 10, 2023

(65) Prior Publication Data
US 2024/0158733 A1 May 16, 2024

Related U.S. Application Data

(60) Provisional application No. 63/429,402, filed on Dec. 1, 2022, provisional application No. 63/425,187, filed on Nov. 14, 2022.

(51) Int. Cl.
*C12M 1/34* (2006.01)
*C12M 1/00* (2006.01)

(52) U.S. Cl.
CPC ........... *C12M 41/46* (2013.01); *C12M 29/24* (2013.01); *C12M 41/12* (2013.01)

(58) Field of Classification Search
None
See application file for complete search history.

(56) References Cited

U.S. PATENT DOCUMENTS

2003/0170912 A1* 9/2003 Muravsky ............. G01R 33/60
702/19
2020/0309888 A1* 10/2020 Daly ..................... G01R 33/60

OTHER PUBLICATIONS

Kotecha et al., Noninvasive Absolute Electron Paramagnetic Resonance Oxygen Imaging for the Assessment of Tissue Graft Oxygenation, 2018, Tissue Engineering: Part C, vol. 24 No. 1 (Year: 2018).*

Koto et al., Detection and identification of oxidants formed during â¢NO/O2â¢â» reaction: a multi-well plate CW-EPR spectroscopy combined with HPLC analyses, 2014, Free Radical Research, 48(4) (Year: 2014).*

* cited by examiner

*Primary Examiner* — Holly Kipouros
(74) *Attorney, Agent, or Firm* — Schwegman Lundberg & Woessner, P.A.

(57) ABSTRACT

A method includes placing a sample of cells, tissue, or an organ into an oxygen imaging system, circulating a humidified gas mixture around the tissue or organ, circulating conditioned air through the oxygen imaging system to maintain a temperature around the sample, and acquiring a three-dimensional oxygen map of the sample. The oxygen map provides a quantitative measure of cell viability and functionality.

16 Claims, 51 Drawing Sheets
(48 of 51 Drawing Sheet(s) Filed in Color)

Cell viability after 4 hours using MTT assay

Cell morphology after 4 hours of imaging

CELL VIABILITY APPARATUS, SYSTEM, AND METHODS THEREOF

CLAIM OF PRIORITY

This patent application claims the benefit of priority of U.S. Provisional Patent Application Ser. No. 63/425,187, filed on Nov. 14, 2022 and claims the benefit of priority of U.S. Provisional Patent Application Ser. No. 63/429,402, filed on Dec. 1, 2022, each of which is hereby incorporated by reference herein in their entirety.

STATEMENT REGARDING FEDERALLY SPONSORED RESEARCH OR DEVELOPMENT

This invention was made with government support under 2028829 awarded by National Science Foundation. The government has certain rights in the invention.

FIELD

The present disclosure relates generally to a system and method for non-destructively assessing in situ cell viability. In at least one example, the present disclosure relates to a system and method for non-destructively assessing in situ cell viability using oxygen imaging.

BACKGROUND

Cell viability is an essential parameter for cell therapy, tissue engineering, drug screening, and many other biological processes and products. These products rely on viable, healthy, and functional cells to work as intended for solving various medical conditions, such as cancer, type I diabetes, arthritis, liver, kidney, bone damage, neurodegenerative, cardiovascular damage, etc. However, current methods that rely on assays to measure cell viability are destructive and inadequate for three-dimensional tissues. Besides, these methods do not assess cell functionality, a key parameter for cell therapy and tissue engineering medical products. In addition, these methods have not been tested for their interference with biomaterials commonly used in the field, therefore, may provide an inaccurate assessment when used with artificial tissue grafts involving scaffolds.

Electron paramagnetic resonance oxygen imaging (EPROI) is a noninvasive oxygen mapping method with high precision and absolute accuracy. Similar to nuclear magnetic resonance imaging (MM), EPROI uses magnetic field gradients to generate the spatial distribution of electron spins. In contrast to conventional MRI, EPROI relies on a much smaller magnetic field (in the milli Tesla range), generated by cryogen-free magnets and gradients that do not change during signal detection. EPROI uses the linear relationship between electron spin-lattice relaxation rate and partial oxygen pressure (pO2) of an injectable non-toxic soluble contrast agent, trityl OX071, for obtaining oxygen maps in tissues.

SUMMARY

The present inventors have recognized, among other things, that a problem to be solved can include determining cell viability.

The present subject matter can help provide a solution to this problem, such as by assessing cell viability nondestructively using oxygen imaging, such as EPROI.

Each of the non-limiting examples provided herein can stand on its own, or can be combined in various permutations or combinations with one or more of the other examples.

This overview is intended to provide an overview of subject matter of the present patent application. It is not intended to provide an exclusive or exhaustive explanation of the invention. The detailed description is included to provide further information about the present subject matter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
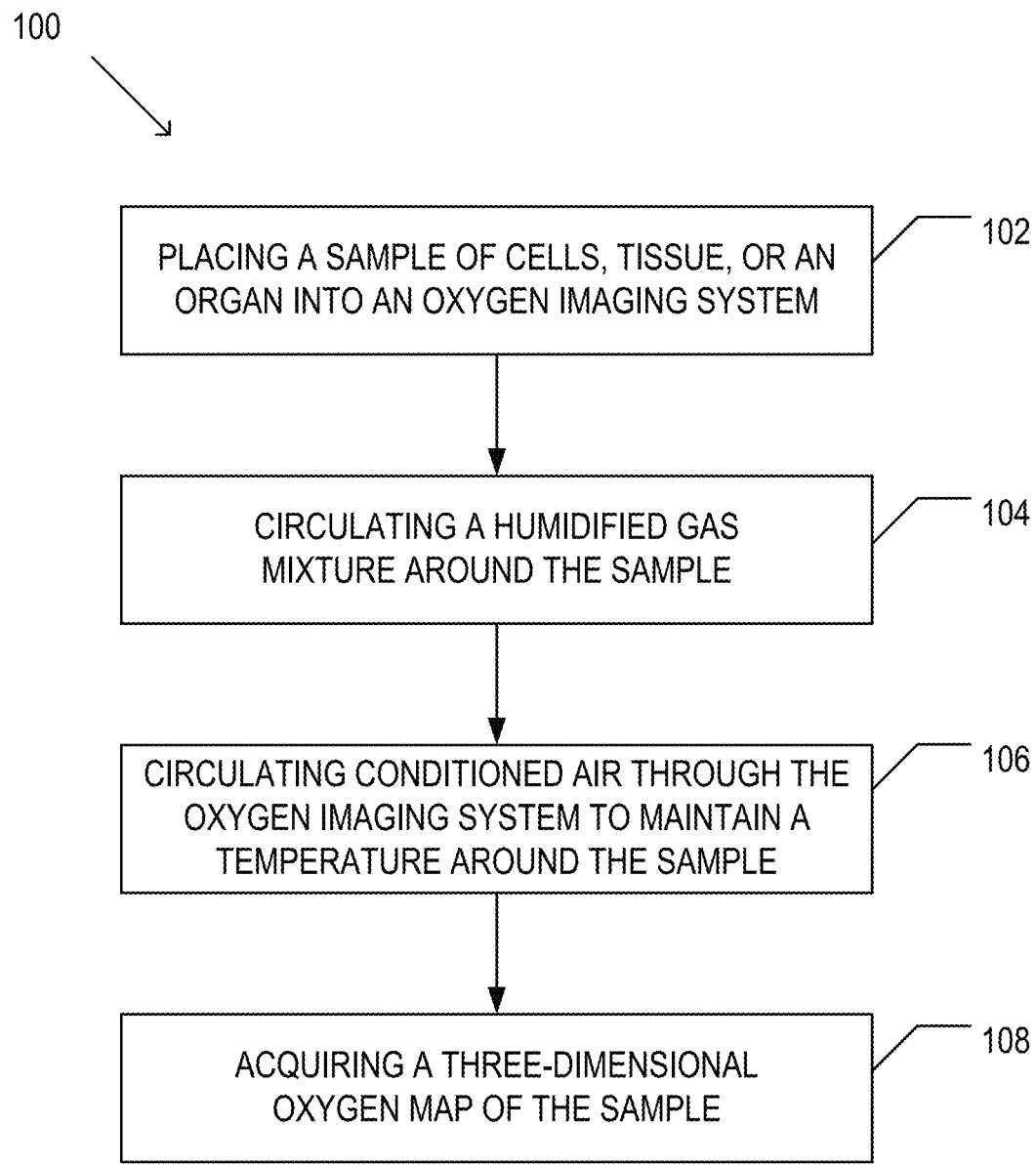
FIG. 1 is an example flowchart of the method for non-destructively assessing in situ cell viability.

It will be appreciated that for simplicity and clarity of illustration, where appropriate, reference numerals have been repeated among the different figures to indicate corresponding or analogous elements. In addition, numerous specific details are set forth in order to provide a thorough understanding of the examples described herein. However, it will be understood by those of ordinary skill in the art that the examples described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

Several definitions that apply throughout the above disclosure will now be presented. The terms "connected" or "coupled" is defined as connected, whether directly or indirectly through intervening components, and is not necessarily limited to physical connections. The connection may be such that the objects are permanently connected, releasably connected, or wirelessly connected.

Reference to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Thus, references to one or an embodiment in the present disclosure may be references to the same embodiment or any embodiment; and such references mean at least one of the embodiments.

The terms "comprising," "including" and "having" are used interchangeably in this disclosure. The terms "comprising," "including" and "having" mean to include, but not necessarily be limited to the things so described.

As used herein, "about" refers to numeric values, including whole numbers, fractions, percentages, etc., whether or not explicitly indicated. The term "about" generally refers to a range of numerical values, for instance, ±0.5-1%, ±1-5% or ±5-10% of the recited value, that one would consider equivalent to the recited value, for example, having the same function or result.

As used herein, "imaging system" and "resonator" may be used interchangeably. In an aspect, the imaging system may be an oxygen imaging system that comprises a resonator such as magnetic resonance imaging (MM), positron emission tomography (PET), computed tomography (CT), eMRI, or pulse electron paramagnetic resonance oxygen imaging (EPROI) imaging systems. For example, the imaging system may be configured for EPROI.

The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any example term.

Cell viability is an essential parameter for cell therapy, tissue engineering, drug screening, and many other biological processes and products. These products rely on viable, healthy, and functional cells to work as intended for solving various medical conditions, such as cancer, type I diabetes, arthritis, liver, kidney, bone damage, neurodegenerative, cardiovascular damage, etc. Live and dead cell counts are used to evaluate cell growth, health, and function, as well as to establish cellular therapeutic product dose. A viable and functional cell is a cell with an intact membrane and/or the capacity for metabolism, proliferation, motility (migration), and/or reaction to stimuli. However, current methods that rely on assays to measure cell viability are destructive and inadequate for three-dimensional tissues. Besides, these methods do not assess cell functionality, a key parameter for cell therapy and tissue engineering medical products. In addition, these methods have not been tested for their interference with biomaterials commonly used in the field, therefore, may provide an inaccurate assessment when used with artificial tissue grafts involving scaffolds.

During current cell viability assays (e.g. Luciferase ATP assay, Picogreen DNA assay, or MTT assay), cells are typically destroyed to allow for staining and/or sectioning. In addition, current assays required cells/tissue to be removed from an environment that promotes growth (e.g. the body or an incubator). The destruction of the cells or tissue to be assessed prevents an adequate measure of cell functionality or viability, particularly in three dimensions. For example, current methods of assessing cell viability are invasive and destructive and do not provide a correct estimate for cells seeded in biomaterials. In addition, the provide arbitrary intensity values, pixel intensity may vary arbitrarily between instrumentations, intracellular uptake of a reagent may affect the results, dead cells may have different uptake of reagents, heterogeneity of typically cell-tissue construct is lost, and viable cells may not be functional. To currently measure cell viability in a scaffold and cell system, the tissue construct is destroyed by removing the scaffold material (which removes any spatial information). It is also possible that the biomaterials of the scaffold may interfere with current cell viability assays.

All these problems require a system that can identify cell viability without destroying cells, tissue, or scaffold/construct to better assess cell viability in a three-dimensional (3D) system without destroying the cells or scaffold. The system and method disclosed herein overcome these problems using oxygen imaging, such as EPROI. The cell viability system and method can be extended to perform cell viability and functionality assessment for all tissue engineering medical products of any size and dimensions. For example, the cell viability system is non-destructive, provides spatial information on cell viability, is calibrated with biomaterials, provides a direct measurement of viable cells in terms of a known unit, and has the ability for a large penetration depth to be able to observe cells at various depths in tissues and organs.

Cell viability experiments are crucial for understanding biology, designing new therapies, defining new strategies in cancer and regenerative medicine. Oxygen is a key physiological parameter. Hypoxia or low oxygen is a key biomarker of most cancers and cancer response to the therapy is dependent on oxygenation status. Hypoxia is also the major limiting factor in the success of cell therapies and artificial tissue grafts. Viable cells metabolize oxygen and therefore by performing oxygen imaging as a function of time, one can assess the viability of cells. EPROI provides non-invasive oxygen imaging in the tissues and systems. The system disclosed herein images cells viability while maintaining a controlled environment (temp, pH and humidity) for cells in order to assess its viability in 3D artificial grafts and biomaterials without destroying the samples.

EPROI is an imaging modality that provides partial oxygen pressure (pO2) maps with high temporal, spatial, and pO2 resolution. The pO2 maps obtained using EPROI are used for important insights into oxygen dynamics with applications in cancer, type I diabetes, arthritis, liver, kidney, bone damage, neurodegenerative, cardiovascular damage, tissue engineering and regenerative medicine. In recent studies, pO2 maps were used for assistance in oxygen guided radiation therapy (OGRT), assessment of islet encapsulation devices, assessment of anti-cancer drug, detection of mitochondrial dysfunction, and assessment of musculoskeletal tissue grafts. EPROI in combination with the cell viability system described herein below may be used for nondestructive cell viability assessment.

In EPROI, the $R_1$ relaxation rate of an oxygen-sensitive spin probe (e.g. trityl OX071) is measured using electron spin echo inversion recovery sequence. The oxygen-sensitive spin probe is non-toxic to cells and animals and remains in the extra-cellular space. The measurement range is about 0-160 torr (0%-21% $O_2$). In an example, 160 torr is about 0.0094 moles of $O_2$.

Further described herein is how the noninvasive cell viability assessment can be performed on a three-dimensional system without destroying the cells or scaffold. The method can be extended to perform cell viability and functionality assessment for all tissue engineering medical products of any size and dimensions.

Methods of Assessing Cell Viability

Further provided herein are methods for non-destructively assessing in situ cell viability. A flowchart as seen in FIG. 1 is presented in accordance with an example embodiment. The method 100 is provided by way of example, as there are a variety of ways to carry out the method. The method 100 described below can be carried out using the configurations illustrated in the figures, for example, and various elements of these figures are referenced in explaining example method 100. Each block represents one or more processes, methods or subroutines, carried out in the example method 100. Furthermore, the illustrated order of blocks in FIG. 1 is illustrative only and the order of the blocks can change according to the present disclosure. Additional blocks may be added or fewer blocks may be utilized, without departing from this disclosure.

The example method 100 is a method for non-destructively assessing in situ cell viability. The example method 100 can begin at block 102. At block 102, the method includes placing a sample into an oxygen imaging system. The sample may include cells, tissue, or an organ. In some embodiments, the tissue or the organ to be assessed for viability is artificial. For example, the cells may be within a scaffold for tissue engineering. The scaffold may include any biocompatible material suitable for supporting cells. In some embodiments, the tissue or the organ to be assessed for viability is natural.

In some embodiments, the imaging system is an oxygen imaging system. In at least one example, the oxygen imaging system is an electron paramagnetic resonance oxygen imaging system. When imaging with an EPROI system, a non-toxic soluble contrast agent may be added to the sample. In an example, the contrast agent may be trityl OX071. In an example, the EPROI system may be a 25 mT preclinical EPROI instrument, which operates at 720 MHz radiofrequency. In additional examples, the EPROI system may provide absolute oxygen images with 1 mmHg oxygen resolution, have a 1-10 minute imaging time, have a spatial resolution of 0.25 mm×0.25 mm×0.25 mm for in vitro and 1 mm×1 mm×1 mm for in vivo, may image a sample size up to 40 mm for volume coils, and have a penetration depth of 6-8 cm.

In some embodiments, the oxygen imaging system may include a resonator having a body and an intake connector. The resonator body may be configured to circulate the conditioned air around the multi-well apparatus within the resonator body.

At block 104, the method includes circulating a humidified gas mixture around the sample. The humidified gas mixture may be circulated within the imaging system. In an embodiment, the humidified gas mixture is circulated within a resonator of an oxygen imaging system, such as an EPROI system.

In an embodiment, the humidified gas mixture comprises 95% air and 5% $CO_2$. The humidified gas mixture may come from a humidifier. In an example, a 95% air and 5% $CO_2$ gas mixture is passed through the humidifier at a low flow rate of about 3.75 sccm to 30 sccm. The humidified gas mixture may have a relative humidity of between about 30% and about 100%, about 30% to 50%, about 40% to 60% about 50% to 70%, about 60% to 80%, about 70% to 90%, about 80% to 100%, or about 70% to 100%. For example, relative humidity may be 100% at 30 sccm or 70% at 3.75 sccm. In some embodiments, the moisture content of the humidified gas mixture may be measured. The moisture content or relative humidity of the humidified gas mixture may be measured with a humidity sensor. For example, the humidified gas may then be delivered to cells via the cover, and relative humidity is recorded using a humidity and temperature sensor to ensure that cells are receiving about 70-100% relative humidity.

In some embodiments, the sample of cells, tissue, organ, and/or scaffold may be contained within an apparatus, such as a multi-well apparatus. In an embodiment, the multi-well apparatus may include a cover configured for circulating the humidified gas through each well. The cover seals the plurality of wells, such that the apparatus is a closed system.

In some embodiments, the method may further include receiving the humidified gas mixture in an inlet in the cover and exhausting the humidified gas mixture through an outlet in the cover. In an example, a plurality of channels connect the inlet, the plurality of wells, and the outlet. The plurality of channels may include at least one gas inlet channel and at least one gas outlet channel. In some examples, each well may be fluidly connected to a gas inlet channel and a gas outlet channel.

In some embodiments, the cover includes a plurality of manifolds configured to fluidly connect each well to a gas inlet channel and a gas outlet channel. In some examples, the number of wells matches the number of manifolds. Each manifold may include a groove configured to receive an O-ring to seal the manifold to the well and a gas exchange protrusion. In some examples, the gas exchange protrusion may include a well gas inlet fluidly connected to the gas inlet channel and a well gas outlet fluidly connected to the gas outlet channel. The gas exchange protrusion may extend into the well. In some examples, the well gas inlet extends further into the well than the well gas outlet.

At block 106, the method includes circulating conditioned air through the oxygen imaging system to maintain a temperature around the sample of cells, tissue, or organ. Prior to imaging, a target temperature and/or a target temperature range may be determined. The target temperature may be within the target temperature range. The target temperature range may be a standard temperature range for an incubator. In some embodiments the target temperature range may be about 37° C.±0.5° C. or 37° C.±1° C. In other embodiments, the target temperature range may be 32° C. to 40° C. In some embodiments, the target temperature may vary based upon several factors, such as the size of the tissue or organ or the type of cell.

In some embodiments, the moisture content of the conditioned air may be measured. The conditioned air flow may have a relative humidity of between about 30% and about 100% or between about 30% and 50%. The moisture content or relative humidity of the conditioned air flow may be measured with a humidity sensor.

The combination of the humidified gas mixture and the conditioned air provides an environment within the imaging system similar to that of an incubator, allowing cells, tissues, and organs of the sample to be imaged in situ without destroying the cells. In an embodiment, at least 80%, 85%, 90%, 95%, or 99% of cells alive at the beginning of the assessment survive the in situ cell viability assessment.

In some embodiments, the method may further include mixing two air flows in a mixing area of a heating interface to produce the conditioned air. The heating interface may be configured to connect to the resonator body via the intake connector.

At block 108, the method further includes acquiring a three-dimensional oxygen map of the cells, tissue, or organ of the sample. The oxygen map provides a quantitative measure of cell viability and functionality. In some embodiments, the oxygen map is a $pO_2$ map that represents viable cells. For example, $pO_2$ values in the $pO_2$ map are higher for cells that are not viable than cells that are viable. In an embodiment, the oxygen map includes a color representation of cell viability.

In some embodiments, the method may further include characterizing different cell types in the cells, tissue, or organ of the sample. The different cell types have different equilibrium $pO_2$ values for a particular cell density. In an embodiment, the method may further include further comprising obtaining a signal amplitude map.

In some embodiments, the sample may include a cell and scaffold system. The scaffold may include a biocompatible material. For example, the sample may be a tissue engineered medical product. For each cell type, the cell and scaffold system has an equilibrium $pO_2$ for a certain cell density. When imaging cells in a scaffold system, the method may further include characterizing the cell density and assessing the cell viability without destroying the cell and scaffold system.

Cell Viability System

Provided herein is a cell viability system capable of imaging up to 24 wells and is able to maintain temperature, humidity, pH, and gas mixture to be an "incubator-like" system.

Figure 2A:
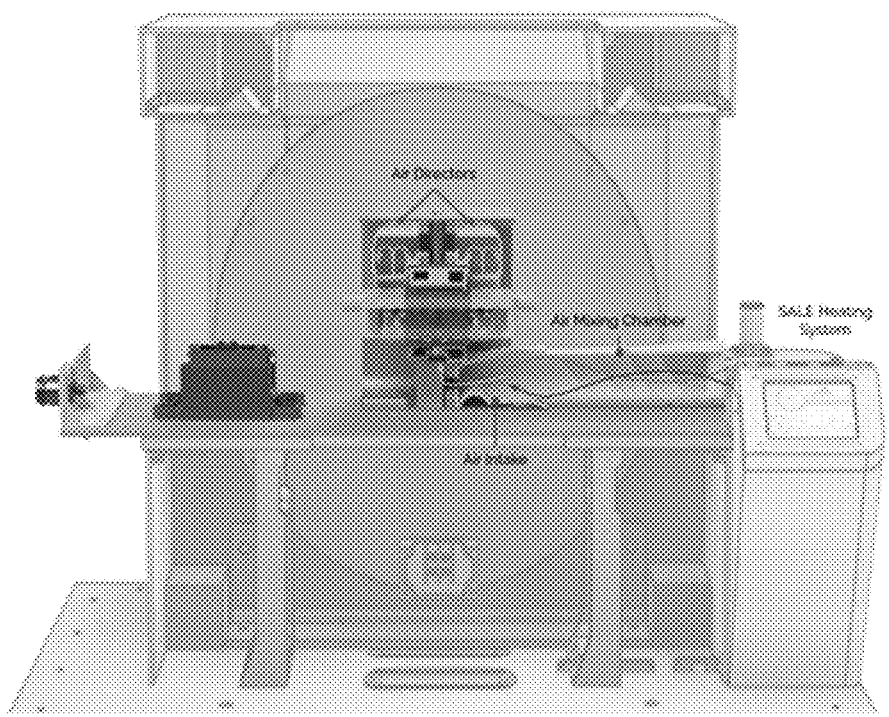
FIG. 2A is an example system for non-destructively assessing in situ cell viability.
Figure 2B:
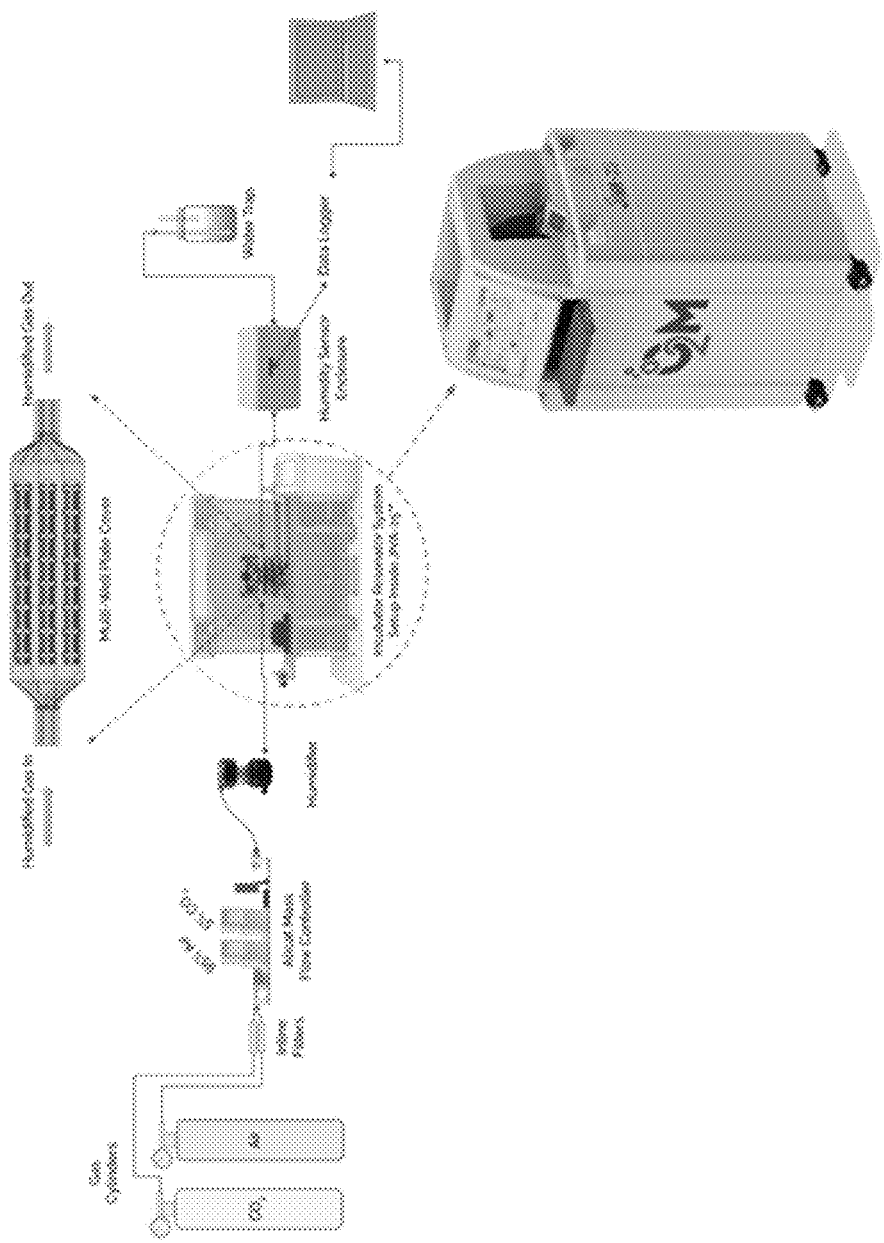
FIG. 2B is an example system for non-destructively assessing in situ cell viability with additional elements such as gas cylinders, inline filters, flow controllers, humidifier, humidity sensor, water trap, and data logger.
Figure 2C:
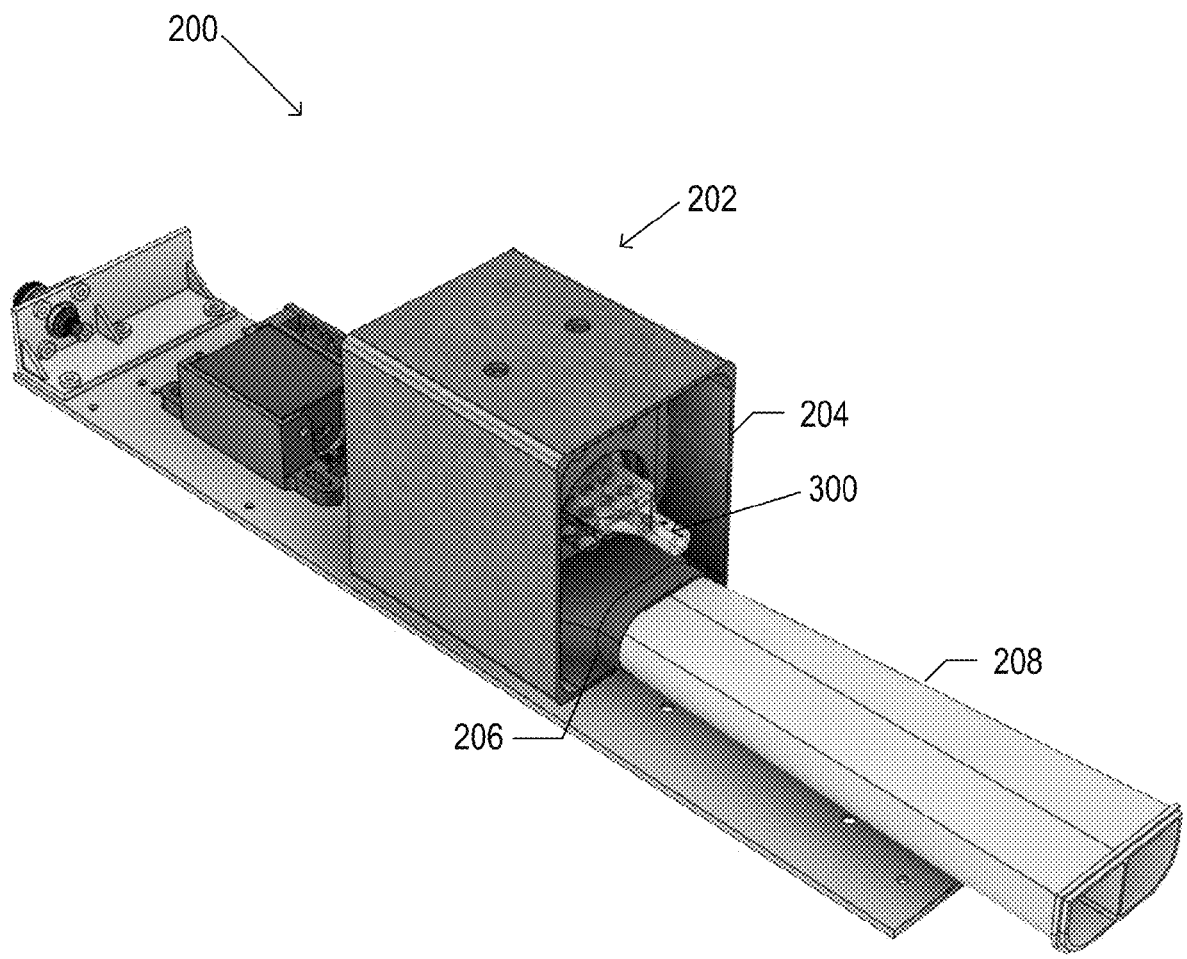
FIG. 2C is an example system for non-destructively assessing in situ cell viability.

In an embodiment, a system for non-destructively assessing in situ cell viability may include an oxygen imaging system or a portion of an oxygen imaging system. In some embodiments the oxygen imaging system comprises MRI, CT, PET, and/or EPROI. FIGS. 2A-2C shows an example system 200. FIG. 2A shows the cell viability system 200 within an EPROI imaging system. In some embodiments, the system includes a resonator assembly 202 for electron paramagnetic resonance oxygen imaging. In some embodiments, the resonator assembly 202 includes a body 204 and an intake connector 206. The resonator body 204 may be configured to circulate conditioned air around an apparatus within the resonator body 204, as seen in FIG. 2A. FIG. 2B shows an example system for non-destructively assessing in situ cell viability with additional elements such as gas cylinders, inline filters, flow controllers, humidifier, humidity sensor, water trap, and data logger. FIG. 2C shows a portion of the cell viability system 200.

Figure 3A:
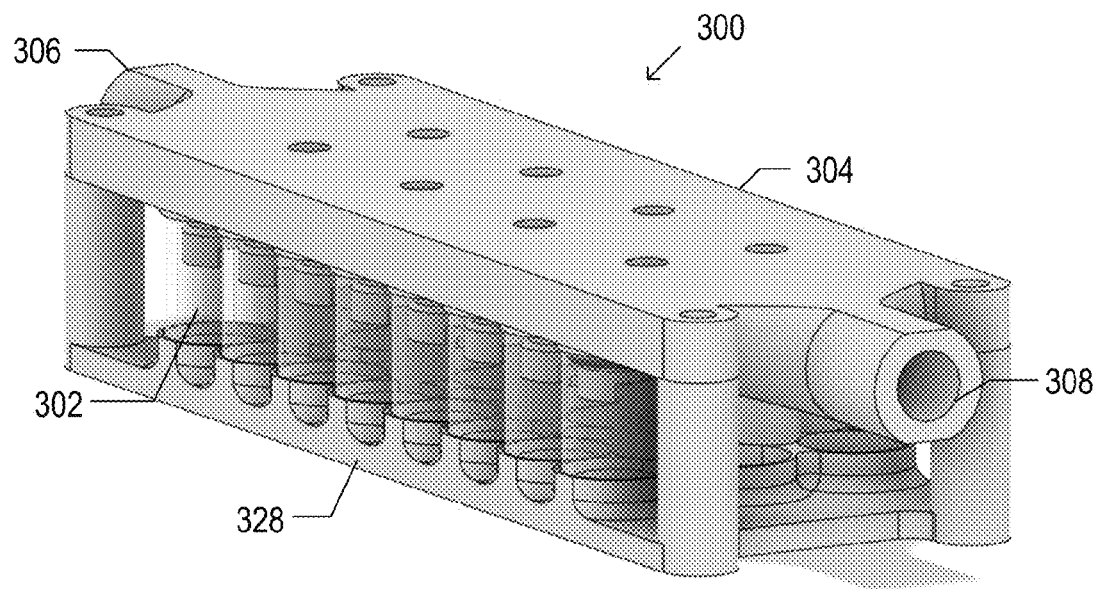
FIG. 3A is an example apparatus.

In an embodiment, the system 200 may further include an apparatus to hold a sample within the imaging system. In an example, the sample may include cells, tissue, an organ, and/or a three-dimensional scaffold. FIG. 3A shows an example apparatus. As shown in FIG. 3A, the apparatus may be a multi-well apparatus 300 having a plurality of wells 302 and a cover 304 configured to seal the plurality of wells 302. The multi-well apparatus 300 provides a humidified warm gas mixture to maintain the temperature, humidity, and pH around the sample. In some embodiments, the plurality of wells 302 are configured to hold the sample of cells, tissue, organ, and/or the three-dimensional scaffold. In an embodiment, the multi-well apparatus 300 is a closed system.

The apparatus is configured to circulate a humidified gas, such that any cells, tissue, or organ within the apparatus have access to the humidified gas. In an example, the cover 304 may be configured to circulate a humidified gas mixture through each well 302 to provide the humidified gas directly to the sample of cells, tissue, organ, and/or the three-dimensional scaffold within the wells. In an embodiment, the humidified gas mixture comprises 95% air and 5% $CO_2$. The humidified gas mixture may come from a humidifier. In an example, a 95% air and 5% $CO_2$ gas mixture is passed through the humidifier at a low flow rate of about 3.75 sccm. The humidified gas mixture may have a relative humidity of between about 30% and about 100%, about 30% to 50%, about 40% to 60% about 50% to 70%, about 60% to 80%, about 70% to 90%, about 80% to 100%, or about 70% to 100%. In at least one embodiment, the humidified gas mixture has a relative humidity of 70%-100%. In some embodiments, the moisture content of the humidified gas mixture may be measured. The moisture content or relative humidity of the humidified gas mixture may be measured with a humidity sensor. In an embodiment, the system 200 may further include a humidity sensor configured for measuring the relative humidity within the cover 304, resonator 228, or at any point within the system 200. For example, the humidified gas may be delivered to cells via the cover 304, and relative humidity is recorded using the humidity and temperature sensor to ensure that cells are receiving about 70-90% relative humidity.

Figure 3B:
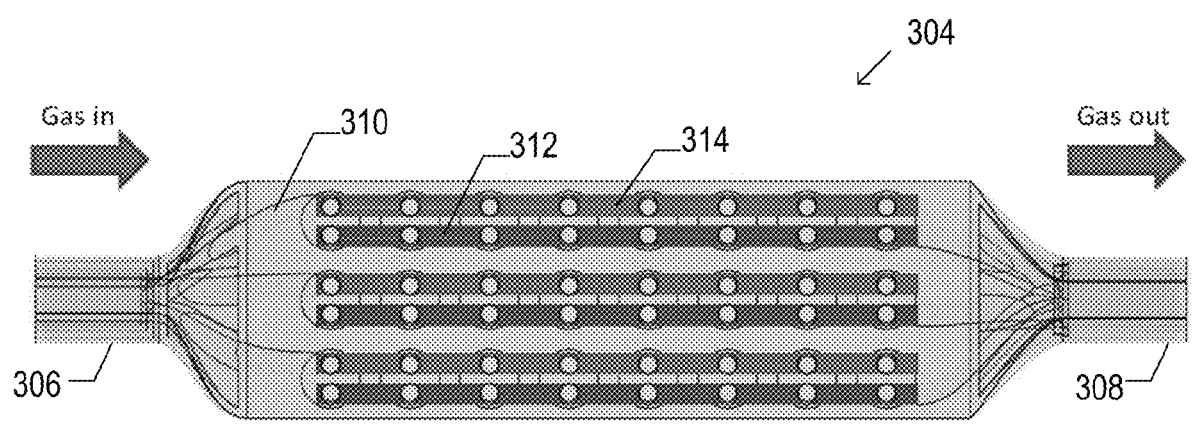
FIG. 3B is an example flow of humidified gas through the cover.
Figure 3C:
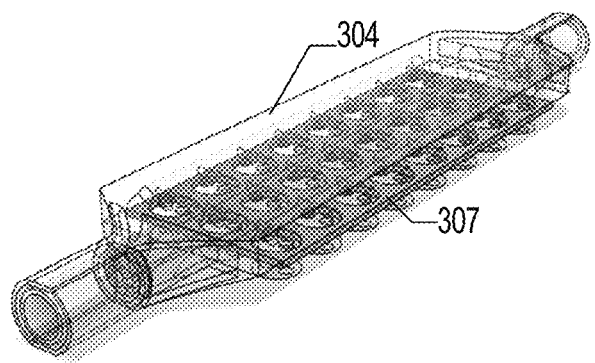
FIG. 3C is an example of a cover including a silicon gasket.

FIG. 3B shows an example flow of humidified gas through the cover 304. In some embodiments, as seen in FIGS. 3A-3C, a cover 304 of the apparatus is configured for circulating the humidified gas through the apparatus. In an embodiment, the cover 304 includes an inlet 306 for receiving the humidified gas mixture, an outlet 308 for exhausting the humidified gas mixture, and a plurality of channels 310 connecting the inlet 306, the plurality of wells 302, and the outlet 308. In some examples, as seen in FIG. 3C, the cover 304 may further include a silicone gasket 307. The plurality of channels 310 may include at least one gas inlet channel 312 and at least one gas outlet channel 314. Further, each well 302 may be fluidly connected to a gas inlet channel 312 and a gas outlet channel 314.

The length of the cover 304 may range from about 50 mm to 200 mm, 50 mm to 100 mm, 75 mm to 125 mm, 100 mm to 150 mm, 125 mm to 175 mm, 150 mm to 200 mm. In an example, the length of the cover 304 may be about 120 to 140 mm. For example, the length of the cover 304 may be about 130.5 mm. The width of the cover 304 may range from 10 mm to 100 mm, 10 mm to 30 mm, 20 mm to 40 mm, 30 mm to 50 mm, 40 mm to 60 mm, 50 mm to 70 mm, 60 mm to 80 mm, 70 mm to 90 mm, or 80 mm to 100 mm. In an example, the width of the cover 304 may be about 25 mm to 30 mm. For example, the cover 304 may have a width of about 27 mm. The height of the cover 304 may range from about 5 mm to 12 mm, 5 mm to 7 mm, 6 mm to 8 mm, 7 mm to 9 mm, 8 mm to 10 mm, 9 mm to 11 mm, or 10 mm to 12 mm. In an example, the height of the cover 304 may be about 9 mm.

The diameter of the inlet 306 and the outlet 308 may range from about 2 mm to 10 mm, 2 mm to 3 mm, 3 mm to 4 mm, 4 mm to 5 mm, 5 mm to 6 mm, 6 mm to 7 mm, 7 mm to 8 mm, 8 mm to 9 mm, 9 mm to 10 mm. In an example, the inlet 306 and the outlet 308 have a diameter of 6 mm. In some examples, the inlet 306 and the outlet 308 may be sized for a ¼-28 threaded luer lock.

Figure 3D:
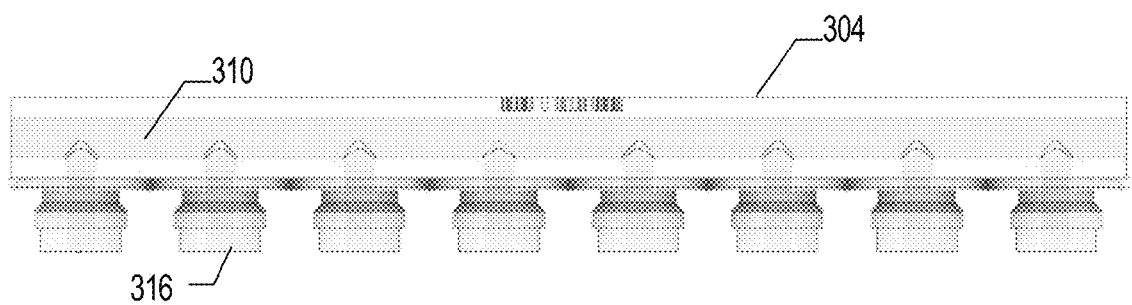
FIG. 3D is a sideview of an example cover.
Figure 3E:
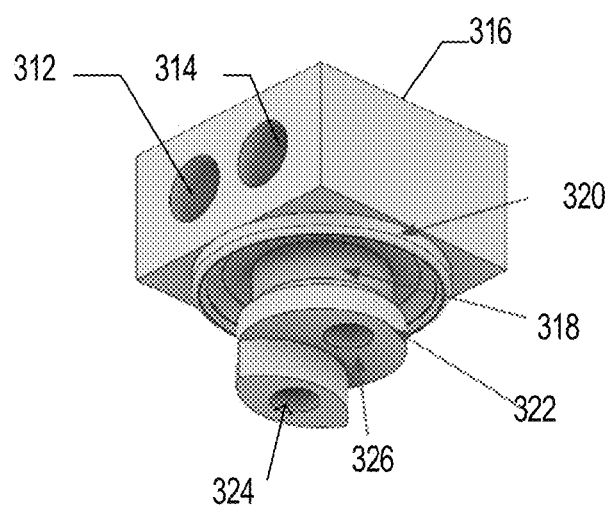
FIG. 3E is an example manifold that can be incorporated in the cover.
Figure 3F:
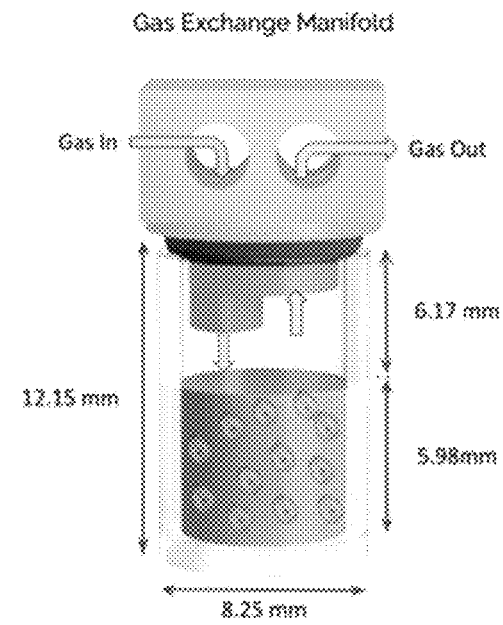
FIG. 3F, FIG. 3G, FIG. 3H, FIG. 3I, and FIG. 3J show example manifolds connected to a well filled with cells and media.
Figure 3G:
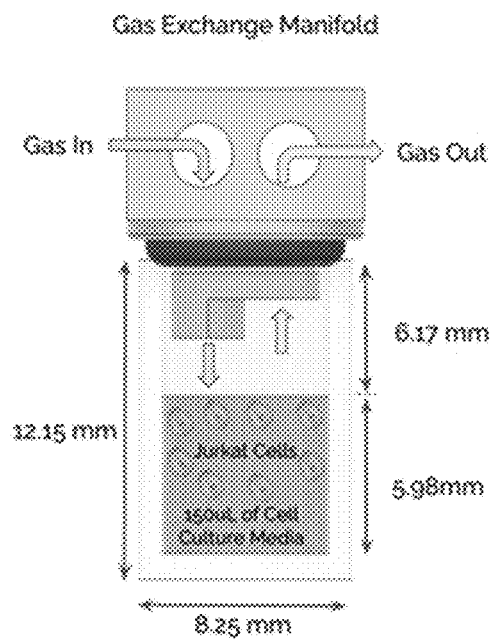
Figure 3H:
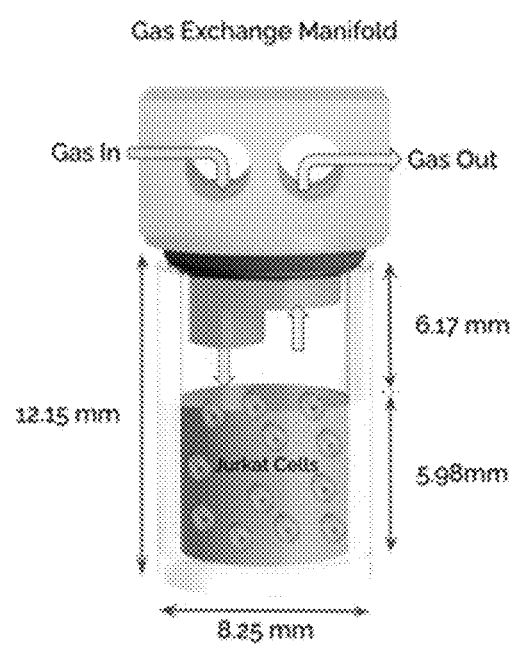
Figure 3I:
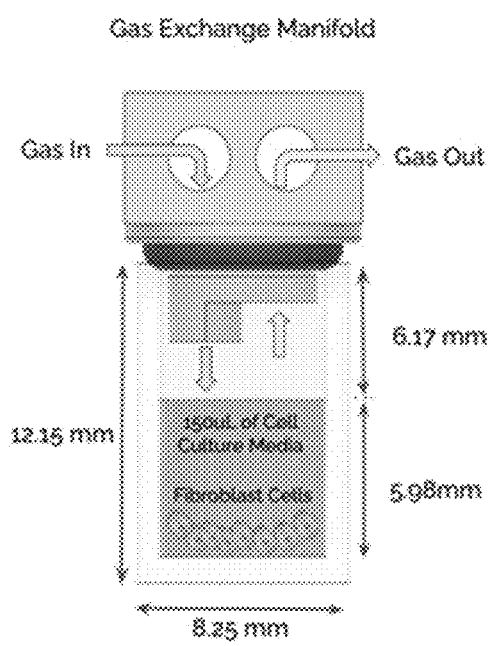
Figure 3J:
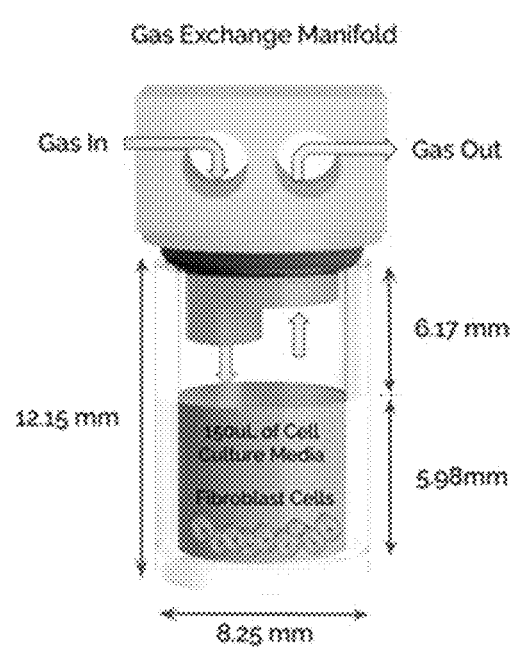

FIG. 3D is a side view of an example cover 304. In an embodiment, the cover 304 further includes a plurality of manifolds 316 configured to fluidly connect each well 302 to a gas inlet channel 312 and a gas outlet channel 314. FIG. 3E shows an example manifold 316 that may be incorporated in the cover 304. In some examples, the number of wells 302 matches the number of manifolds 316 so that each well 302 can be sealed and receive the humidified gas.

Each manifold 316 may include a gas exchange protrusion 322 comprising a well gas inlet 324 fluidly connected to the gas inlet channel 312 and a well gas outlet 326 fluidly connected to the gas outlet channel 314. In an embodiment, each gas exchange protrusion 322 extends to each well 302. In various examples, the outer diameter of the gas exchange protrusion 322 may range from about 3 mm to 10 mm, 2 mm to 4 mm, 3 mm to 5 mm, 4 mm to 6 mm, 5 mm to 7 mm, 6 mm to 8 mm, 7 mm to 9 mm, or 8 mm to 10 mm. For example, the outer diameter of the gas exchange protrusion 322 may be 3 mm, 4 mm, 5 mm, 6 mm, 7 mm, 8 mm, 9 mm, or 10 mm. In at least one example, the outer diameter of the gas exchange protrusion 322 is about 6 mm. In various examples, the height of the gas exchange protrusion 322 may range from about 1 mm to 8 mm, 1 mm to 3 mm, 2 mm to 4 mm, 3 mm to 5 mm, 4 mm to 6 mm, 5 mm to 7 mm, or 6 mm to 8 mm. For example, the height of the gas exchange protrusion 322 may be 3 mm.

The well gas inlet 324 may extend further than the well gas outlet 326 to prevent heterogenous gas mixture with the well gas outlet 326 and allow enough time for gas to interact with the sample. A similar concept can be used for square well plate or sample holder of another size/shape. In some examples, the well gas inlet 324 extends further into the well 302 than the well gas outlet 326. The well gas inlet 324 may extend 0.2 mm to 2 mm below the well gas outlet 326. For example, the well gas inlet 324 may extend, 0.2 mm to 0.5 mm, 0.5 mm to 1 mm, 1 mm to 1.5 mm, or 1.5 mm to 2 mm below the well gas outlet 326. In at least one example, the well gas inlet 324 extends 1.5 mm below the well gas outlet 326. Conversely, the well gas outlet 326 may be raised 1.5 mm above the well gas inlet 324.

Each manifold 316 may include a groove 318 configured to receive an O-ring (not shown) to seal each manifold 316 to each well 302. The groove 318 may be circumferentially surrounded by a ridge 320 to prevent shifting of the O-ring, manifold 316, and/or well 302. The groove 318 may be within the gas exchange protrusion 322, such that the groove 318 creates an area on the gas exchange protrusion 322 with a smaller diameter than the rest of the gas exchange protrusion 322. In various examples, the outer diameter of the gas exchange protrusion 322 at the groove 318 may be 2 mm to 6 mm, 2 mm to 3 mm, 3 mm to 4 mm, 4 mm to 5 mm, or 5 mm to 6 mm. In at least one example, the outer diameter of the gas exchange protrusion 322 at the groove 318 is about 5 mm.

FIG. 3F, FIG. 3G, FIG. 3H, FIG. 3I, and FIG. 3J show example manifolds connected to a well filled with cells and media.

Figure 3K:
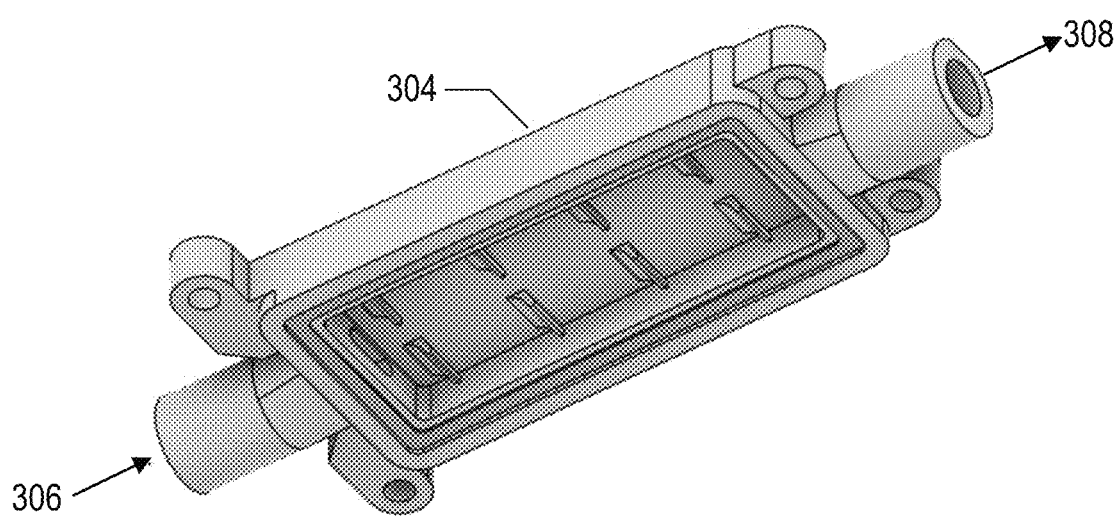
FIG. 3K is an example rectangular or square chamber of a cover for sealing a square well plate and circulating humidified gas through the square well plate.

In other embodiments, the cover 304 may include a single chamber 323 configured to pass the humidified gas from the inlet 306 through a single well 302 or container to an outlet 308. FIG. 3K shows an example rectangular or square chamber 323 of a cover 304 for sealing a square well plate (not shown) and circulating humidified gas through the square well plate.

Figure 4A:
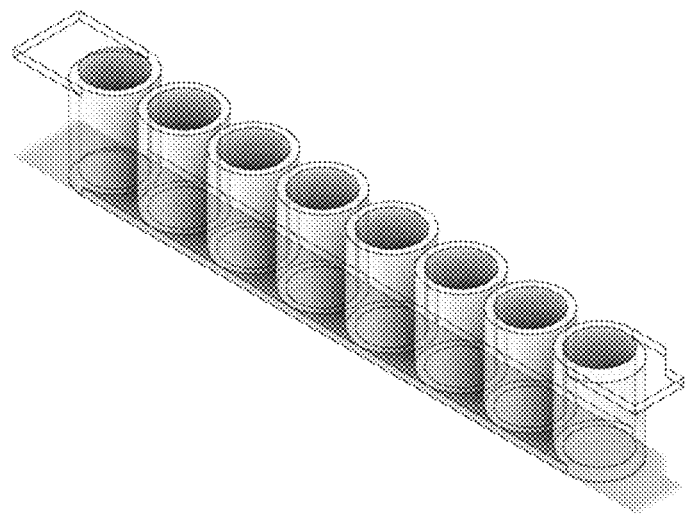
FIG. 4A is an example single row of 8 wells.
Figure 4B:
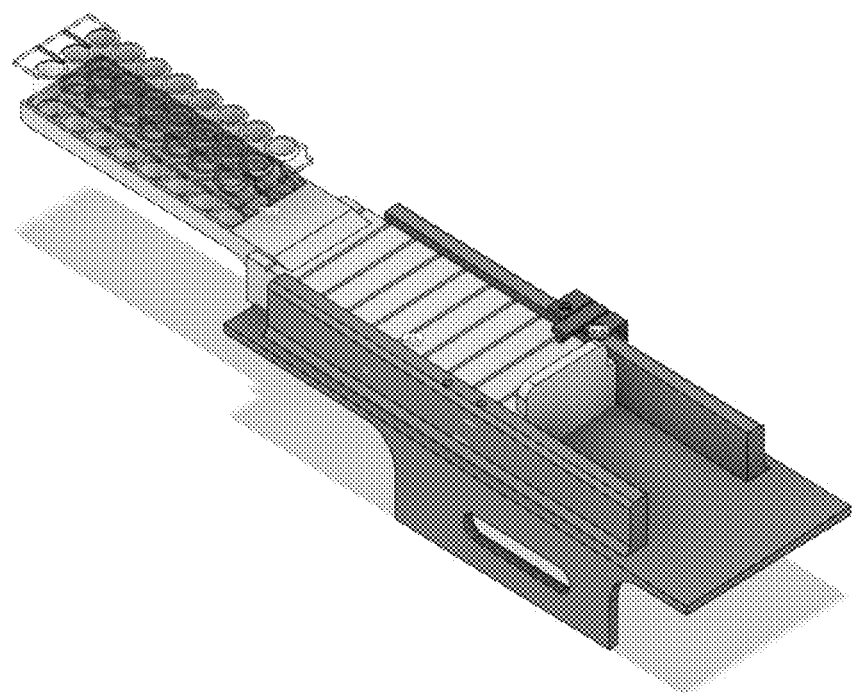
FIG. 4B is an example of three rows of 8 wells in a tray on a table.

The apparatus may include 1, 2, 3, 4, or 5 gas inlet channels 312 and gas outlet channels 314. In some embodiments, the apparatus may include 1 to 96 wells 302 to contain the sample of cells, tissue, or organs to be assessed for viability. A multi-well apparatus 300 may include 1, 2, 3, 4, 5, 6, 7, or 8 rows of wells 302. Each row may include 1, 2, 3, 4, 5, 6, 7, 8, 9, 10, 11, or 12 wells 302. The wells 302 of the multi-well apparatus 300 may be any type of well used to contain a sample of cells, tissues, or organs. In some examples, the wells 302 are wells of a 96-well plate, Greiner wells, or strip-wells such as 8 strip-wells or 12 strip-wells. FIG. 4A shows an example single row of 8 wells 302. FIG. 4B shows an example of three rows of 8 wells 302 in a tray 328 on a table.

The wells 302 may be sized to hold the sample. FIGS. 3F-3J show example manifolds connected to a well filled with cells and about 150 µL of cell culture media. The wells 302 may have a diameter ranging from about 2 mm to 10 mm, 2 mm to 3 mm, 3 mm to 4 mm, 4 mm to 5 mm, 5 mm to 6 mm, 6 mm to 7 mm, 7 mm to 8 mm, 8 mm to 9 mm, 9 mm to 10 mm. In an example, the wells 302 have a diameter of about 6.8 mm. In other examples, the wells 302 have a diameter of about 8.25 mm. The wells may have a height of about 6 mm to 15 mm, 6 mm to 8 mm, 7 mm to 9 mm, 8 mm to 10 mm, 9 mm to 11 mm, 10 mm to 12 mm, 11 mm to 13 mm, 12 mm to 14 mm, or 13 mm to 15 mm. In at least one example, the wells may have a height of about 12.15 mm.

Figure 5A:
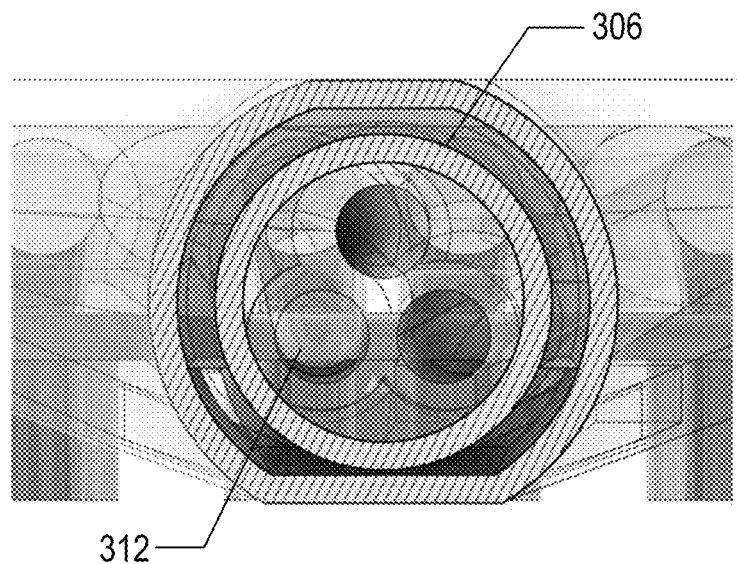
FIG. 5A is a cross-sectional view of an inlet that is split into three gas inlet channels.
Figure 5B:
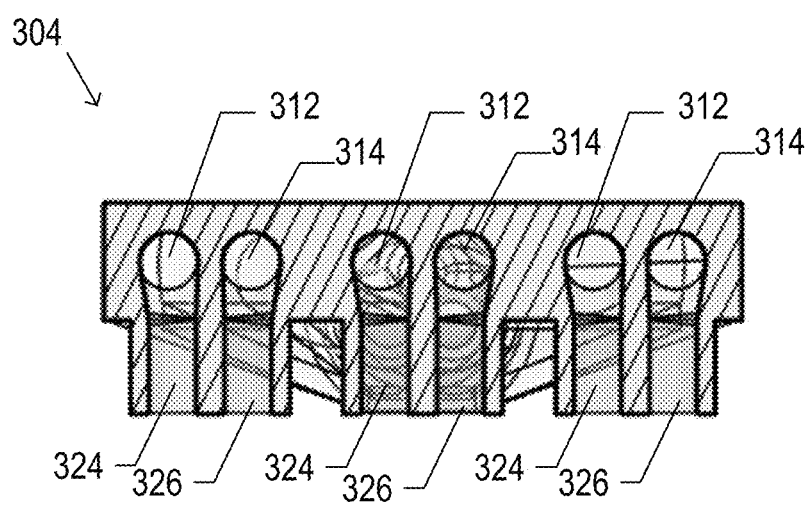
FIG. 5B is a cross-sectional view of the cover with three rows of gas inlet channels that are connected to well gas inlets and gas outlet channels that are connected to well gas outlets.

In an embodiment, the multi-well apparatus 300 may include three rows of wells 302. In one embodiment, each of the three rows of wells may include 8 wells 302. In an embodiment, the cover 304 includes three gas inlet channels 312 and three gas outlet channels 314. FIG. 5A is a cross-sectional view of an inlet 306 that is split into three gas inlet channels 312. The outlet 308 may be similarly split to receive the three gas outlet channels 314. FIG. 5B is a cross-sectional view of the cover 304 with three rows of gas inlet channels 312 that are connected to well gas inlets 324 and gas outlet channels 314 that are connected to well gas outlets 326.

Figure 6A:
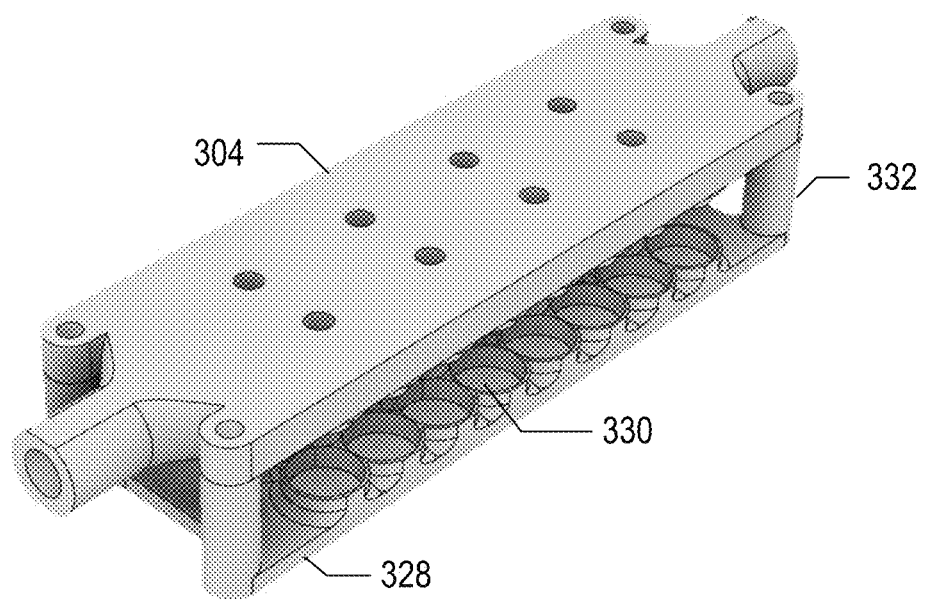
FIG. 6A is a multi-well apparatus with a tray, standoffs, and a cover, without any wells.
Figure 6B:
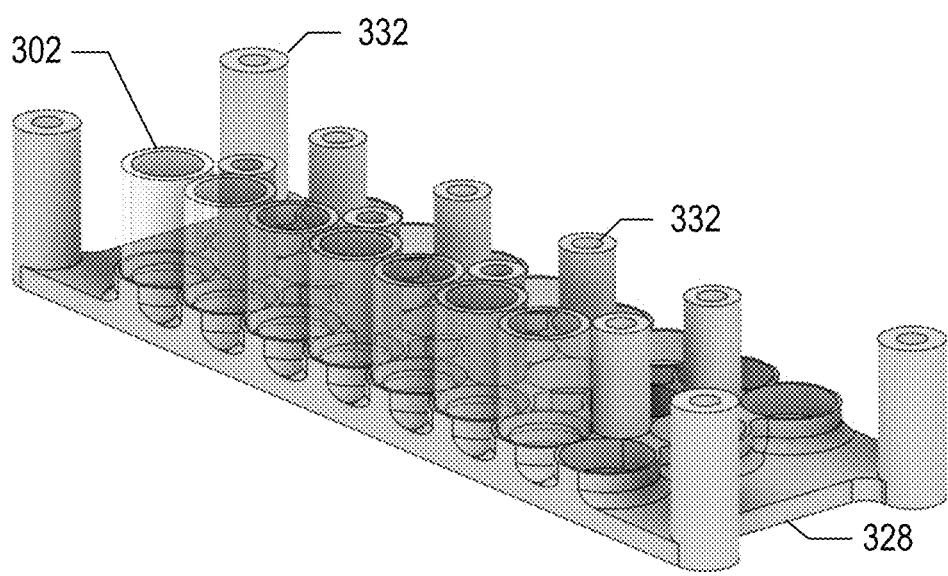
FIG. 6B is a multi-well apparatus with a tray and standoffs without a cover and partially filled with wells.

In an embodiment, the apparatus may further include a tray 328 configured to support the plurality of wells 302. The tray 328 may include one or more receptacles 330 to receive one or more wells 302, as shown in FIGS. 6A and 6B. The tray 328 provides stability for the wells 302 and aids in creating a hermetic system. In some examples, the number of receptacles 330 in the tray 328 match the number of wells 302 in a multi-well apparatus 300. The tray 328 and therefore the area of the wells 302 may have a length of about 50 mm to 200 mm, 50 mm to 100 mm, 75 mm to 125 mm, 100 mm to 150 mm, 125 mm to 175 mm, 150 mm to 200 mm. In an example, the length of the tray 328 or total wells 302 may be about 120 to 140 mm. The width of the tray 328 or total wells 302 may range from 10 mm to 100 mm, 10 mm to 30 mm, 20 mm to 40 mm, 30 mm to 50 mm, 40 mm to 60 mm, 50 mm to 70 mm, 60 mm to 80 mm, 70 mm to 90 mm, or 80 mm to 100 mm. In an example, the width of the tray 328 or total wells 302 may be about 25 mm to 30 mm. For example, the cover 304 may have a width of about 28 mm.

The tray 328 may include at least one standoff 332 configured to releasably connect with the cover 304. FIG. 6A shows a multi-well apparatus 300 with a tray 328, standoffs 332, and a cover 304, without any wells. FIG. 6B shows a multi-well apparatus 300 with a tray 328 and standoffs 332 without a cover and partially filled with wells 302. In some examples, the cover 304 may include at least one cutout (not shown) on a lower surface configured to receive the at least one standoff 332. In some embodiments, the at least one standoff 332 is integrated with the tray 328. In additional embodiments, the at least one standoff 332 comprises threads and is configured to be screwed into the tray 328 and/or the cover 304. The standoffs 332 may have varying sizes. For example, the standoffs 332 in the corners of the tray 328 may have a larger diameter than standoffs 332 in the middle of the tray 328. The standoffs 332 may have a diameter ranging from 3 mm to 10 mm, 3 mm to 5 mm, 4 mm to 6 mm, 5 mm to 7 mm, 6 mm to 8 mm, 7 mm to 9 mm, or 8 mm to 10 mm. In at least one example, the standoffs 332 at the corners may have an outer diameter of 6.4 mm and the standoffs 332 in the middle may have an outer diameter of 5.4 mm. The standoffs 332 may be generally cylindrical or rectangular in shape or may have any shape configured to support the cover 304 on the wells 302 and tray 328. In some embodiments, one or more of the standoffs 332 may have a center bore.

Figure 7A:
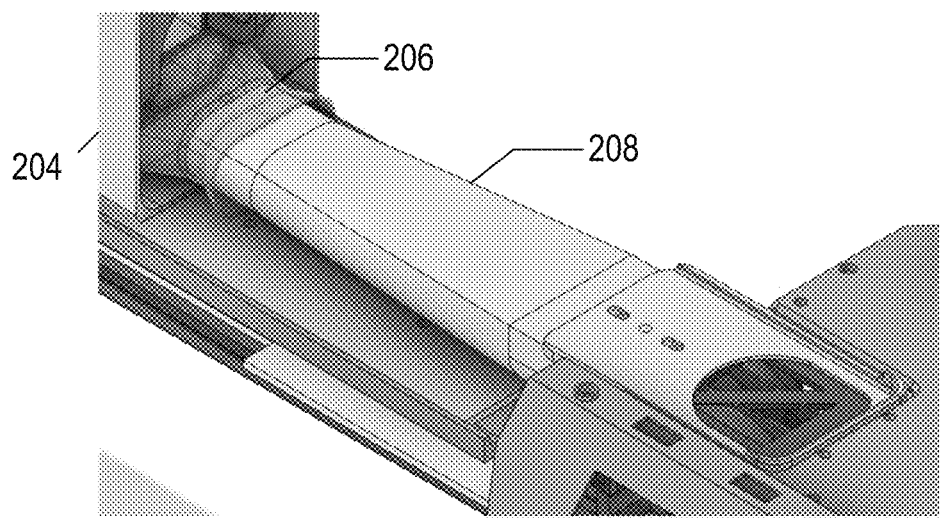
FIG. 7A shows the heating interface connected to a heating system via bracket and a heating manifold.
Figure 7B:
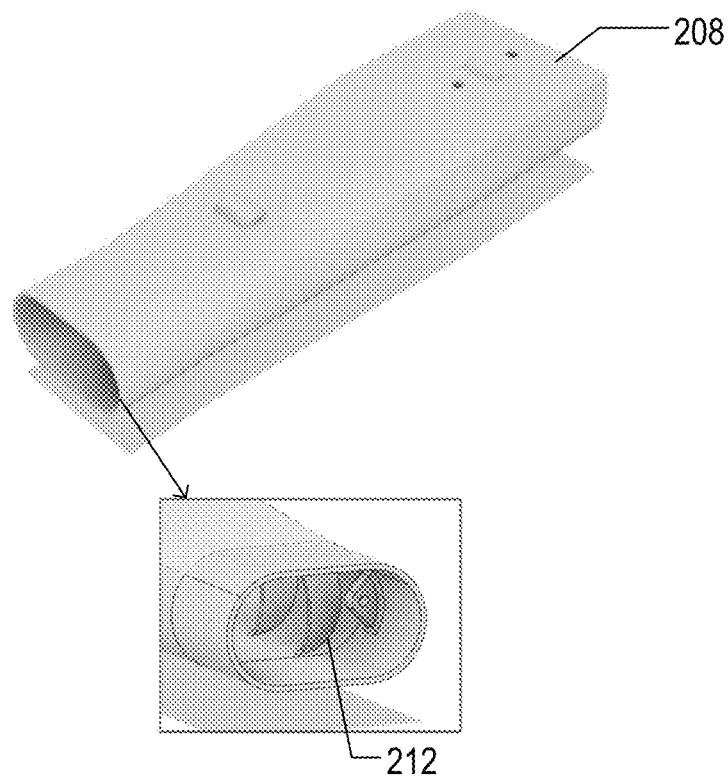
FIG. 7B is a front view of mixing fins that are curved to have a coiled arrangement to further aid in mixing air.
Figure 7C:
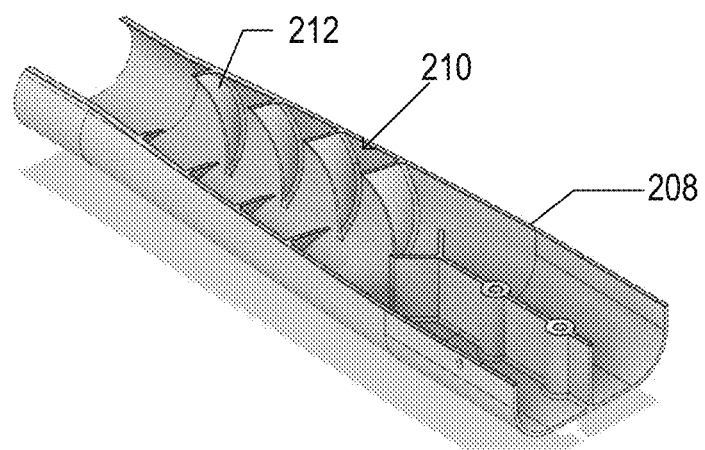
FIG. 7C is a top view of mixing fins that are curved to have a coiled arrangement to further aid in mixing air.

In an embodiment, the system may further include a heating interface 208 configured to connect to the resonator body 204 via the intake connector 206, as seen in FIGS. 7A-7C. In an example, the heating interface 208 may include a mixing area 210 configured to receive two air flows at different temperatures, mix the two air flows to produce the conditioned air, and output the conditioned air. In some embodiments, the heating interface 208 may narrow at the end configured to connect to the intake connector 206. For example, the input end of the heating interface 208 may have a larger diameter than the output end of the heating interface 208. The heating interface 208 may have a length ranging from 150 mm to 300 mm, 150 mm to 200 mm, 175 mm to 225 mm, 200 mm to 250 mm, 225 mm to 275 mm, or 250 mm to 300 mm. In an example, the length of the heating interface 208 may be about 210 mm to 220 mm. In at least one example, the length of the heating interface 208 may be about 214.5 mm. The heating interface 208 may have a width ranging from about 50 mm to 100 mm, 50 mm to 70 mm, 60 mm to 80 mm, 70 mm to 90 mm, or 80 mm to 100 mm. In at least one example, the heating interface 208 has a width of about 70 mm.

Figure 7D:
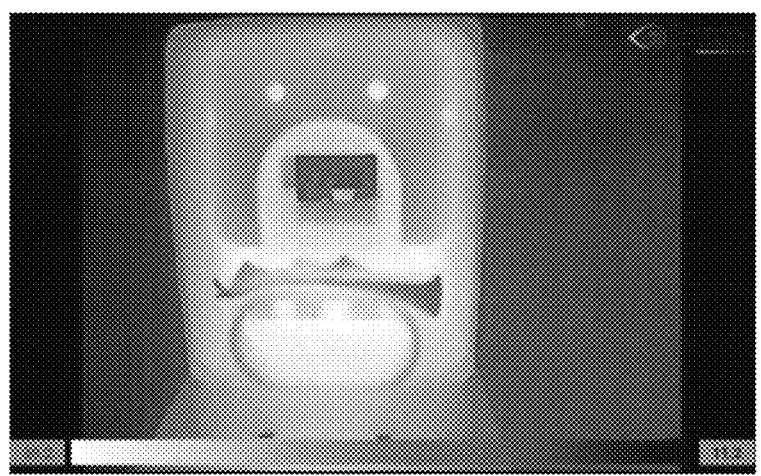
FIG. 7D is a thermal imaging showing temperature distribution using mixing fins in a coiled arrangement.

Referring to FIGS. 7B and 7C, the mixing area 210 may include a plurality of mixing fins 212 to aid in producing the conditioned air with a homogeneous temperature. The mixing fins 212 may be curved to have a coiled arrangement to further aid in mixing the air, as seen in FIGS. 7B and 7C. FIG. 7D is a thermal imaging showing temperature distribution using mixing fins 212 in a coiled arrangement. In some embodiments the temperature of the conditioned air may be about 37° C.±0.5° C. or 37° C.±1° C. In other embodiments, the temperature of the conditioned air may be 32° C. to 40° C. In one example, the conditioned air is maintained at 37° C.±0.5° C. as is required for maintaining mammalian cells. In some embodiments, a target temperature of the conditioned air may vary based upon several factors, such as the size of the tissue or organ or the type of cell. The system 200 may further include a temperature sensor for measuring the temperature within the resonator 228 or at any point within the system 200. In some embodiments, the system 200 may include a feedback loop, where the temperature of the conditioned air can be adjusted based on the measurement from the temperature sensor to maintain a target temperature within the resonator 228.

Figure 8A:
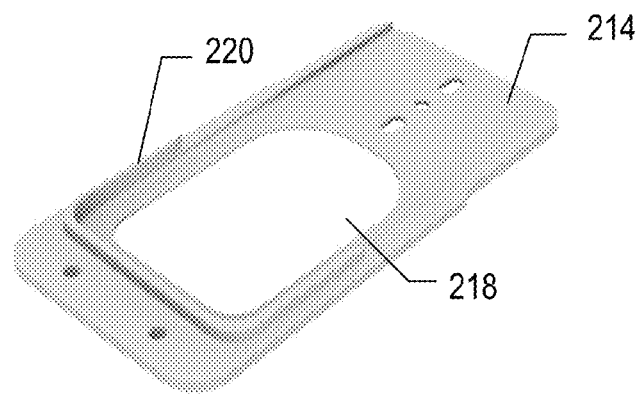
FIG. 8A is an example bracket having an opening and rim for receiving the heating manifold.
Figure 8B:
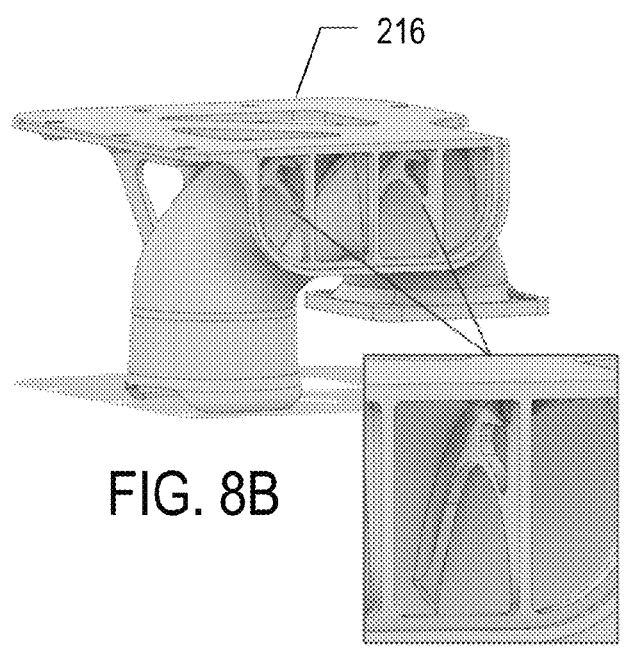
FIG. 8B is an example heating manifold configured to connect to a heating system and receive flows of two different temperatures of air.
Figure 8C:
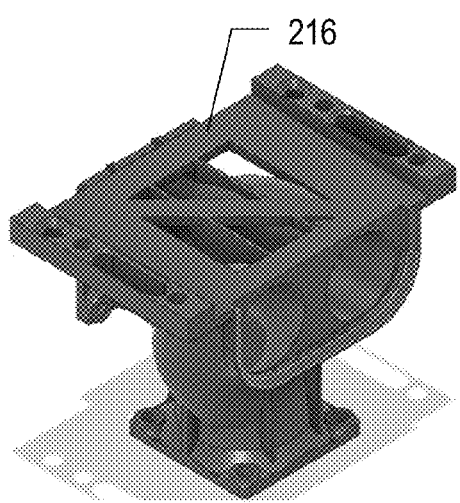
FIG. 8C is an example heating manifold configured to connect to a heating system and receive flows of two different temperatures of air.

The heating interface 208 may be connected to a heating system via bracket 214 and a heating manifold 216, as seen in FIG. 7A. FIG. 8A shows an example bracket 214 having an opening 218 and rim 220 for receiving the heating manifold 216. The bracket 214 may have a length ranging from about 120 mm to about 150 mm, 120 mm to 130 mm, 130 mm to 140 mm, or 140 mm to 150 mm. In some examples, the bracket 214 may have a length of 125.5 mm or 145.5 mm. The bracket 214 may have a width ranging from about 50 mm to 100 mm, 50 mm to 70 mm, 60 mm to 80 mm, 70 mm to 90 mm, or 80 mm to 100 mm. In at least one example, the bracket 214 has a width of about 70 mm. FIGS. 8B and 8C show example heating manifolds 216 configured to connect to a heating system and receive flows of two different temperatures of air.

In some embodiments, the system 200 may further include a humidity sensor configured to measure the moisture content of the conditioned air. The conditioned air flow may have a relative humidity of between about 30% and about 100% or between about 30% and 50%.

Figure 9A:
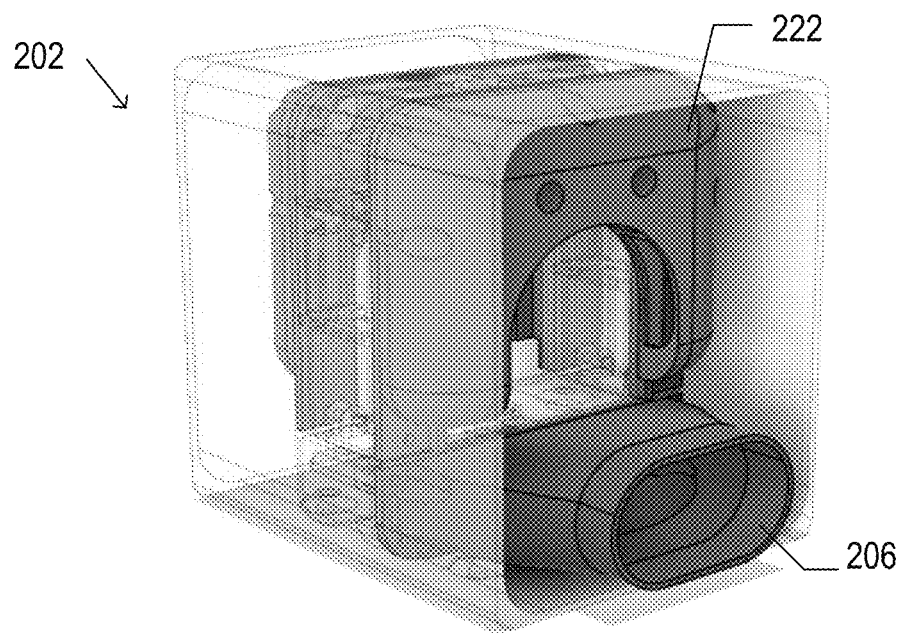
FIG. 9A is a resonator assembly with an intake connector and air directors.
Figure 9B:
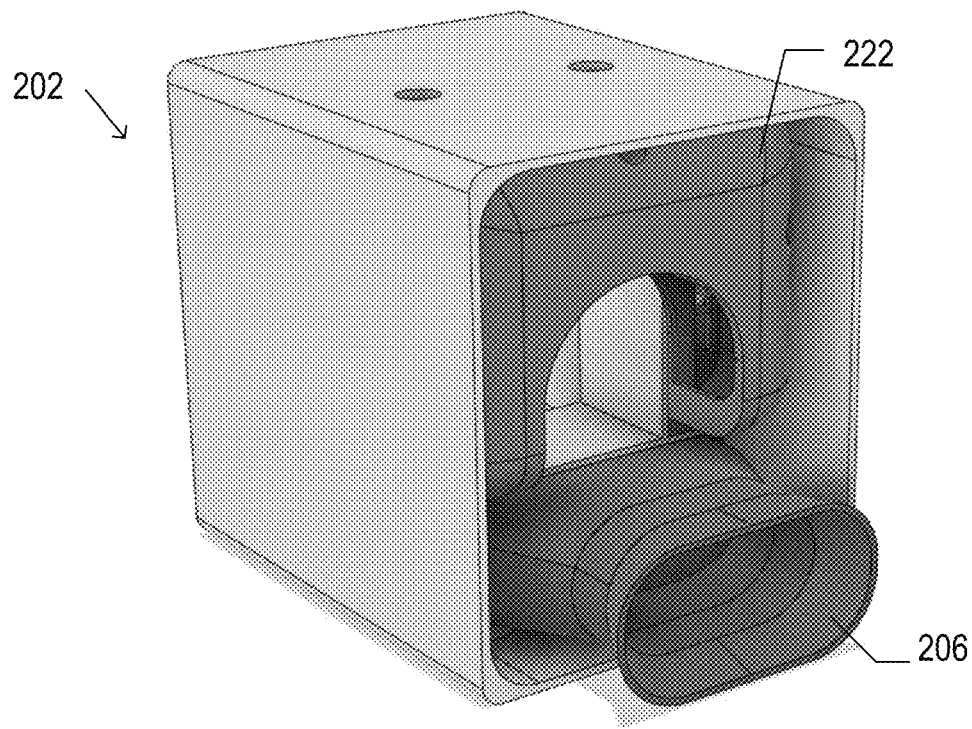
FIG. 9B is a resonator assembly with an intake connector and air directors.
Figure 10A:
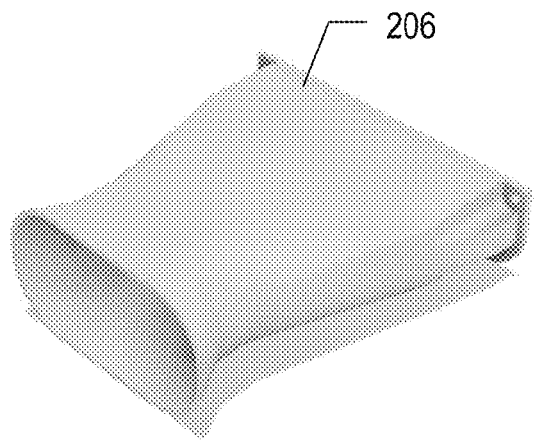
FIG. 10A is an example intake connector.
Figure 10B:
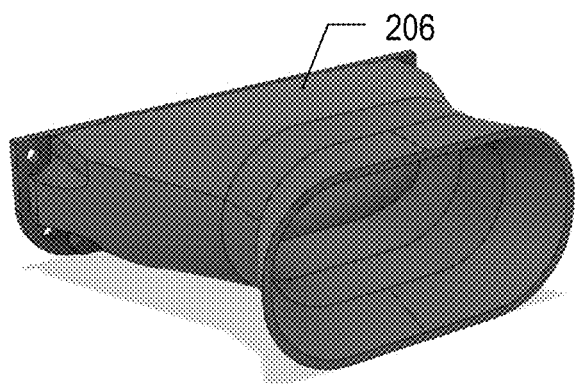
FIG. 10B is an example intake connector.
Figure 10C:
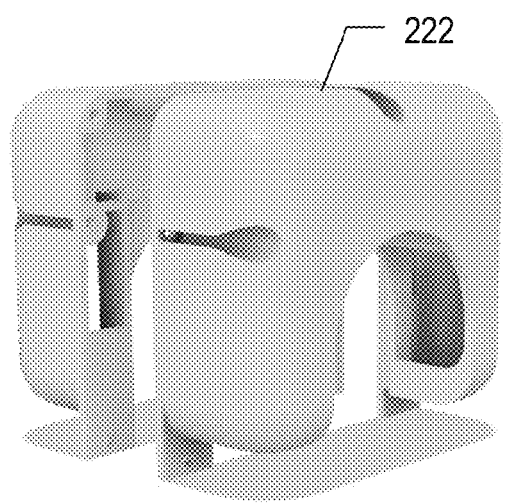
FIG. 10C is an example of air directors with a shape configured to direct the conditioned air around the resonator.
Figure 10D:
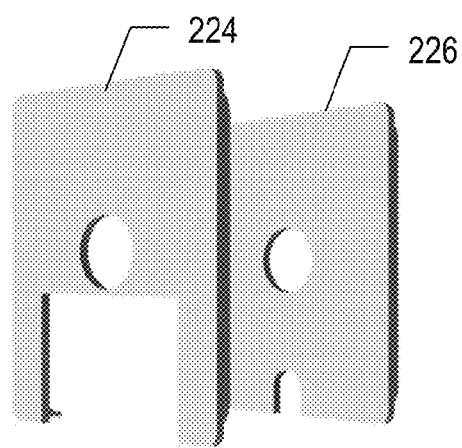
FIG. 10D is an example front cover and back cover.

The resonator assembly 202 may further include the intake connector 206, air directors 222, and/or front and back covers 224, 226. In some examples, the imaging system may include an integrated heat system that uses heated air to maintain the temperature inside the apparatus. Hot air from the integrated heat system mixes inside the heating interface 208 and intake connector 206 and heats the sample via the air directors 222. The front and back covers 224, 226 aid in maintaining a 37° C. environment for cells. FIGS. 9A and 9B show a resonator assembly 202 with an intake connector 206 and air directors 222. FIGS. 10A and 10B show example intake connectors 206. The intake connector 206 may have a first end configured to connect to the resonator assembly 202 and a second end configured to connect to a heating interface 208. The intake connector 206 may be tapered at one or both ends. In some examples, the second end may be flared to facilitate connection to the heating interface 208. FIG. 10C shows example air directors 222 with a shape configured to direct the conditioned air around the resonator. FIG. 10D shows an example front cover 224 and back cover 226.

Figure 11A:
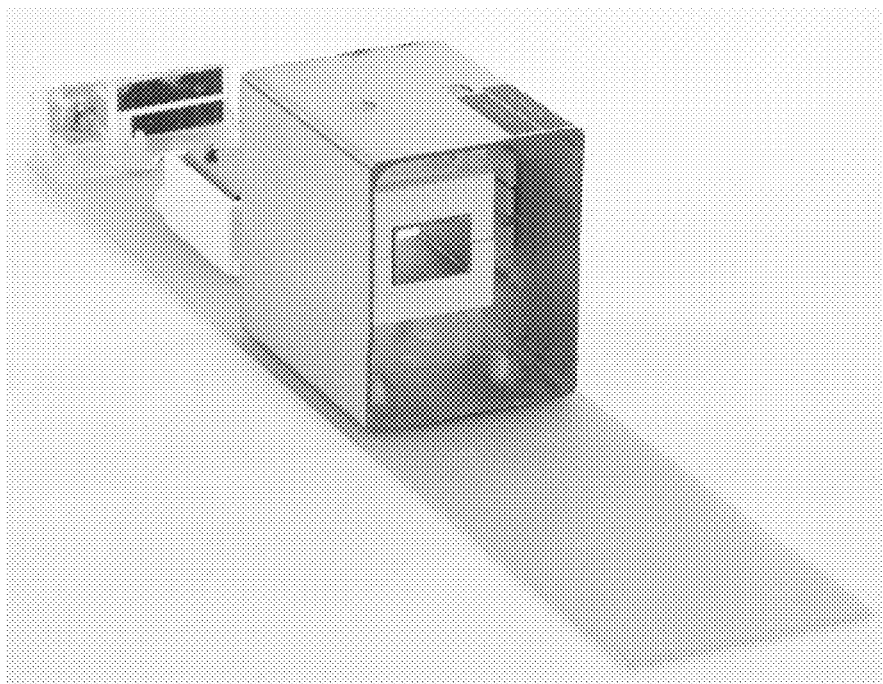
FIG. 11A is an image of an example square resonator assembly.
Figure 11B:
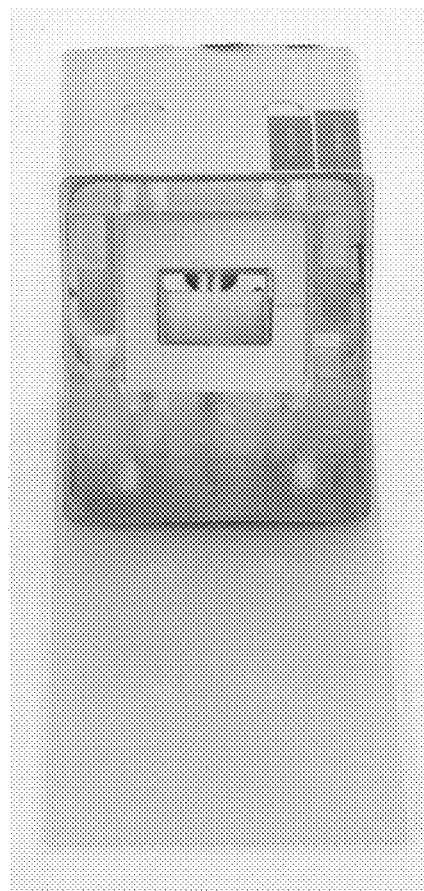
FIG. 11B is an image of an example square resonator assembly.
Figure 12A:
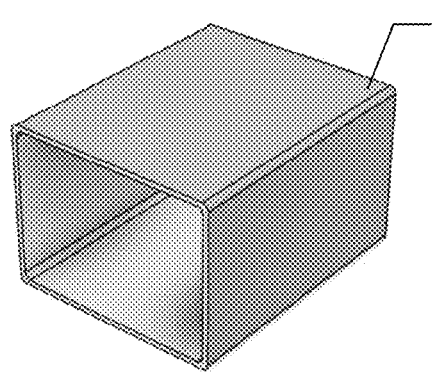
FIG. 12A is an example of the body of the resonator assembly comprising a resonator shield.
Figure 12B:
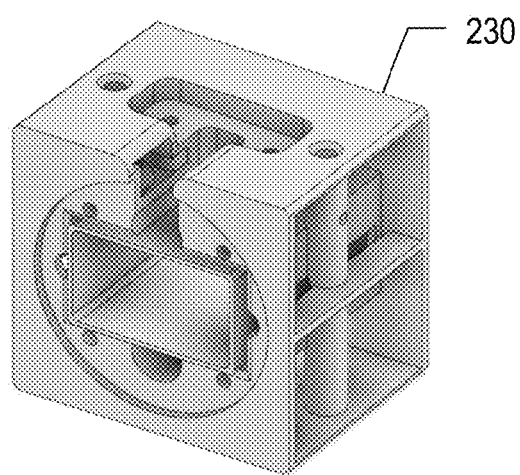
FIG. 12B is an example of the body of the resonator assembly comprising a square resonator and square resonator block.
Figure 12C:
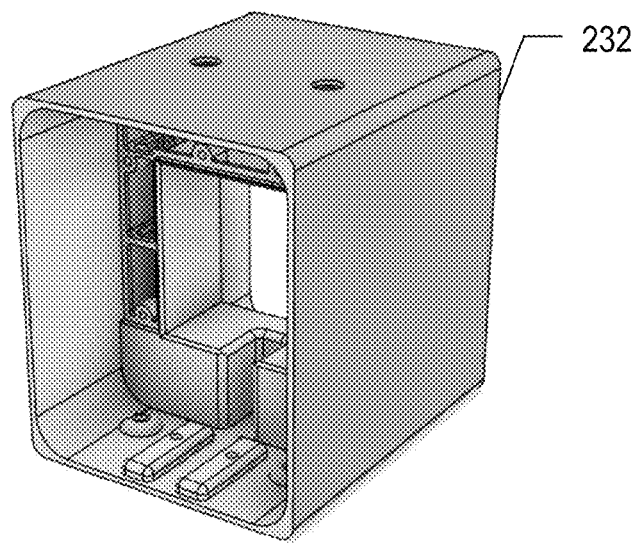
FIG. 12C is an example of the body of the resonator assembly comprising a square resonator, square resonator block, and resonator shield.

In an embodiment, the resonator assembly 202 may be square or rectangular. FIGS. 11A and 11B are images of example square resonator assemblies. The body 204 of the resonator assembly 202 may comprise a square resonator 228, square resonator block 230, and resonator shield 232, as shown in FIGS. 12A-12C. In some examples, the square resonator 228 and/or the resonator shield 232 may be made of copper. In an embodiment, the resonator assembly 202 utilizes a 2-gap loop square shaped resonator which may be compatible with the multi-well apparatus 300. It provides the filling factor needed to image 12 strip-wells simultaneously and to obtain a homogeneous magnetic field within the cavity. In an example, the square resonator 228 is housed in a square resonator block 230 for stability which is mounted inside a copper lined resonator shield 232 for RF emission protection and to improve the performance of the resonator 228.

The resonator 228 may have a length/width of about 30 mm to 50 mm, 30 mm to 40 mm, 35 mm to 45 mm, or 40 mm to 50 mm. In an example, the resonator 228 may have a length/width of 38 mm. In another example, the resonator 228 may have a length/width of 42 mm.

Figure 12D:
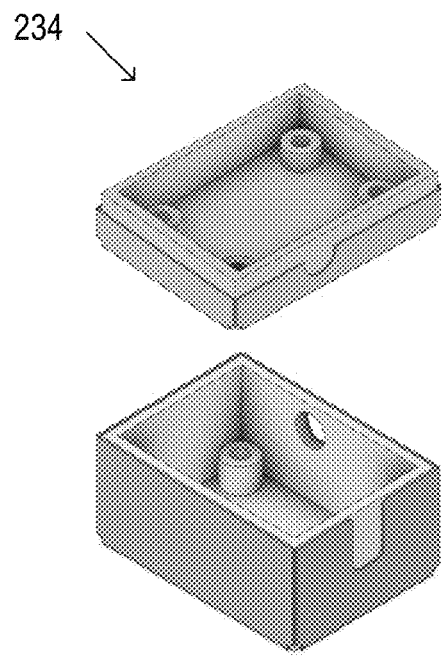
FIG. 12D is an example of the resonator assembly including a copper match box connected to the resonator.
Figure 12E:
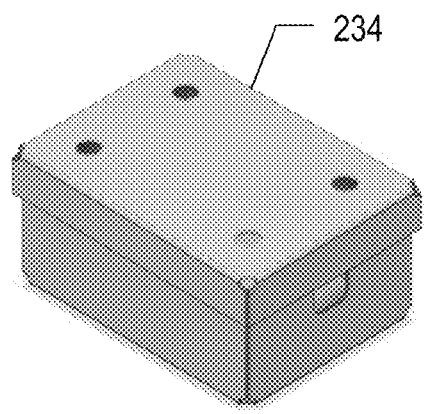
FIG. 12E is an example of the resonator assembly including a copper match box connected to the resonator.
Figure 12F:
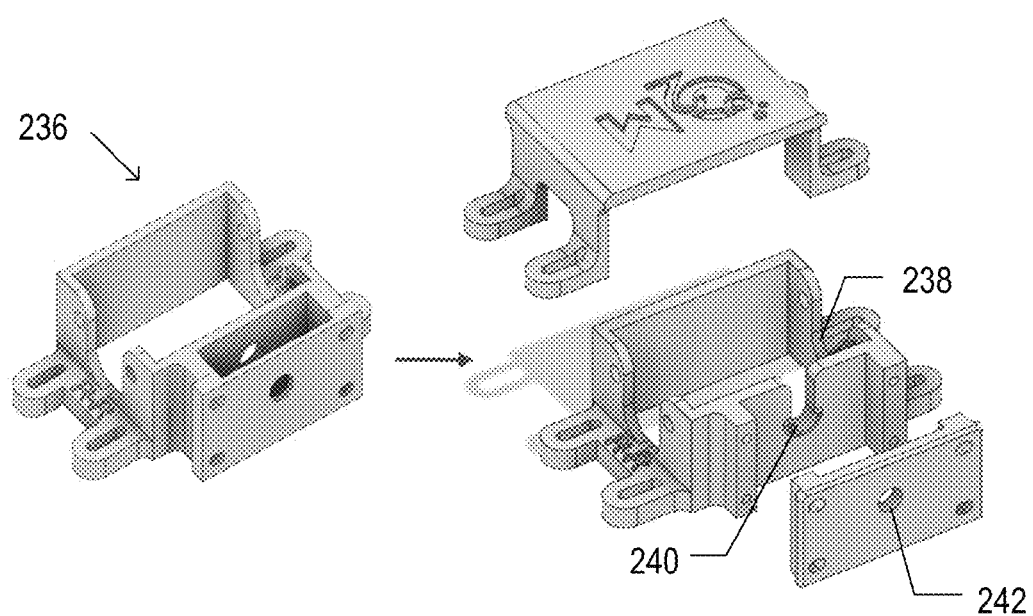
FIG. 12F is an example of the resonator assembly including a match box mount connected to the resonator.

In additional embodiments, as seen in FIGS. 12D-12F, the resonator assembly 202 may further include a copper match box 234 and/or a match box mount 236 connected to the resonator 228. The match box mount 236 may include a slot cut-out 238 for installation of the match box 234, a tuning wheel (not shown), a lip 240 configured to provide mechanical support for the tuning wheel, and/or a hole 242 for the tuning wheel.

EXAMPLES

Example 1

Figure 13B:
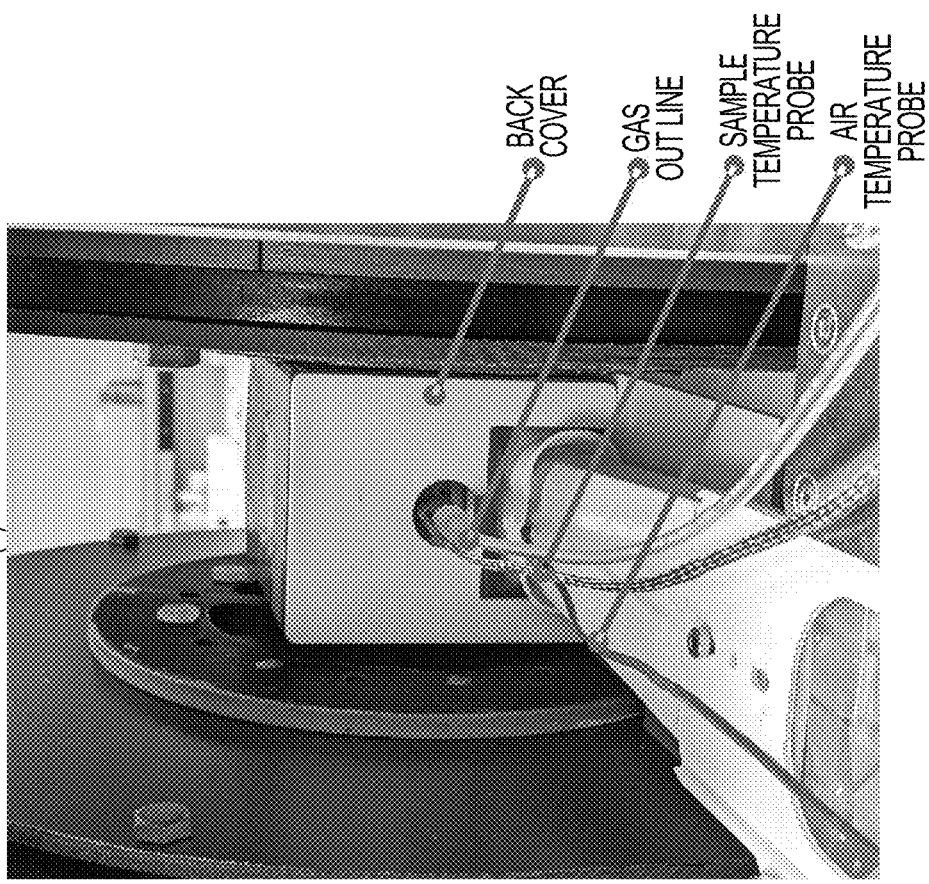
FIG. 13B is an experimental set-up of a system with a resonator and multi-well apparatus.
Figure 13A:
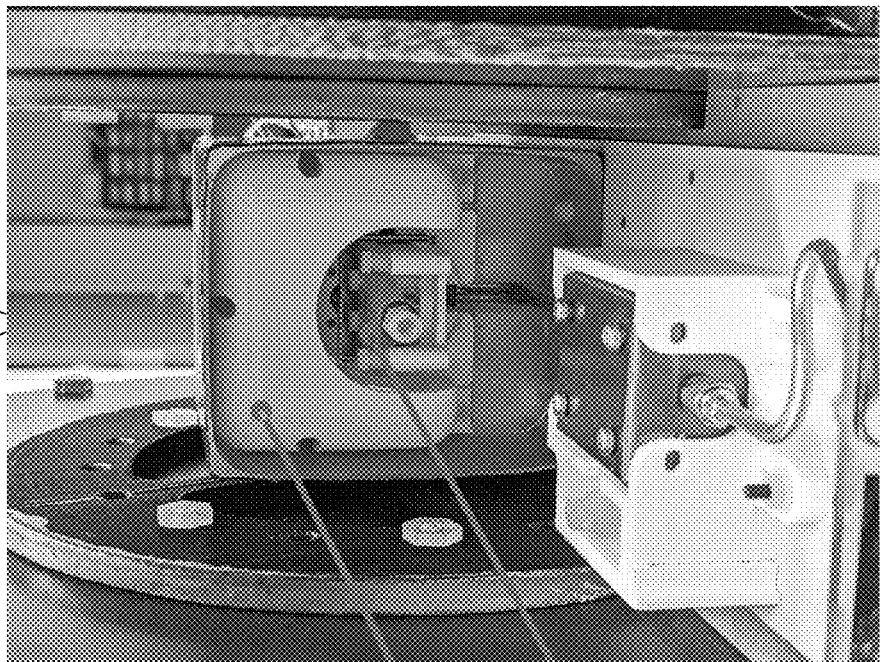
FIG. 13A is an experimental set-up of a system with a resonator and multi-well apparatus.

FIGS. 13A and 13B show an experimental set-up of a system with a resonator and multi-well apparatus. FIG. 13A shows a front view of the resonator with a multi-well plate cover (front cover of resonator not shown). FIG. 13B shows a rear view of the resonator with a back cover, gas-out line, sample, and air temperature probes.

Example 2

Figure 14A:
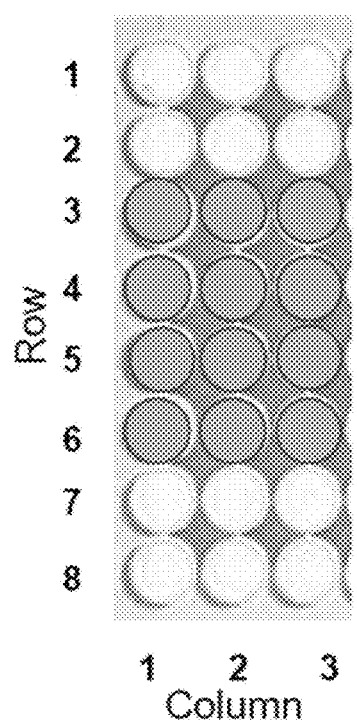
FIG. 14A shows results testing the system with a 1 mM OX071 in PBS.
Figure 14B:
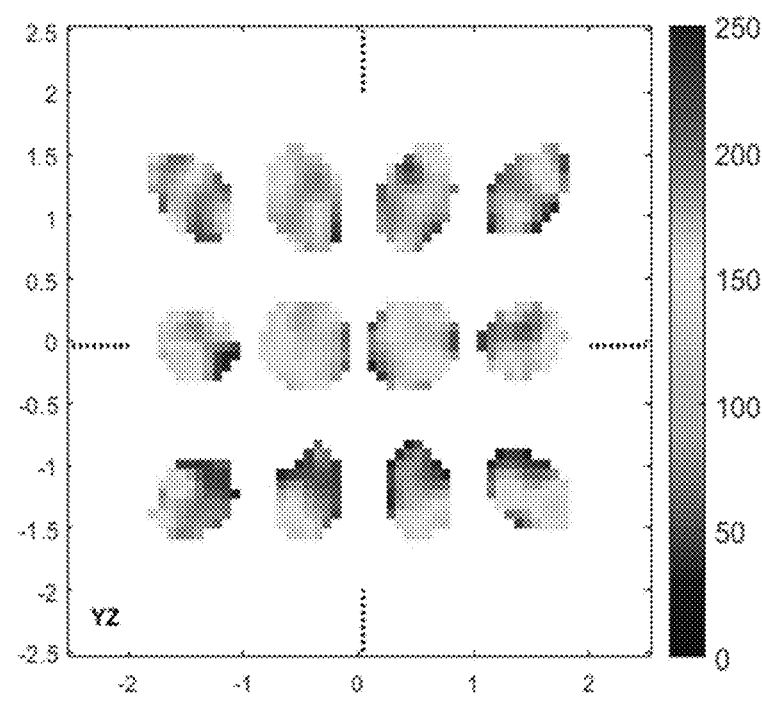
FIG. 14B shows $pO_2$ map results testing the system with a 1 mM OX071 in PBS.
Figure 14C:
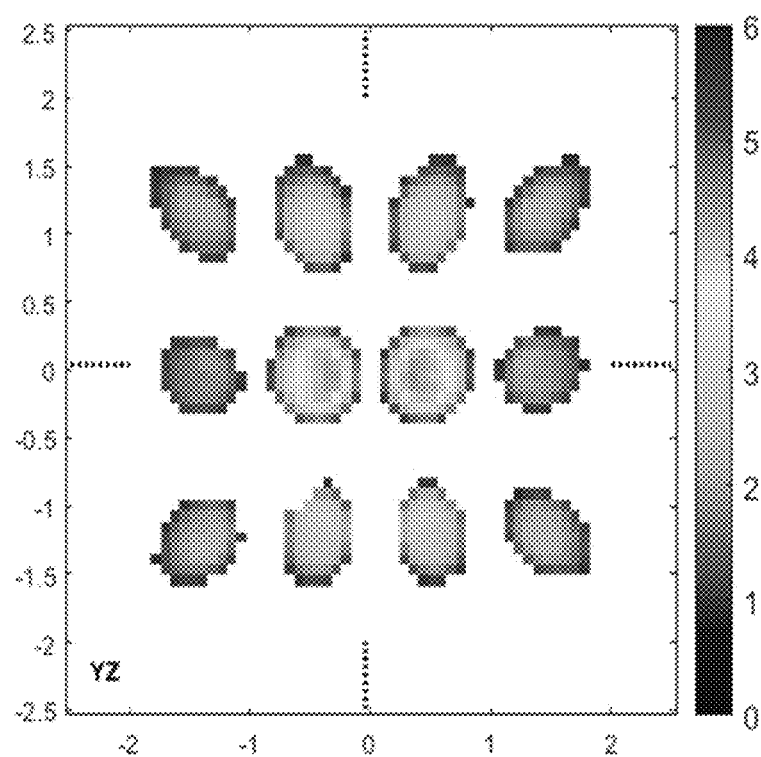
FIG. 14C is a signal amplitude map obtained using EPROI and a resonator operating at about 720 MHz while testing the system with a 1 mM OX071 in PBS.

FIGS. 14A-14C show results testing the system with a 1 mM OX071 in PBS. Approximately 150 uL of 1 mM OX071 in PBS was pipetted in four middle columns of the strip wells (FIG. 14A) and a 95% air, 5% CO2 gas mixture was delivered at a flow rate of 3.75 ccm at room temperature. FIG. 14B is a $pO_2$ map and FIG. 14C is a signal amplitude map obtained using EPROI and a resonator operating at about 720 MHz.

Example 3

Figure 15A:
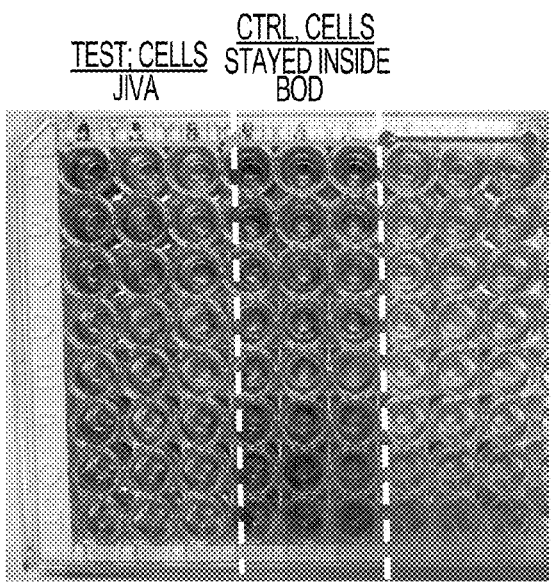
FIG. 15A shows results testing the cell viability system with 6,000 HEK293 cells per well.
Figure 15B:
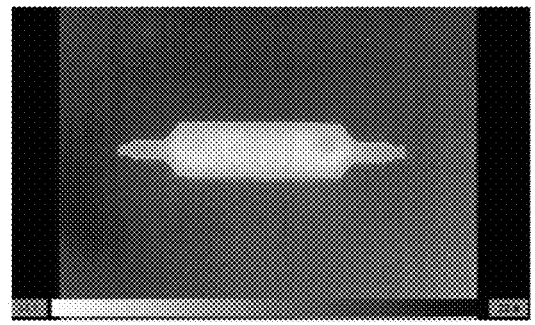
FIG. 15B shows results testing the cell viability system with 6,000 HEK293 cells per well.
Figure 15C:
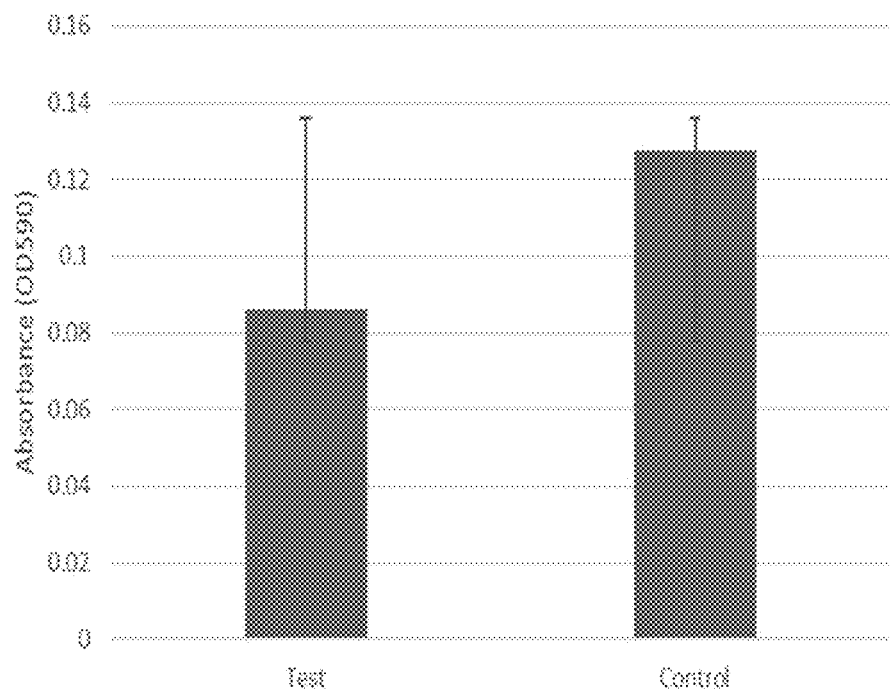
FIG. 15C shows results testing the cell viability system with 6,000 HEK293 cells per well.

FIGS. 15A-15C show results testing the cell viability system with 6,000 HEK293 cells per well. The temperature was ~36.9° C. in 40 mins. The humidity was 85% RH in 45 mins to 100% RH. An MTT Assay had a p-value=0.05814 (>0.05). The cell morphology of cells in the system appeared similar to the control.

Example 4

Figure 16A:
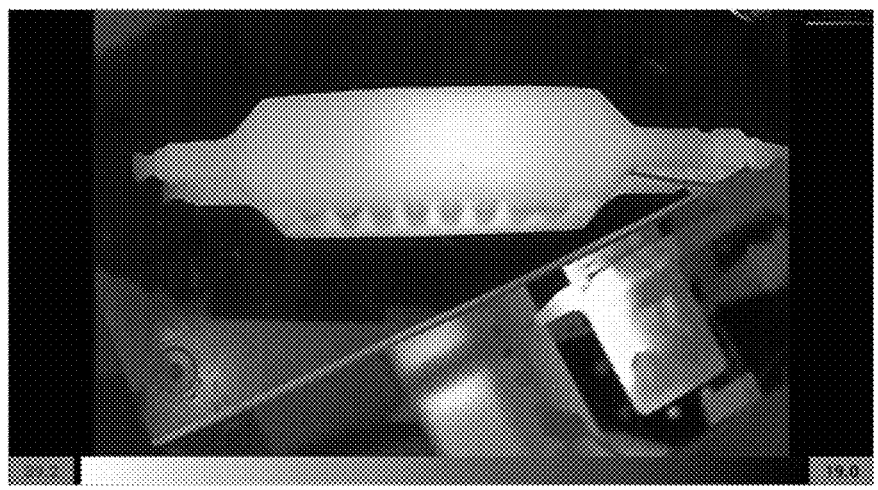
FIG. 16A shows results testing the cell viability system with 12,000 HEK293 cells per well.
Figure 16B:
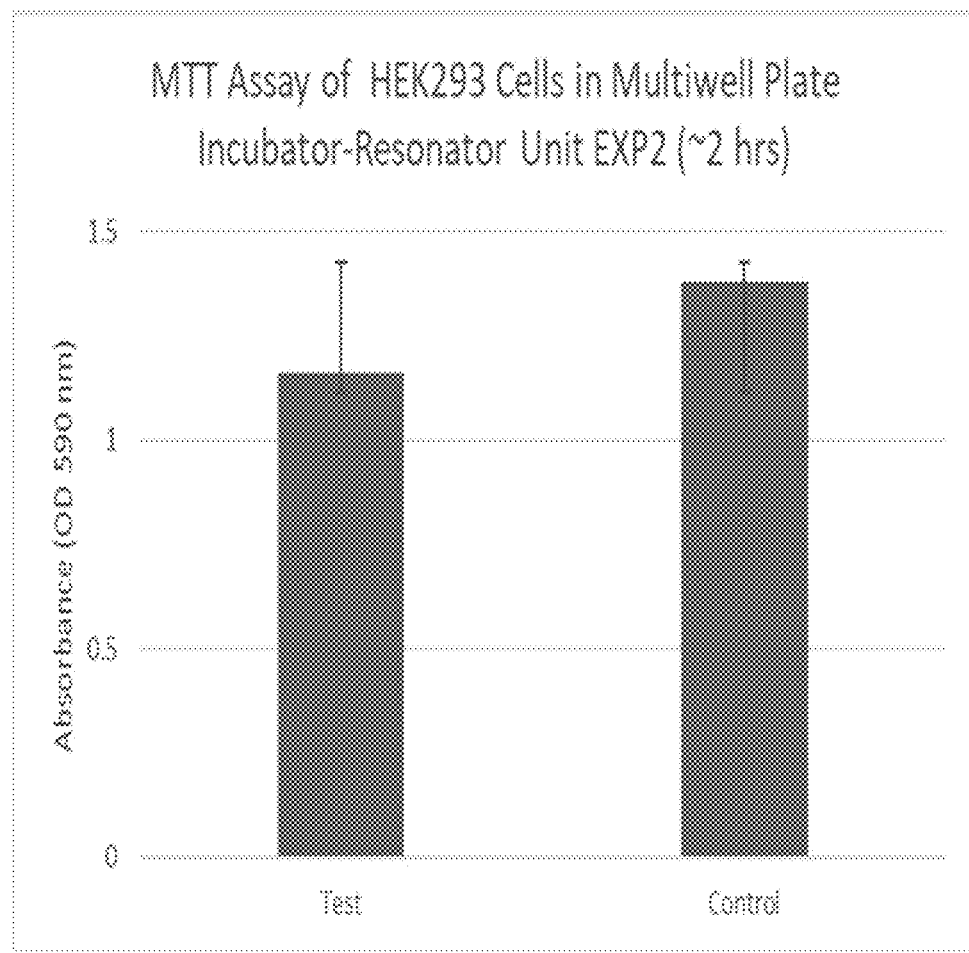
FIG. 16B shows results testing the cell viability system with 12,000 HEK293 cells per well.
Figure 16C:
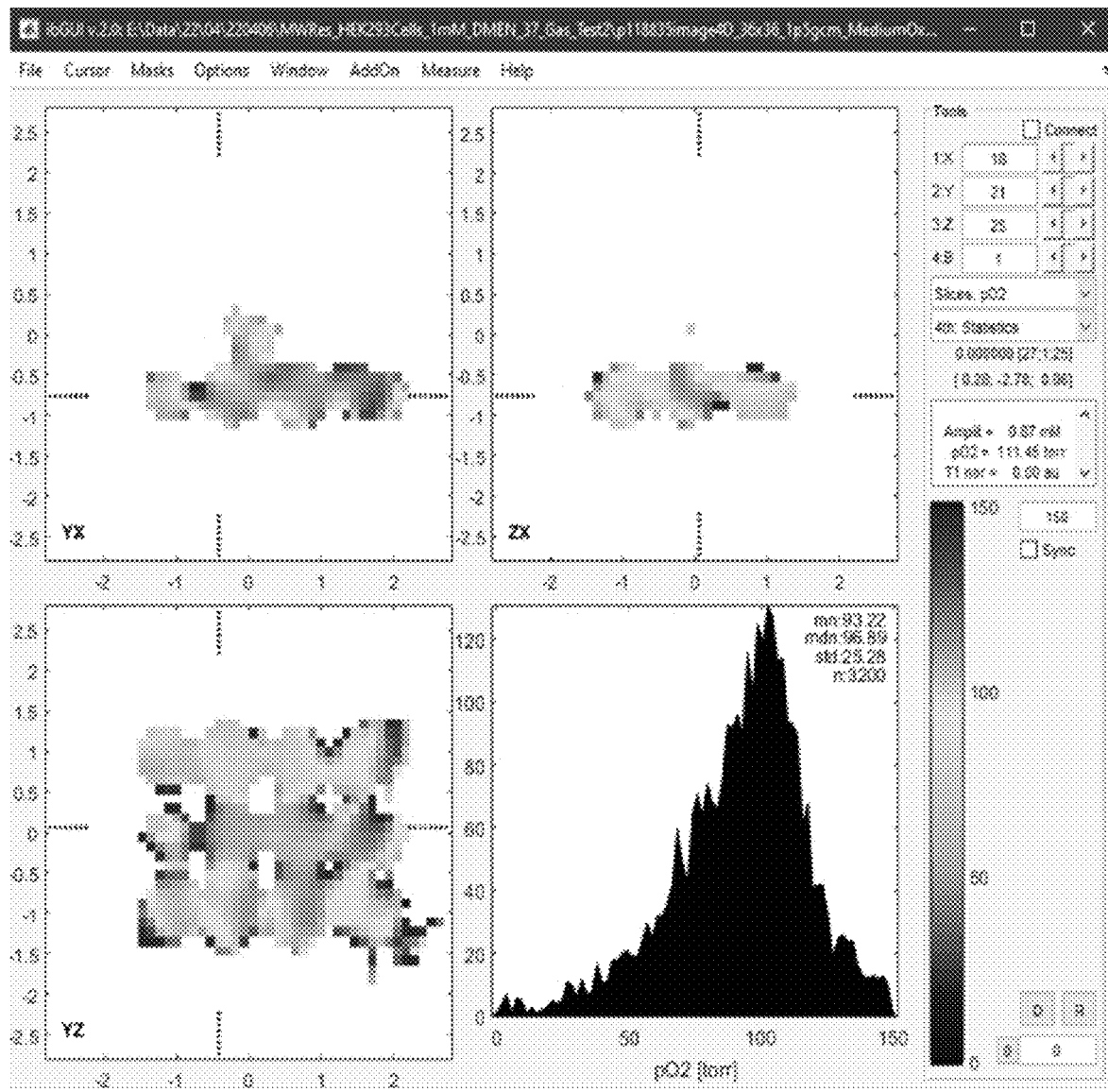
FIG. 16C shows results testing the cell viability system with 12,000 HEK293 cells per well.

FIGS. 16A-16C show results testing the cell viability system with 12,000 HEK293 cells per well. EPROI with T1 & IRESE were used. The temperature was ~37.5° C. in 5 mins. The humidity was 95% RH at start to 100% RH. The pH in the system was 8.07 and the control was pH 7.96. An MTT Assay had a p-value=0.002 (<0.05). The cell morphology of cells in the system appeared similar to the control.

Example 5

Figure 17:
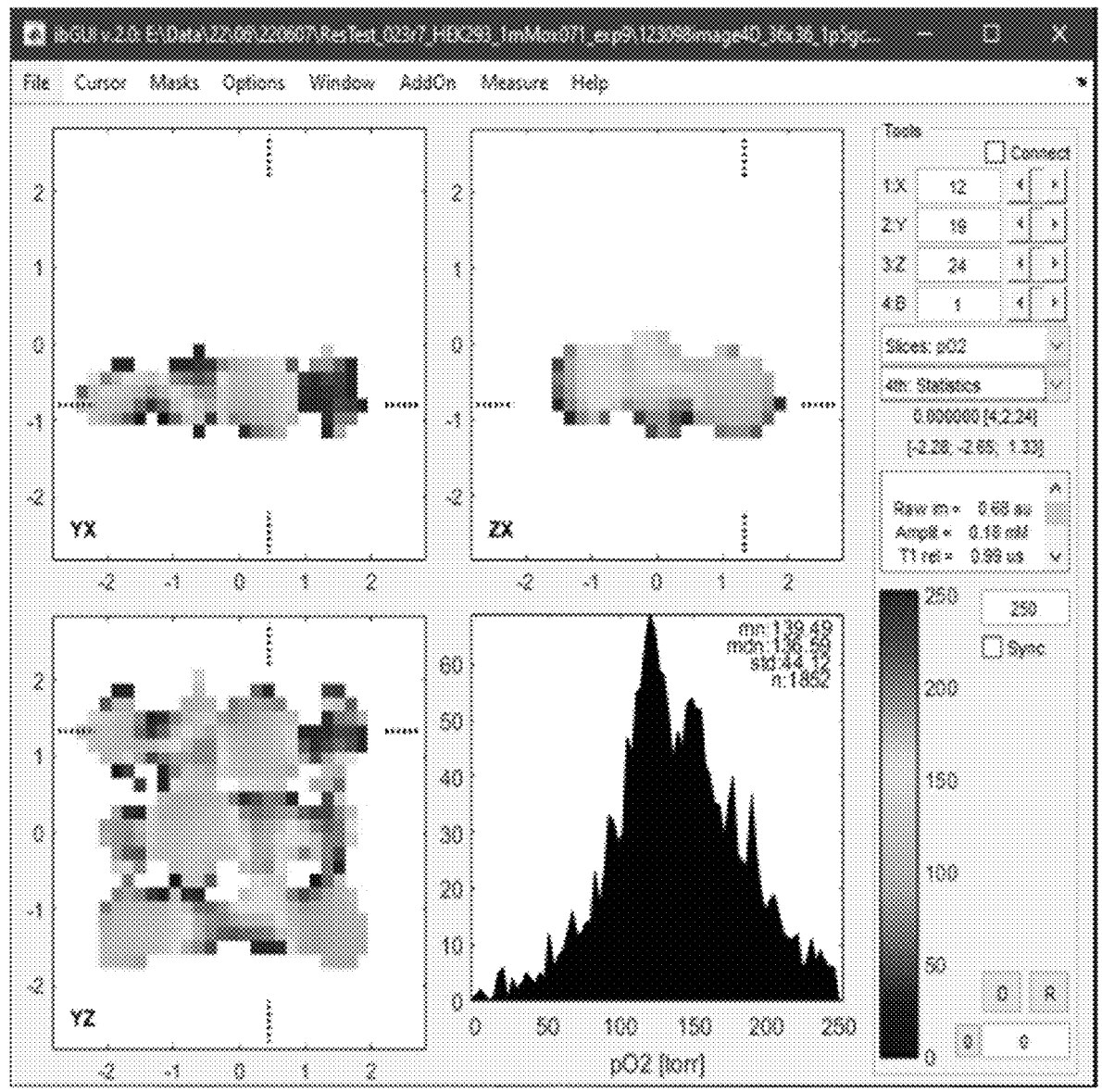
FIG. 17 shows results of imaging HEK293 cells with 1 mM OX071 via EPROI in the cell viability system.

FIG. 17 shows results of imaging HEK293 cells with 1 mM OX071 via EPROI in the cell viability system. The wells contained cells at 5K and 50K densities, along with cell media as control with total volume of 150 uL in each well. ~1.5 uL of 100 mM OX071 was added to the wells in rows 3-6 before the experiment. No RF interference was observed using a shielded probe. Table 1 shows the pattern of the cells in the wells in the multi-cell apparatus.

TABLE 1

| Pattern in YZ | | | |
| --- | --- | --- | --- |
| M | 5K | 50K | M |
| 5K | 50K | M | 5K |
| 50K | M | 5K | 50K |

Example 6

Figure 18A:
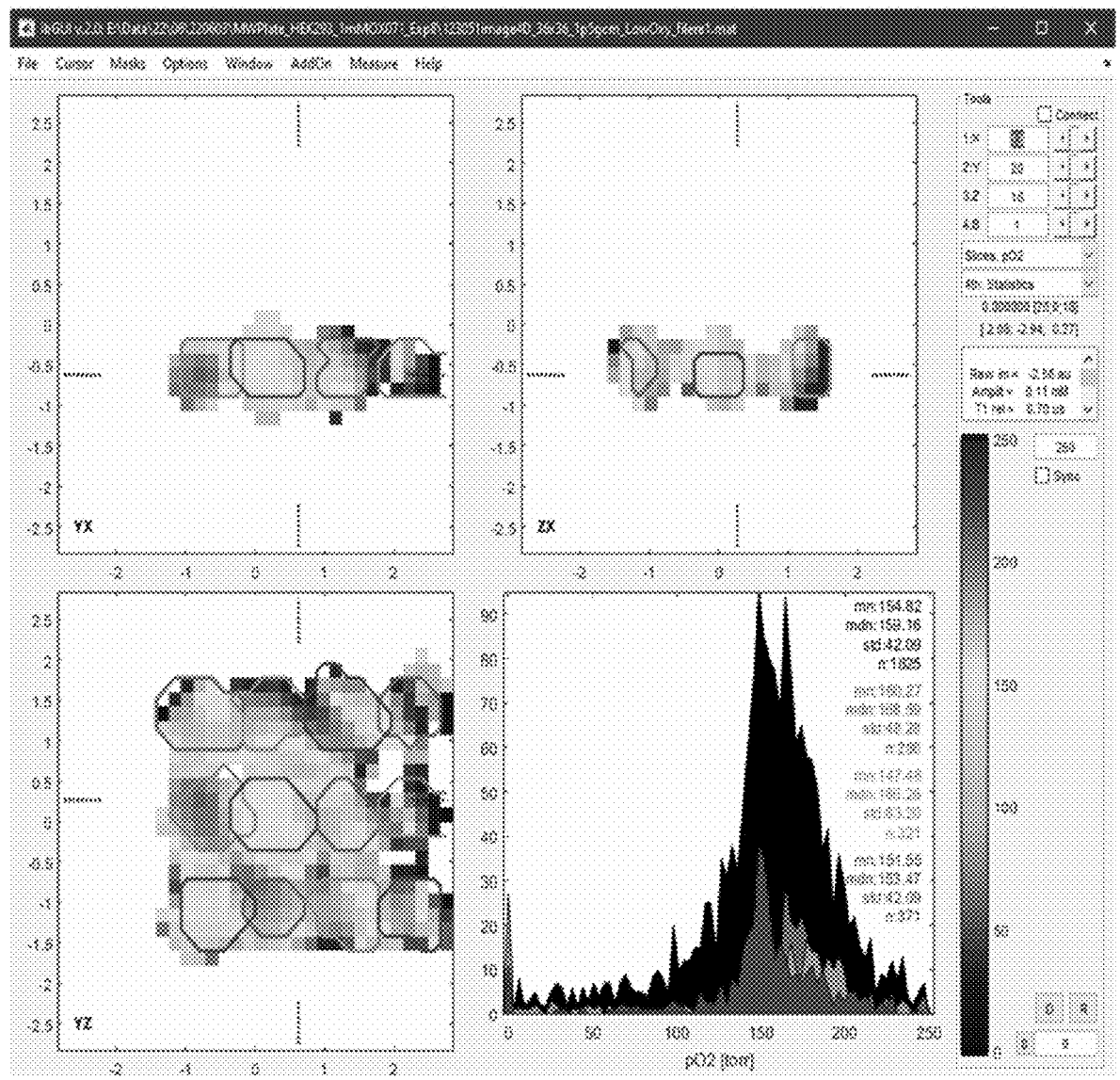
FIG. 18A shows results from imaging HEK293 cells with 1 mM trityl via EPROI in the cell viability system.
Figure 18B:
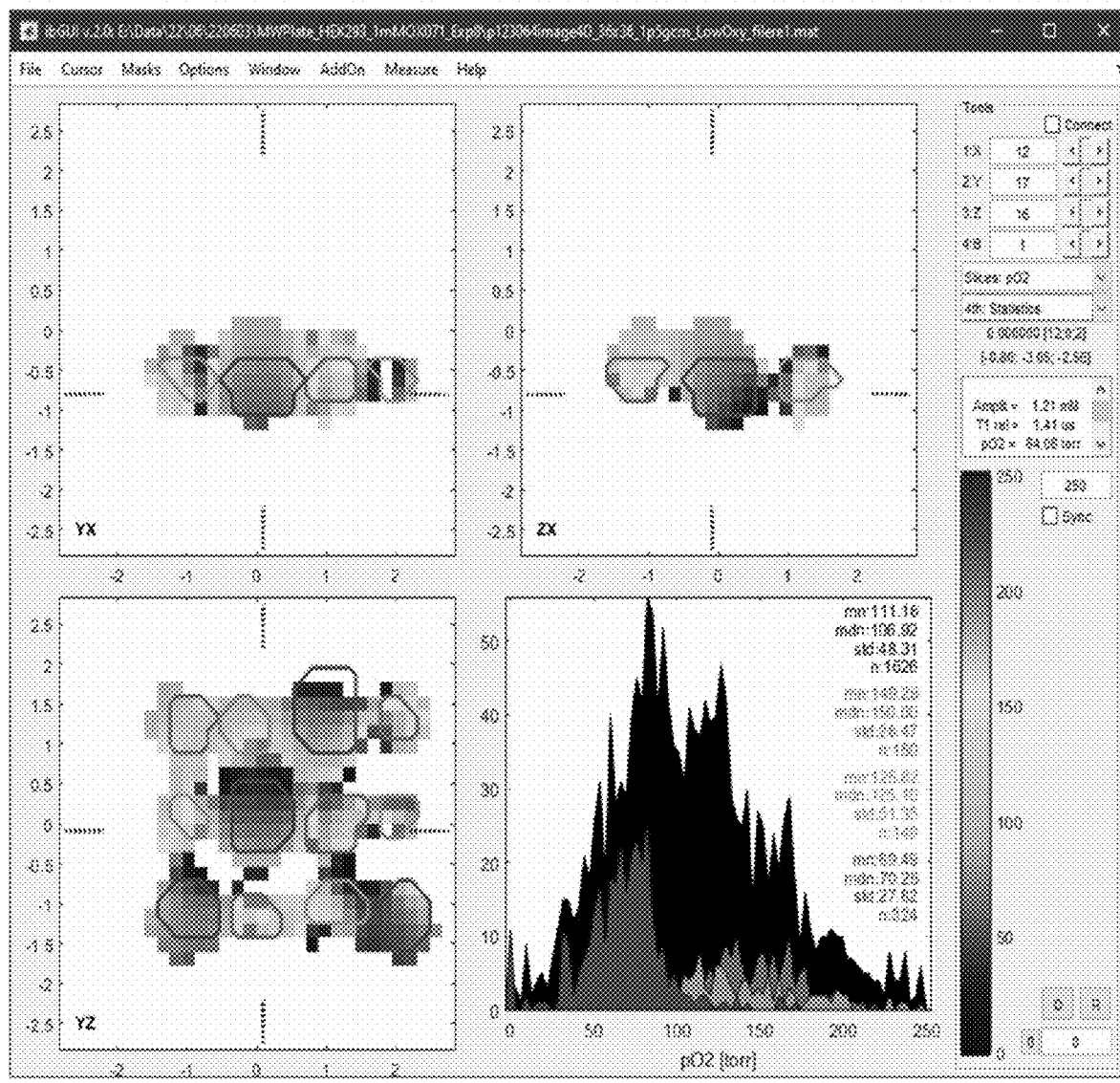
FIG. 18B shows results from imaging HEK293 cells with 1 mM trityl via EPROI in the cell viability system.
Figure 18C:
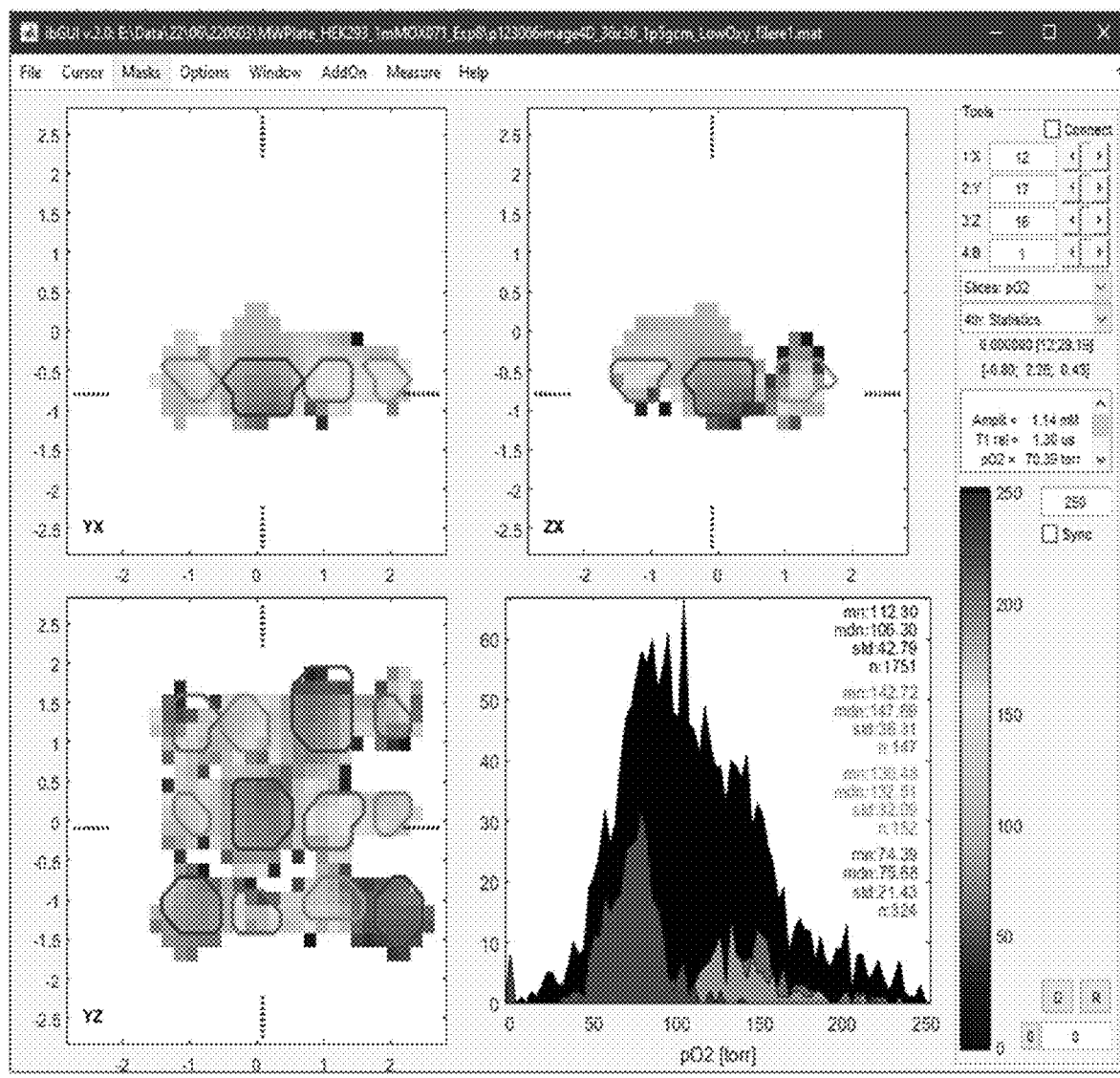
FIG. 18C shows results from imaging HEK293 cells with 1 mM trityl via EPROI in the cell viability system.

FIGS. 18A-18C show results from imaging HEK293 cells with 1 mM trityl via EPROI in the cell viability system. Settings for EPROI included Field: −3.207 G; Attn: 5 dB; RefPhase: 45; Signal ~1.4V; Res F=722 Mhz, −40 dB. The wells contained cells at 5K and 50K densities, along with cell media as control with total volume of 150 uL in each well. ~1.5 uL of 100 mM OX071 was added to the wells in rows 3-6 before the experiment.

The temperature probe was shielded and grounded. Cells were received at 11:36. The cells, in a multi-well apparatus, were placed inside an EPROI system (JIVA) at 11:44. The temperature reached 37° C. at 11:47 AM. The temperature during IRESE was ~38.5° C. Post IRESE (20 min) the temperature was around ~38.2-38.3° C.

JIVA-2S™ is a dedicated 25 mT preclinical EPROI instrument, which operates at 720 MHz radiofrequency.

The script paused at 12:20 to ensure sample was in the center of the resonator. The resonator itself shifted when adjusting heater interface. Imaging resumed 12:48 PM. Cells were removed at 1:44 PM. FIG. 18A shows the oxygen maps of the cells in the multi-well apparatus at the start, FIG. 18B shows the oxygen maps of the cells in the multi-well apparatus after about 1 hour, and FIG. 18C shows the oxygen maps of the cells in the multi-well apparatus after about 1.5 hours. Table 2 shows the pattern of the cells in the wells in the multi-cell apparatus.

TABLE 2

| Pattern in YZ | | | |
| --- | --- | --- | --- |
| M | 5K | 50K | M |
| 5K | 50K | M | 5K |
| 50K | M | 5K | 50K |

Figure 18D:
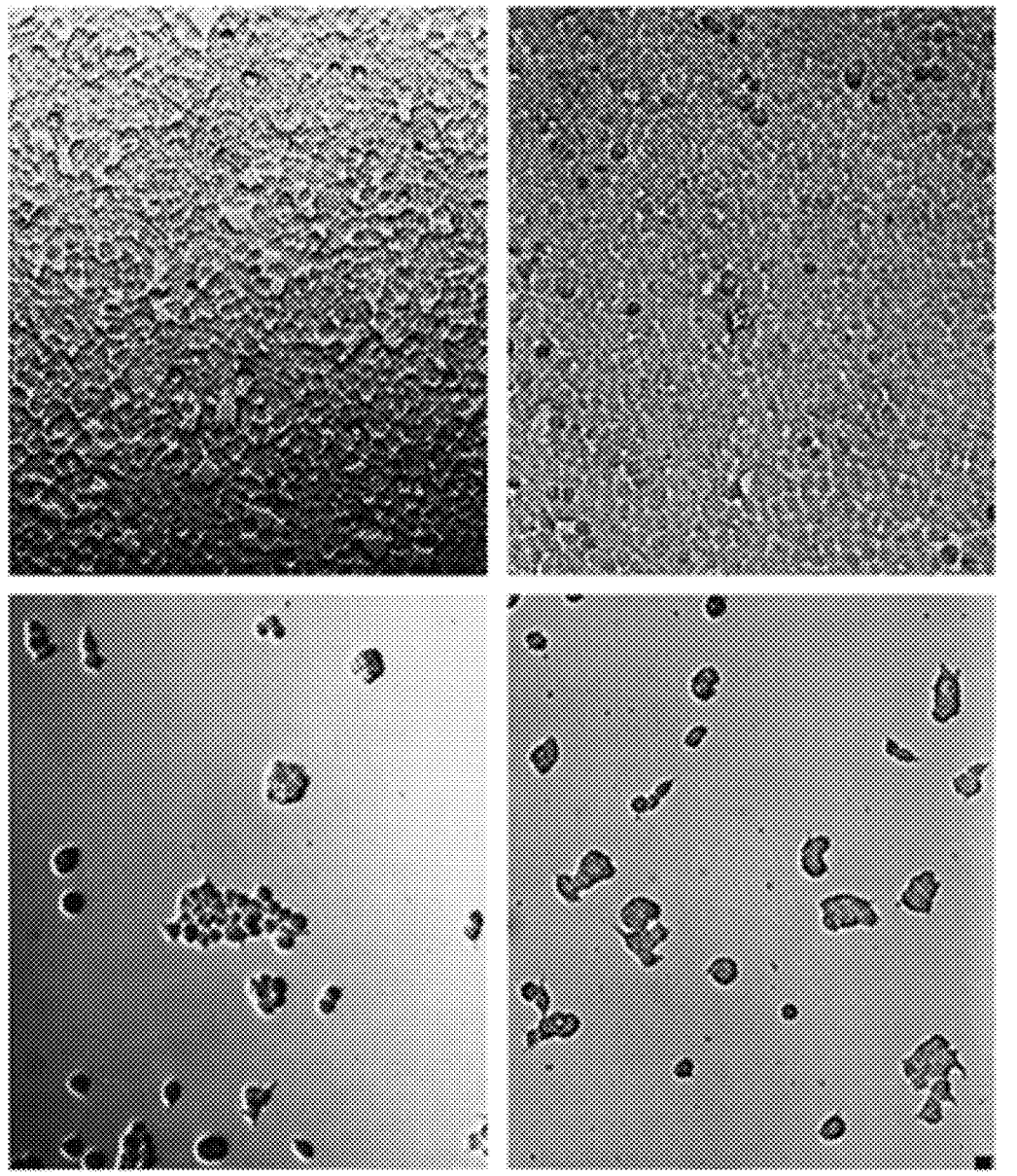
FIG. 18D are thermal images and microscopy showing the cells appeared normal.
Figure 18E:
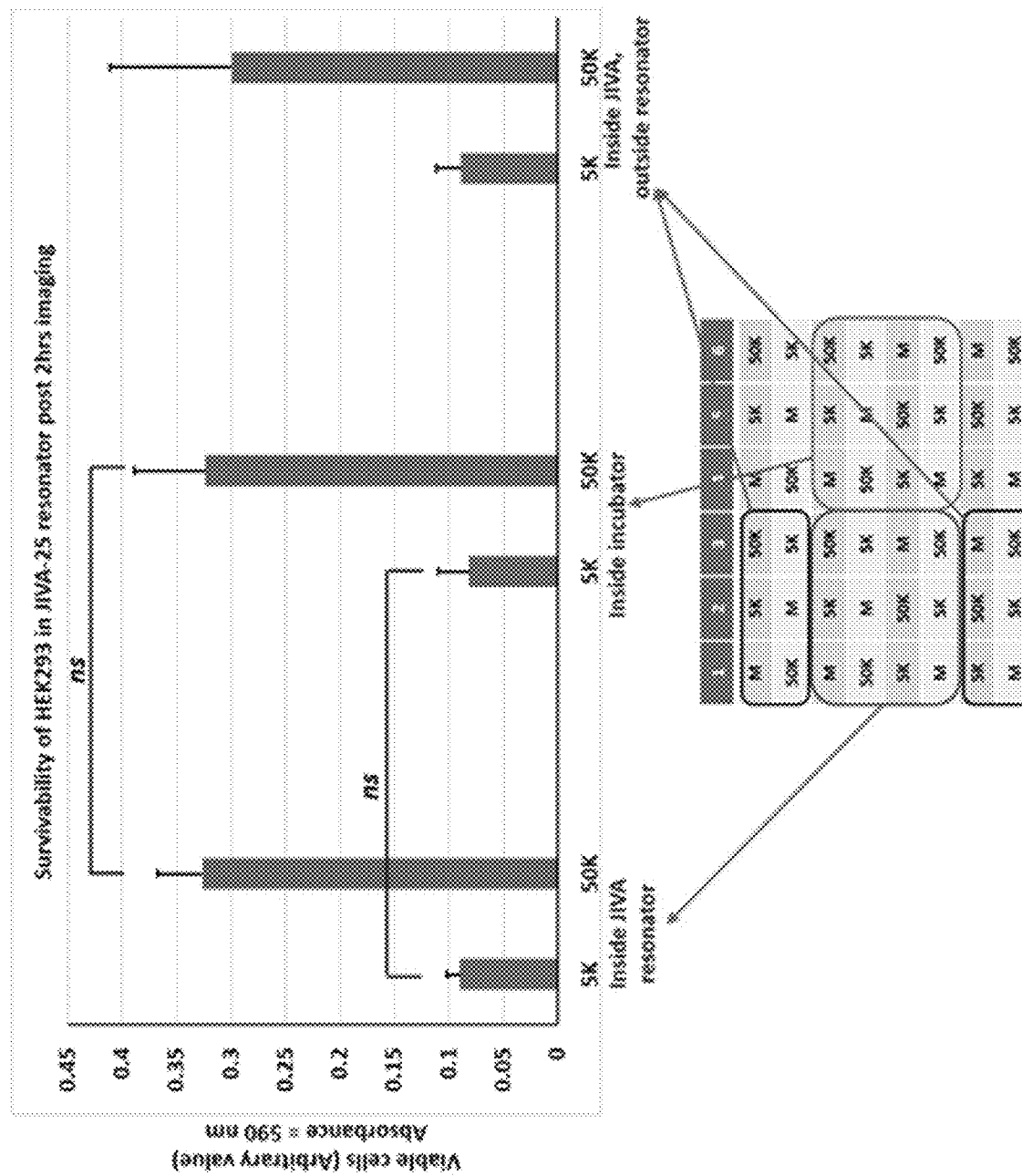
FIG. 18E shows survivability of the HEK293 cells in the resonator post 2 hours of imaging.

Thermal images and microscopy were taken and the cells appeared normal, as seen in FIG. 18D. FIG. 18E shows survivability of the HEK293 cells in the resonator post 2 hours of imaging. The cell viability assay indicates that the HEK293 cells were similarly viable in the resonator after 2 hours of imaging compared to the cells incubated inside a BOD incubator. No significant difference was observed in the cell viability based on the MTT assay.

The experiment was run multiple times, including having the cells in the multi-well apparatus and imaging system for up to 4 hours and up to 8 hours. The cell viability assay indicates that the HEK293 cells were similarly viable in the resonator after 4 hours and after 8 hours of imaging compared to the cells inside the BOD incubator. No significant difference was observed in the cell viability assay based on the MTT.

Figure 19A:
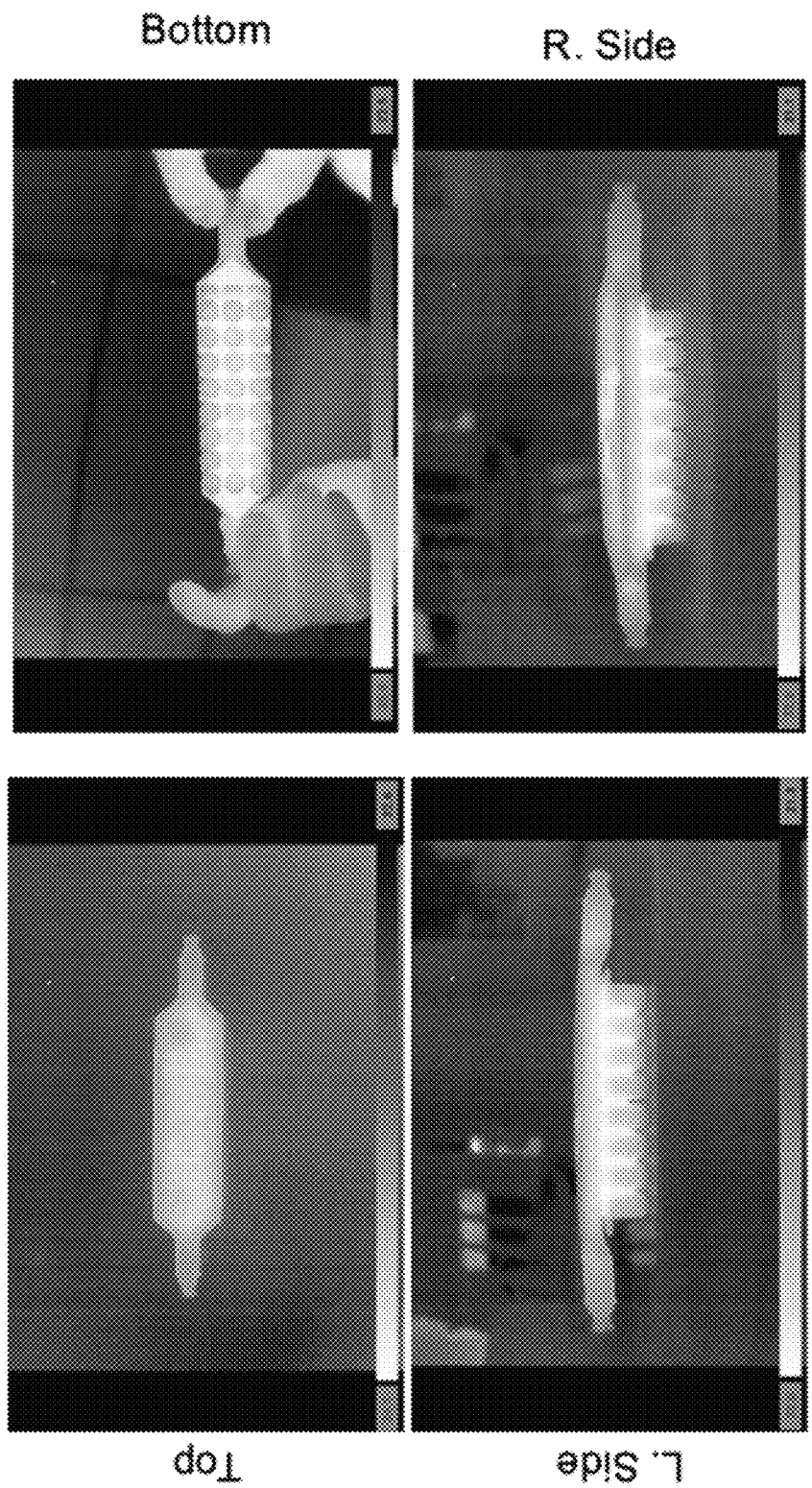
FIG. 19A shows thermal images of a multi-well apparatus cover showing even distribution of heat throughout the wells.
Figure 19B:
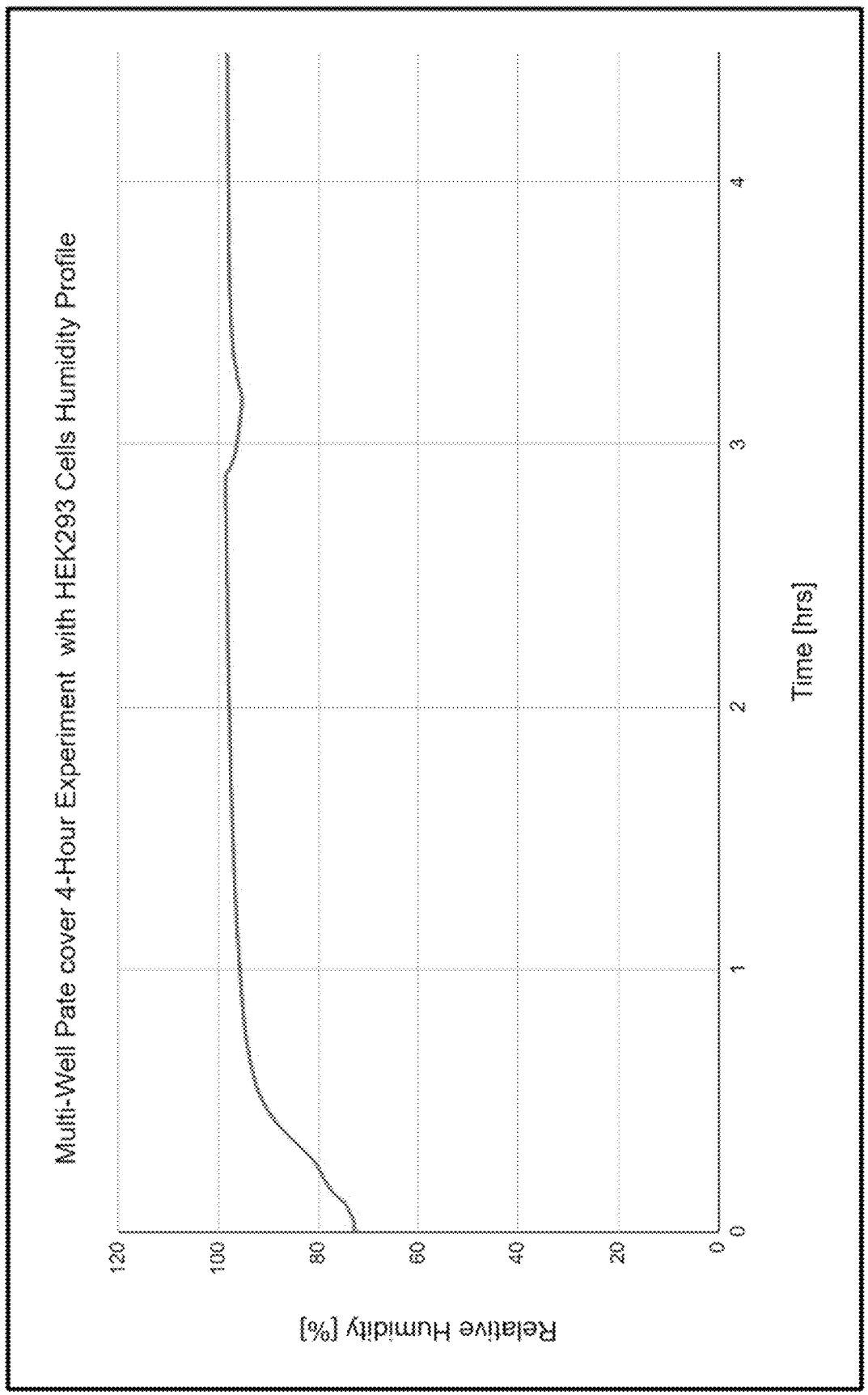
FIG. 19B shows a humidity profile of HEK293 cells inside multi-well apparatus during a 4-hour experiment, measured using the Adafruit AHT20 sensor.

FIG. 19A shows thermal images of a multi-well apparatus cover showing even distribution of heat throughout the wells. The feedback-driven temperature controller maintained the sample temperature at 37° C.±1° C. as required by mammalian cells. FIG. 19B shows a humidity profile of HEK293 cells inside multi-well apparatus during a 4-hour experiment, measured using the Adafruit AHT20 sensor. The system reached 100% relative humidity and remained constant throughout the experiment.

Example 7

Figure 20A:
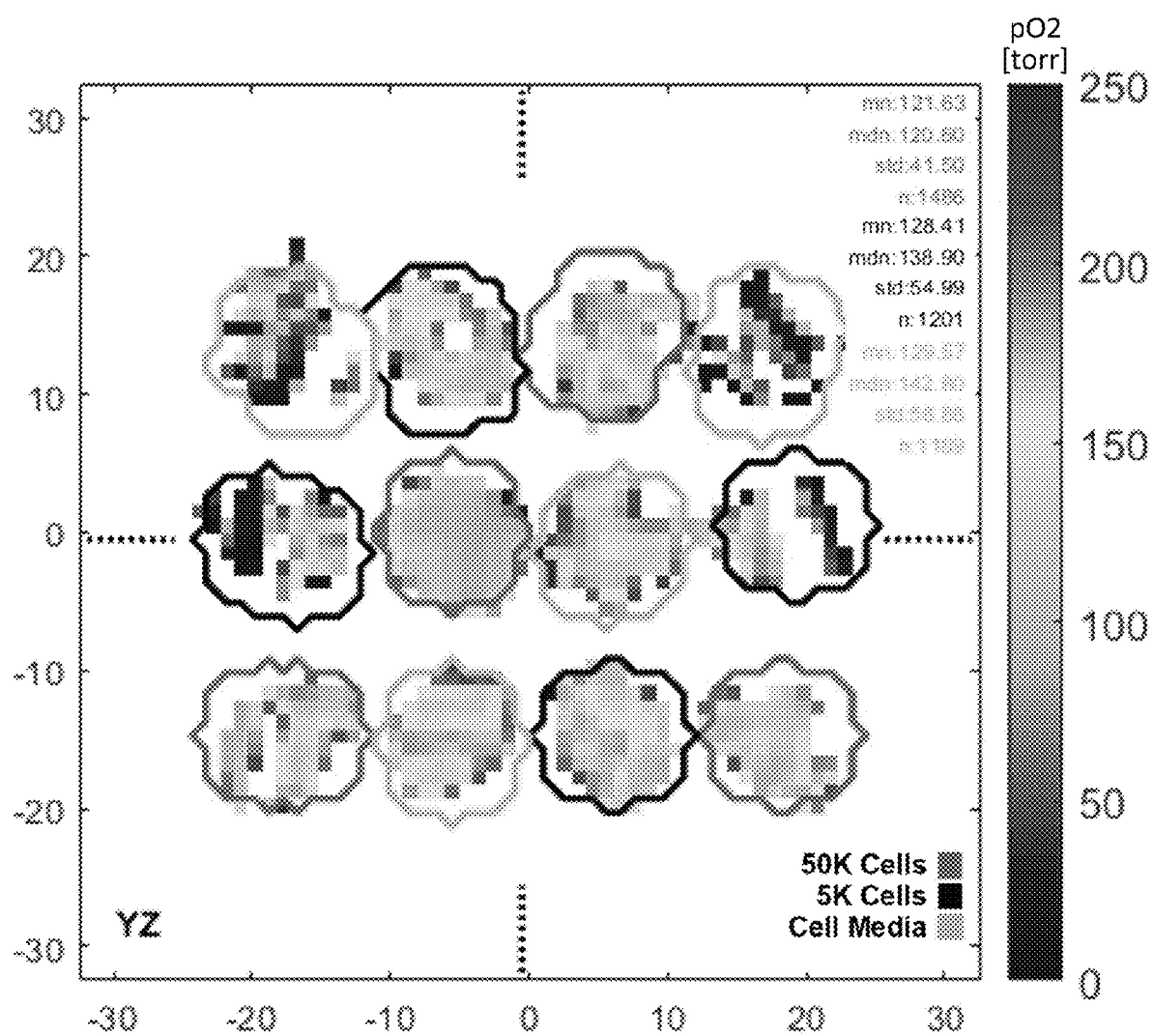
FIG. 20A shows a two-hour experiment with dead HEK293 cells carried out with the same experimental conditions.
Figure 20B:
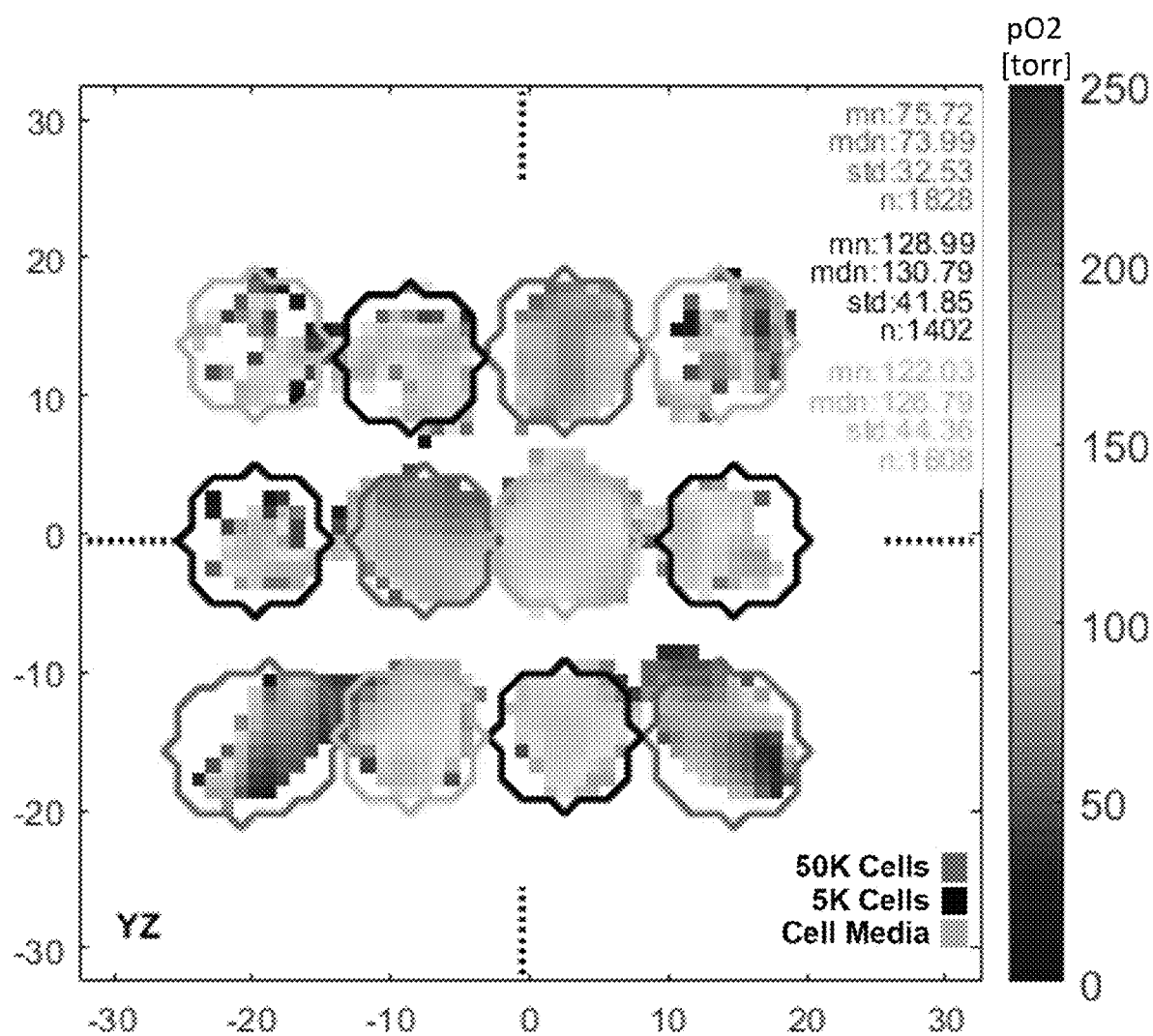
FIG. 20B shows a pO2 map of HEK293 (density 50K and 5K) cells with cell media as control measured during a 24-hour experiment.
Figure 20C:
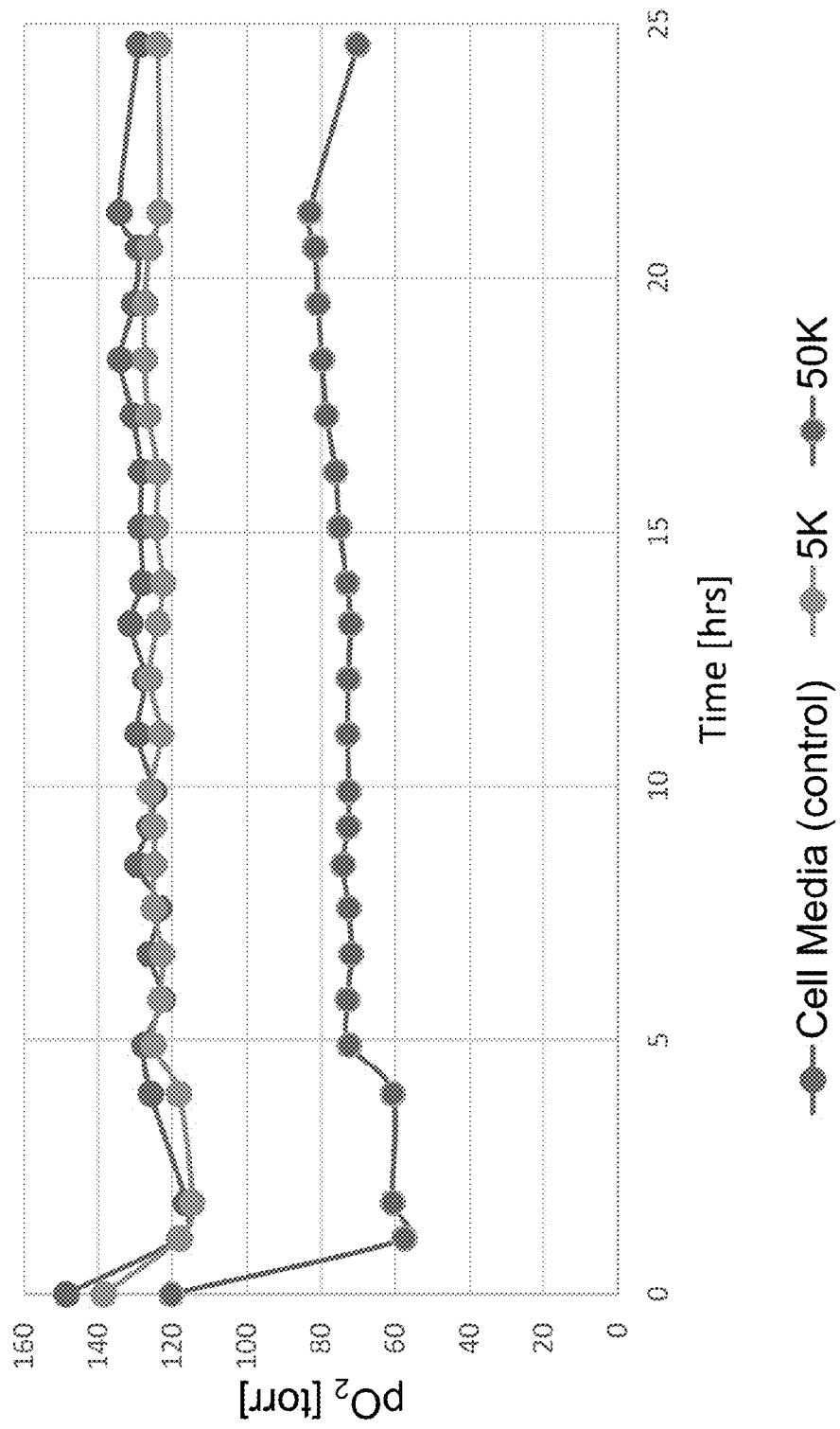
FIG. 20C shows pO2 [torr] as a function of time [hours] in one example.
Figure 20D:
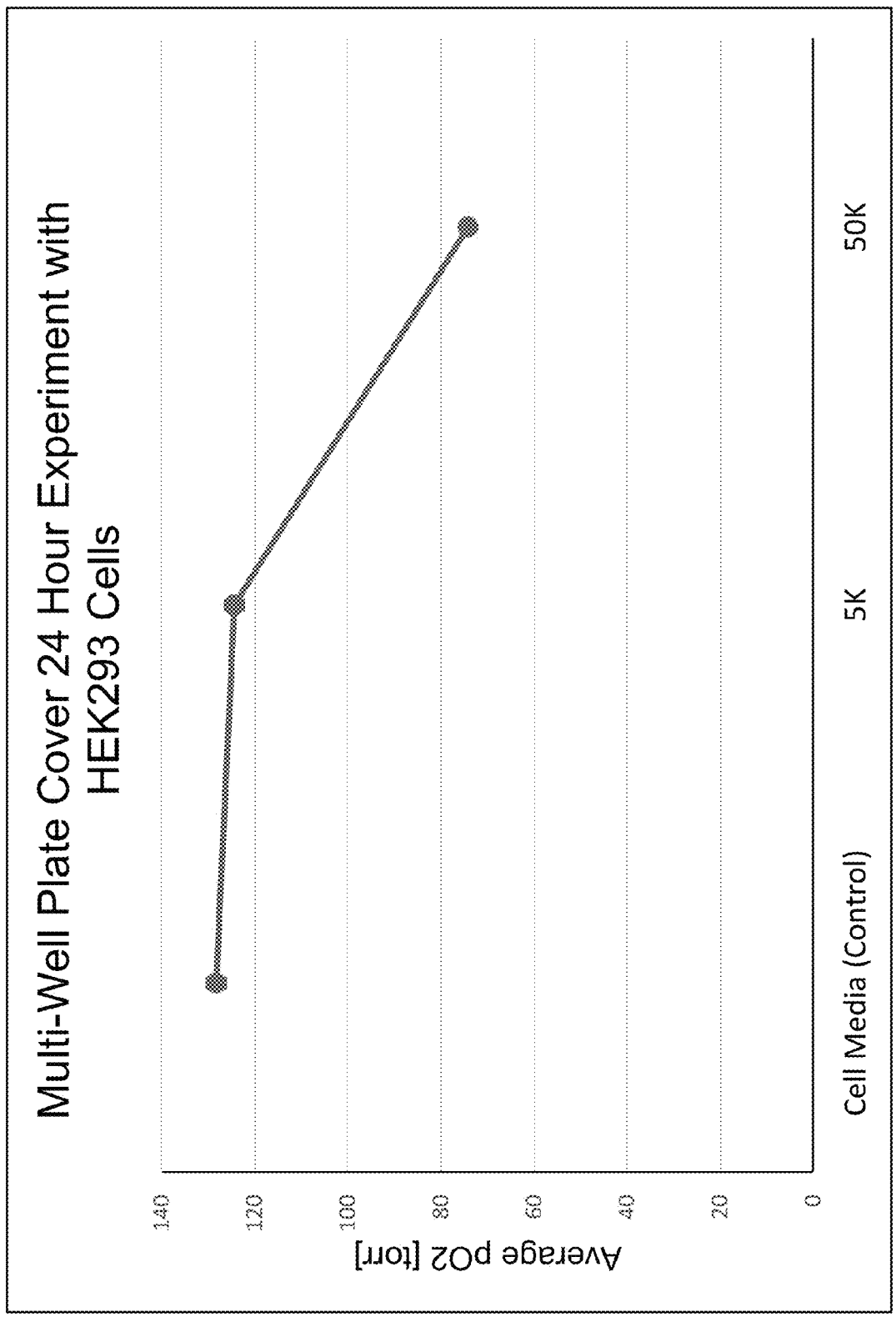
FIG. 20D shows pO2 [torr] vs Cell Density in one example.
Figure 20E:
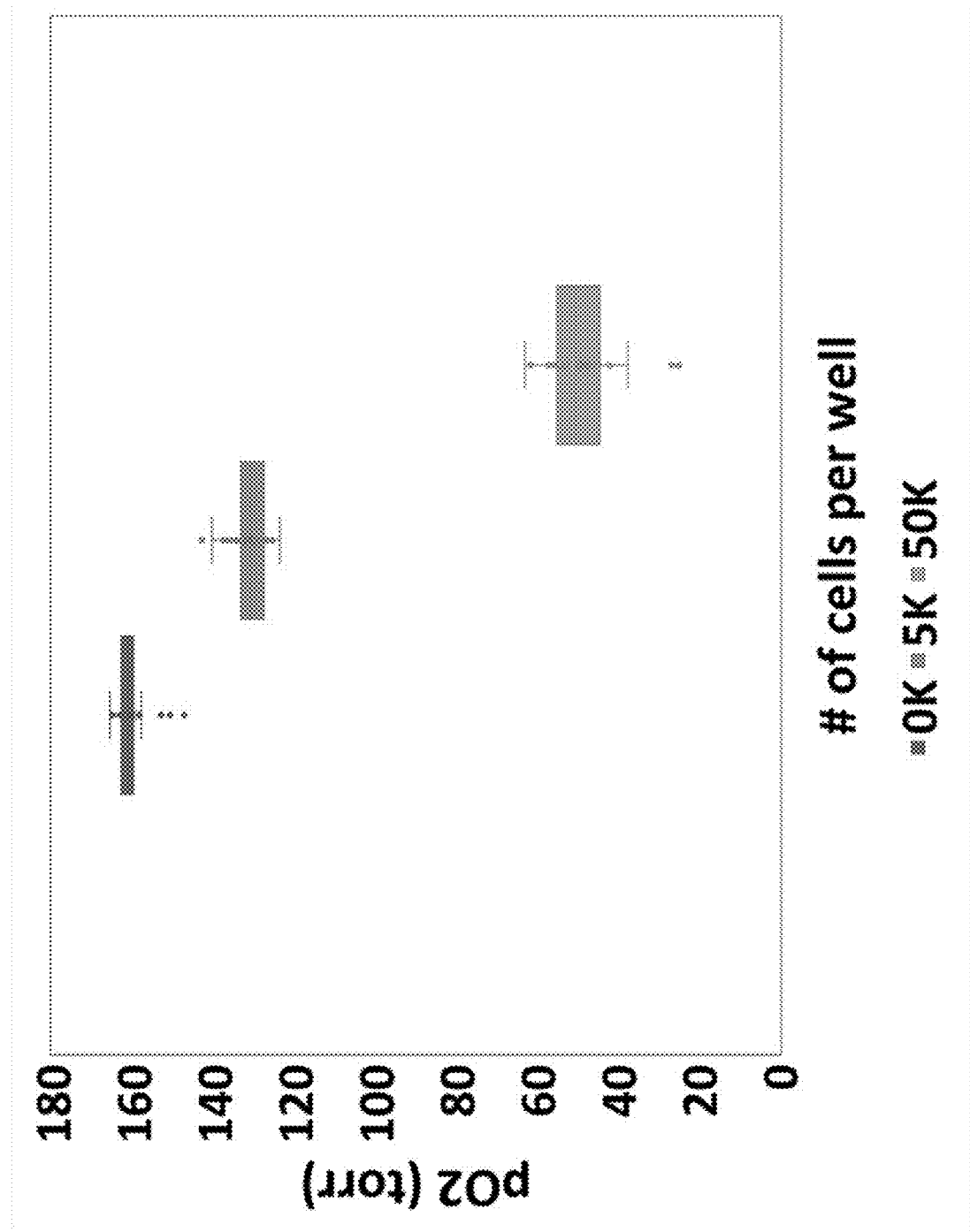
FIG. 20E shows pO2 [torr] vs Cell Density in one example.
Figure 20F:
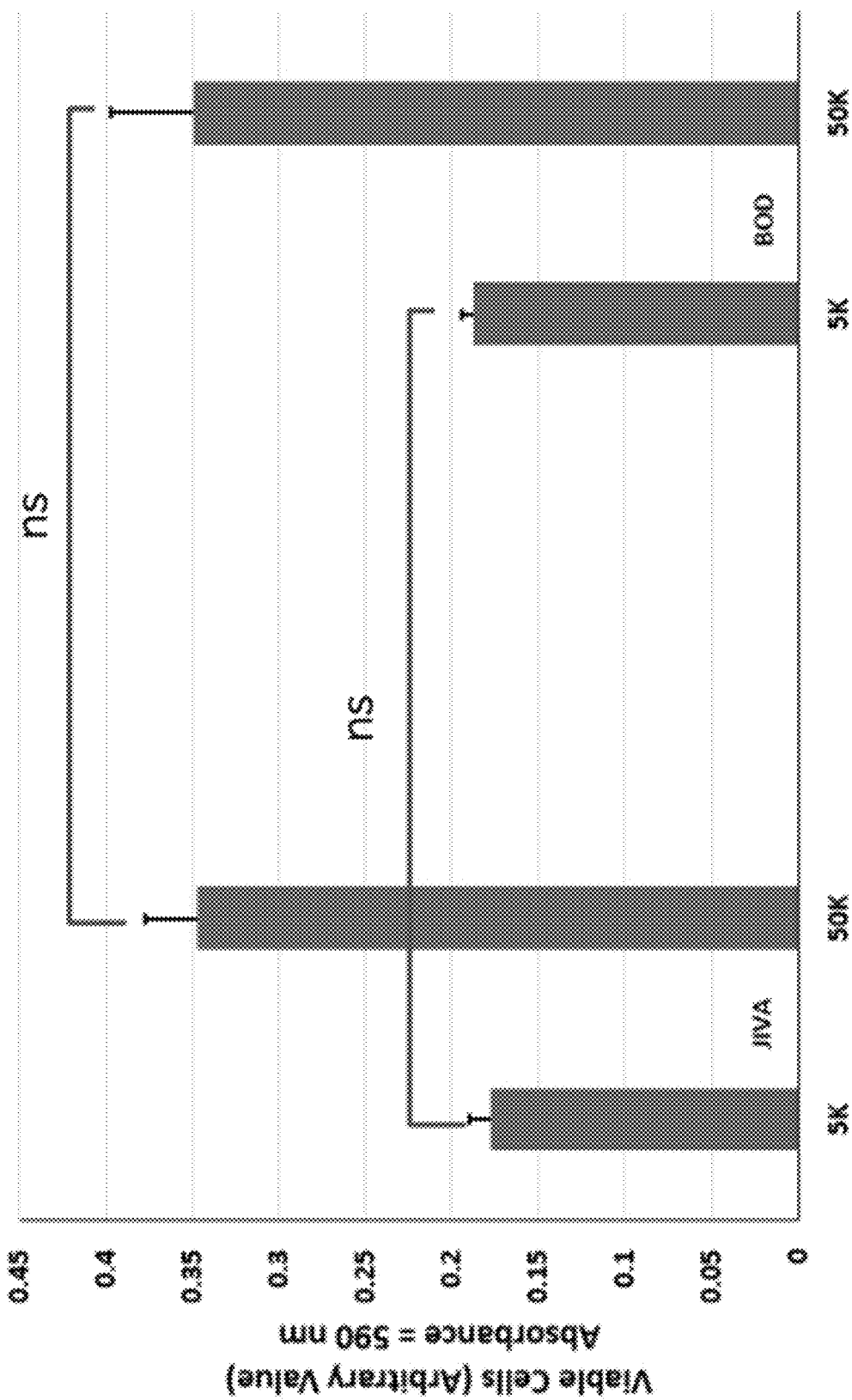
FIG. 20F shows viable cells vs cell density in one example.

FIG. 20B shows a two-hour experiment with dead HEK293 cells was carried out with a cell viability system with a multi-well apparatus and 38 mm resonator. FIGS. 20B-20F show results of a 24 hour experiment of a cell viability system with a multi-well apparatus and 38 mm resonator. FIG. 20B shows a pO2 map of HEK293 (density 50K and 5K) cells with cell media as control measured during a 24-hour experiment. HEK293 cells with 50K seeding density showed lower average pO2, 75.72 mmHg, compared to wells containing 5K cells. Wells showed similar mean pO2 [torr] in all wells, indicating that cells are not respiring and consuming oxygen. FIG. 20C shows pO2 [torr] as a function of time [hours]. Higher metabolic activity in wells seeded with 50K cells showed higher oxygen consumption, and therefore, lower pO2 (green line) compared to lower cell density and cell media. FIG. 20D shows pO2 [torr] vs Cell Density. Higher metabolic activity in wells seeded with 50K cells showed higher oxygen consumption, and therefore, lower pO2 compared to lower cell density and cell media. Control 128.31±1.55, 5K 124.41±1.58, and 50K 74.95±0.97 torr.

Example 8

Figure 21A:
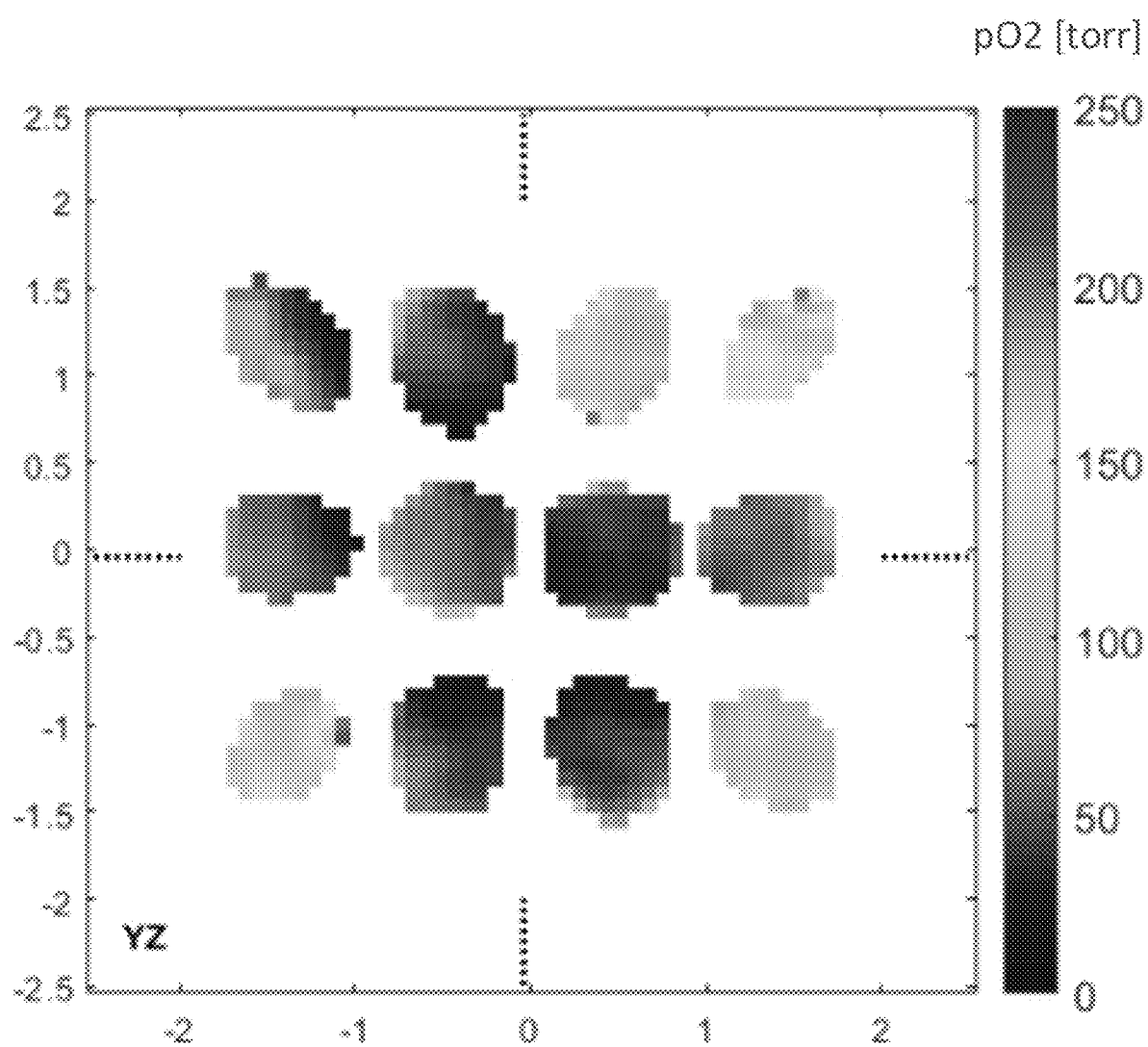
FIG. 21A shows a $pO_2$ map of HEK293 cells at 6 densities (densities 10K, 25K, 50K, 75K, and 100K) with cell media as control.
Figure 21B:
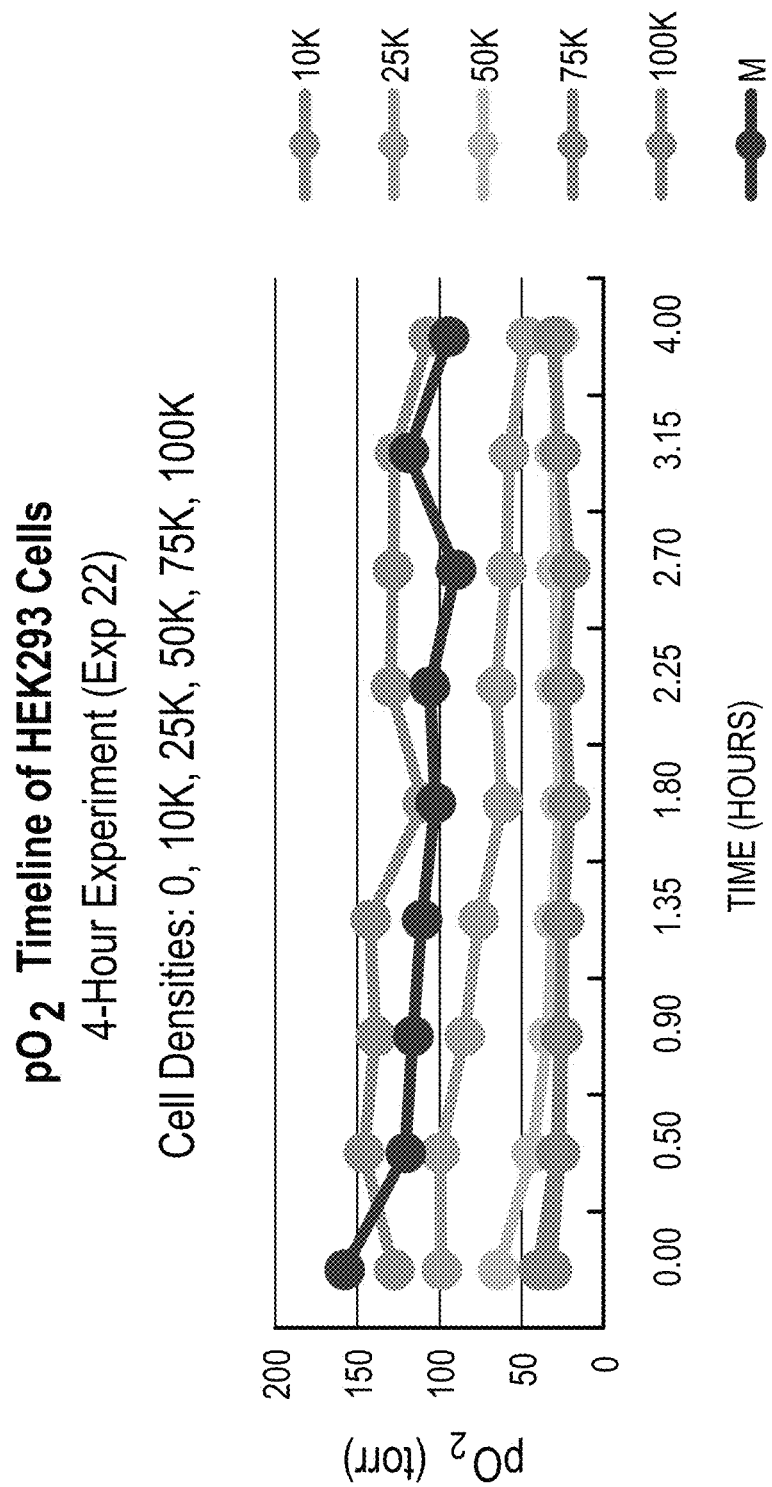
FIG. 21B shows a $pO_2$ timeline of the HEK293 cells.
Figure 21C:
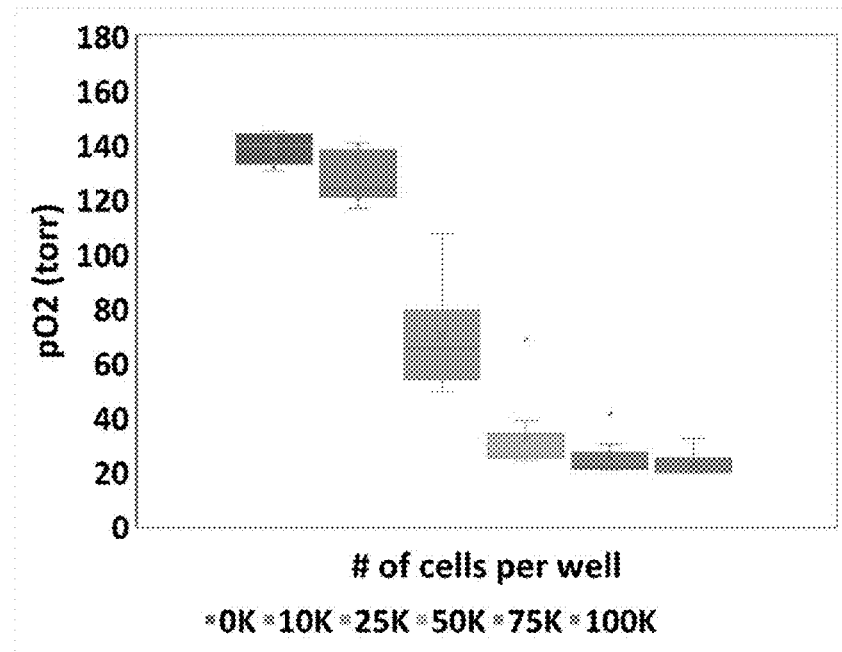
FIG. 21C shows pO2 values at 6 densities in an example.
Figure 21D:
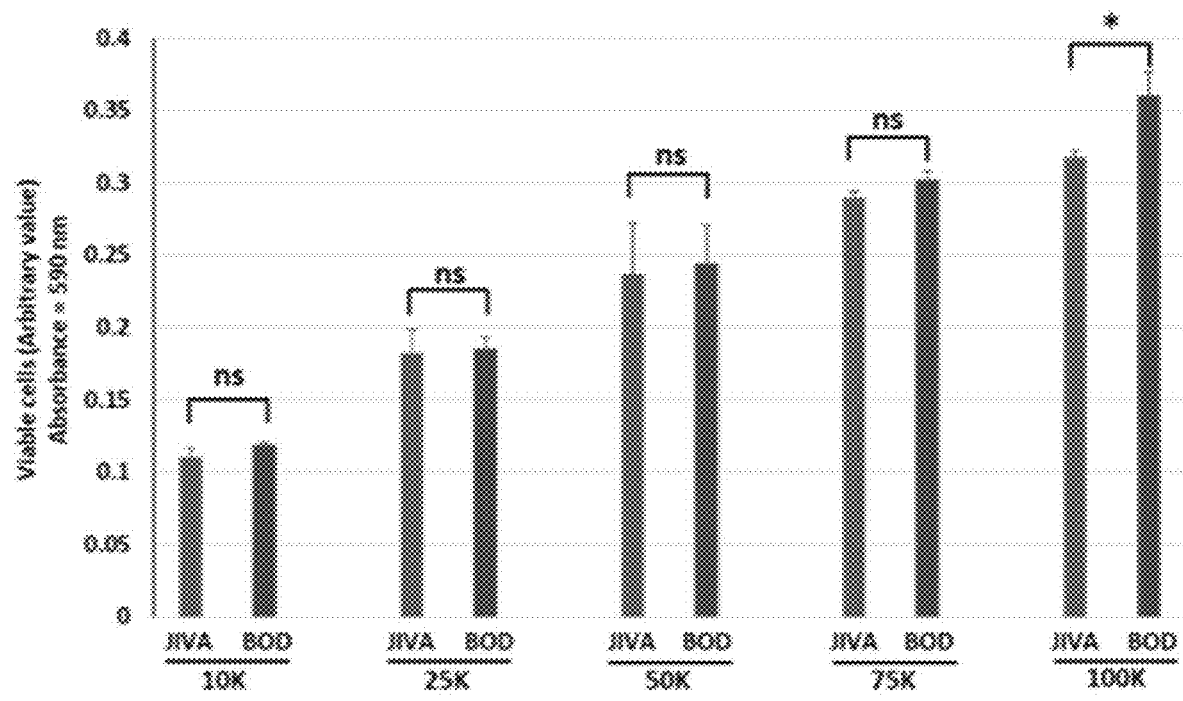
FIG. 21D shows cell viability of the 5 cell densities (no control) comparing in the EPROI system and in an incubator in an example.

Multiple cell densities were imaged a cell viability system with a multi-well apparatus and 42 mm resonator for 4 hours, with 95% air and 5% $CO_2$ gas mixture delivered at 3.75 ccm, and constant temperature maintained at 37° C. For example, FIG. 21A shows a pO$_2$ map of HEK293 cells at 6 densities (densities 0, 10K, 25K, 50K, 75K, and 100K) with cell media as control and FIG. 21B shows a pO$_2$ timeline of the HEK293 cells. FIG. 21C shows pO2 values at 6 densities and FIG. 21D shows cell viability of the 5 cell densities (no control) comparing in the EPROI system and in an incubator. Table 3 shows the pattern of the cell densities in the multi-well apparatus in YZ.

TABLE 3

| Pattern in YZ | | | |
|---|---|---|---|
| 100K | 50K | 10K | M |
| 75K | 25K | 75K | 25K |
| M | 100K | 50K | 10K |

Figure 21E:
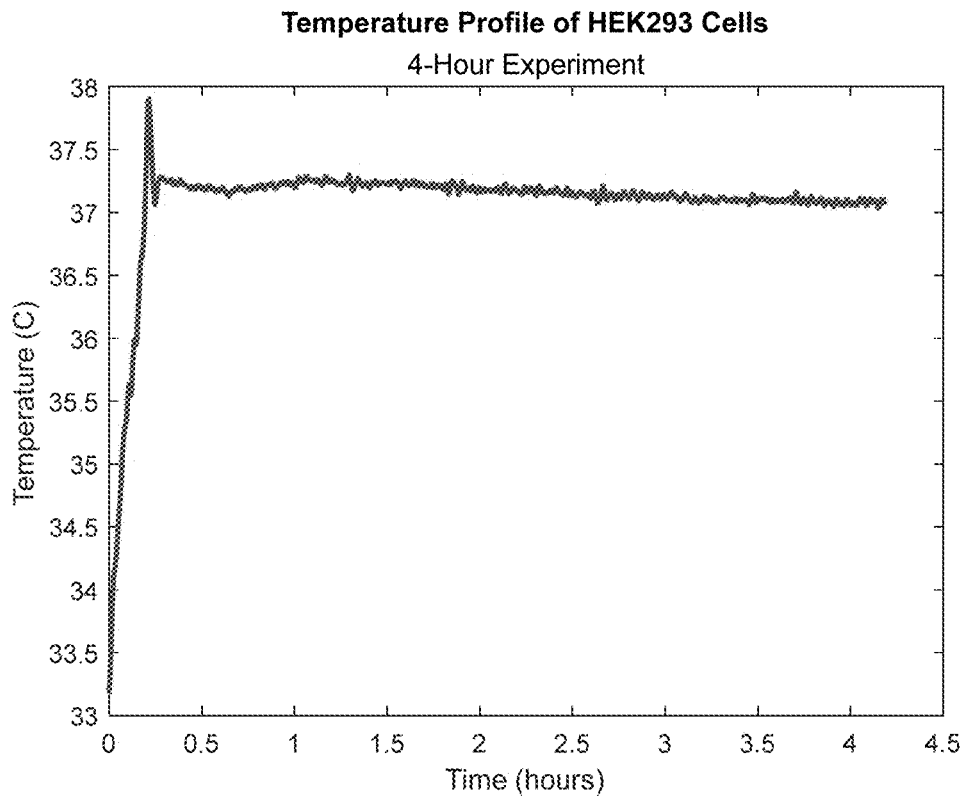
FIG. 21E shows an example temperature profile of a multi-well apparatus cover during a 4-hour experiment.
Figure 21F:
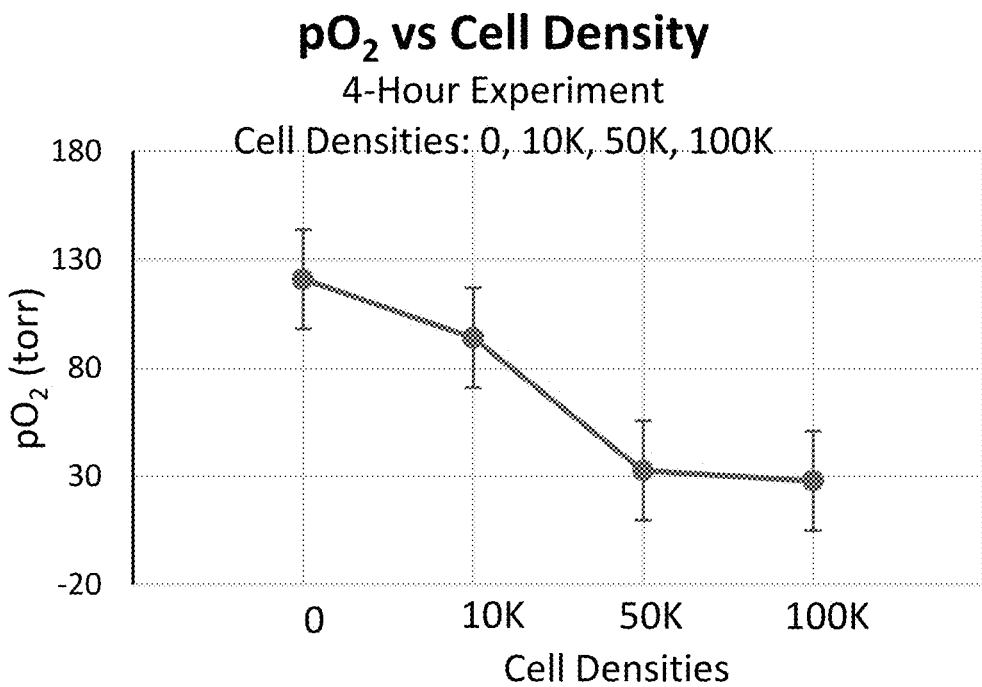
FIG. 21F shows an example pO2 [torr] vs Cell Density.
Figure 21G:
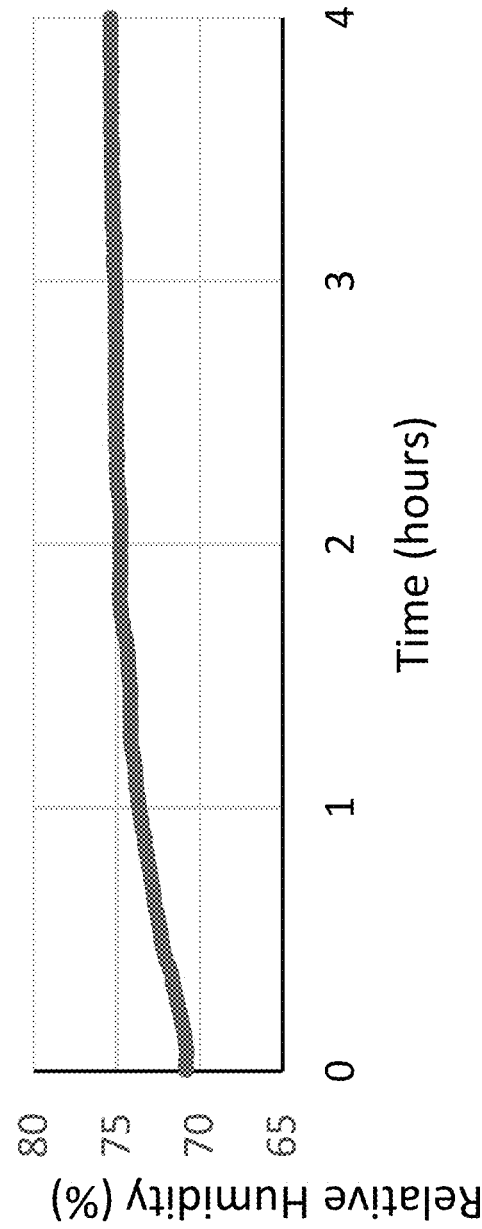
FIG. 21G shows an example relative humidity profile of HEK293 cells.

FIG. 21E shows an example temperature profile of a multi-well apparatus cover during a 4-hour experiment. FIG. 21F shows an example pO2 [torr] vs Cell Density. pO$_2$ was measured over a 4-hour period with 95% air and 5% $CO_2$ mixture delivered to cells at a flow rate of 3.75 ccm, and a constant temperature of 37° C. Higher metabolic activity in wells seeded with 50-100K HEK293 cells showed higher oxygen consumption, and therefore, lower pO2 compared to lower cell density and cell media. Control 121.02±2.78, 10K 93.872±2.69, 50K 32.63±2.77 torr, and 100K 27.84±2.95. FIG. 21G shows an example relative humidity profile of HEK293 cells. Delivering the 95% air and 5% $CO_2$ gas mixture required by cells at a total flow rate of 3.75 sccm prevents excess condensation inside the wells and allows the pH to remain constant.

Table 4 shows a pH comparison of cell media and cells at various densities between the cell viability system and a lab cell culture incubator.

TABLE 4

| pH comparison | | |
|---|---|---|
| | Multi-well Plate Incubator (pH) | BOD Cell Culture Incubator (pH) |
| Media | 8.18 | 8.18 |
| 10K | 8.14 | 8.13 |
| 25K | 8.09 | 8.10 |
| 50K | 8.06 | 8.07 |
| 75K | 7.99 | 8.01 |
| 100K | 7.89 | 7.91 |

Figures 21H, 21I:
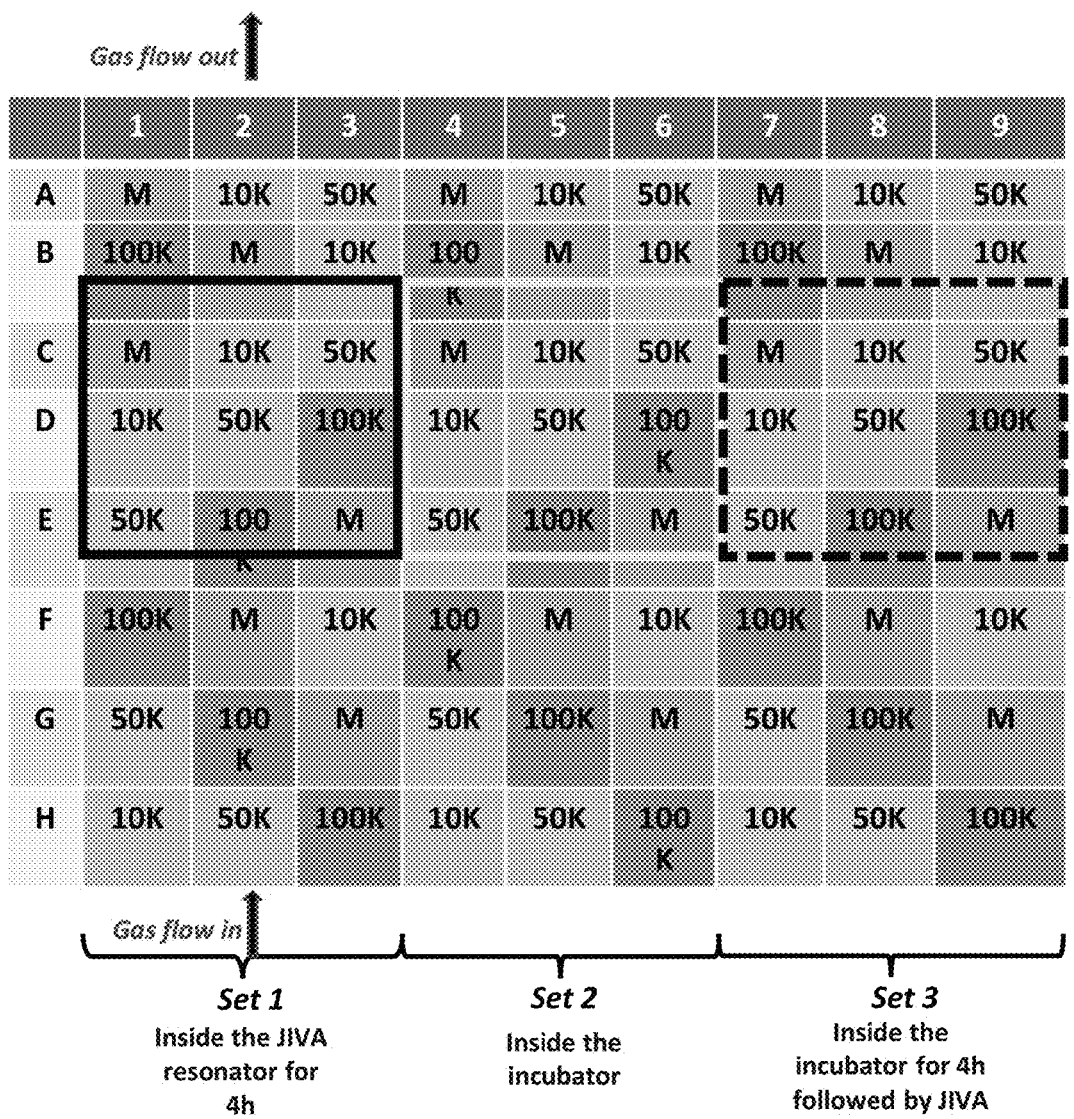
FIG. 21H shows example placement for cell density based EPR Oxygen Imaging of HEK293 cells at 10K, 50K, and 100K.
FIG. 21I shows cell viability results of FIG. 21F.

FIG. 21H shows example placement for cell density based EPR Oxygen Imaging of HEK293 cells at 10K, 50K, and 100K. FIG. 21I shows cell viability results of FIG. 21F.

Figure 21J:
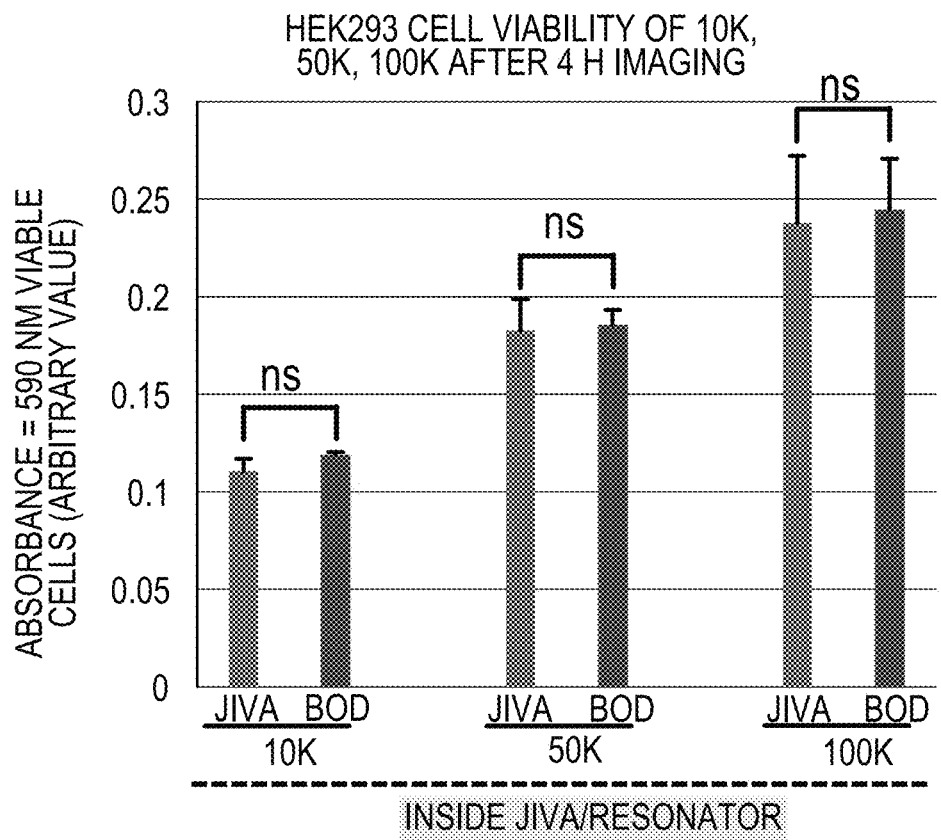
FIG. 21J shows cells plated in four densities in the cell viability system imaged with an EPROI system (JIVA).
Figure 21K:
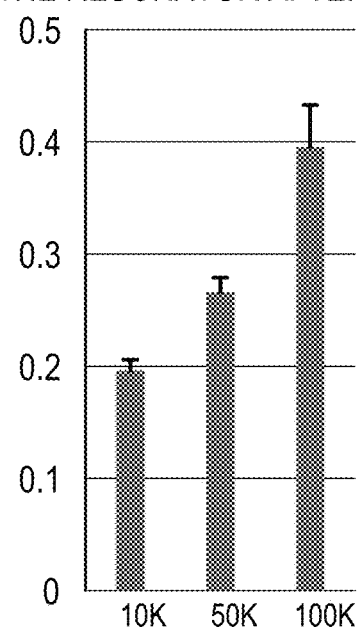
FIG. 21K shows cells remaining in an incubator (BOD incubator).
Figure 21L:
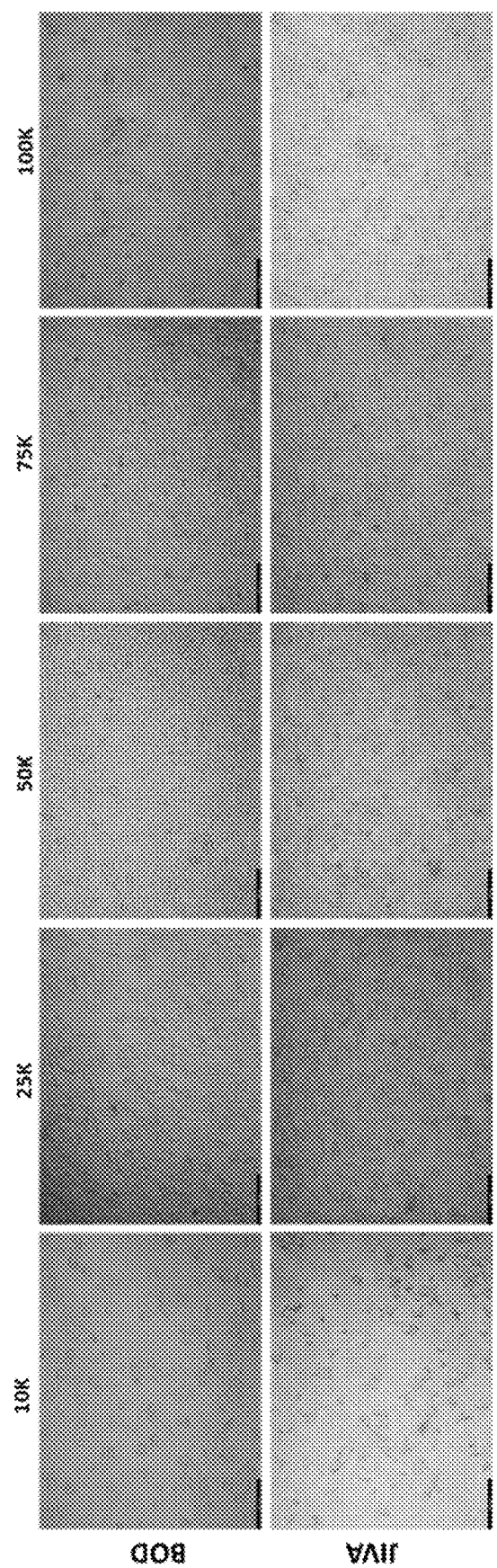
FIG. 21L shows a comparison of cell morphology in the cell viability system and BOD incubator 4 hours after the imaging.

FIGS. 21J and 21K show a comparison between cells plated in four densities in the cell viability system imaged with an EPROI system (JIVA) and cells remaining in an incubator (BOD incubator). MTT assay data showed that HEK293 cells were equally viable at 10K, 25K, 50K and 75K. No significant difference was found. Cells at 100K density were more viable in the BOD compared to JIVA. Cells outside the resonator but inside JIVA (green columns) were also equally viable as inside the resonator. FIG. 21L shows a comparison of cell morphology in the cell viability system and BOD incubator 4 hours after the imaging.

Example 9

Figure 22A:
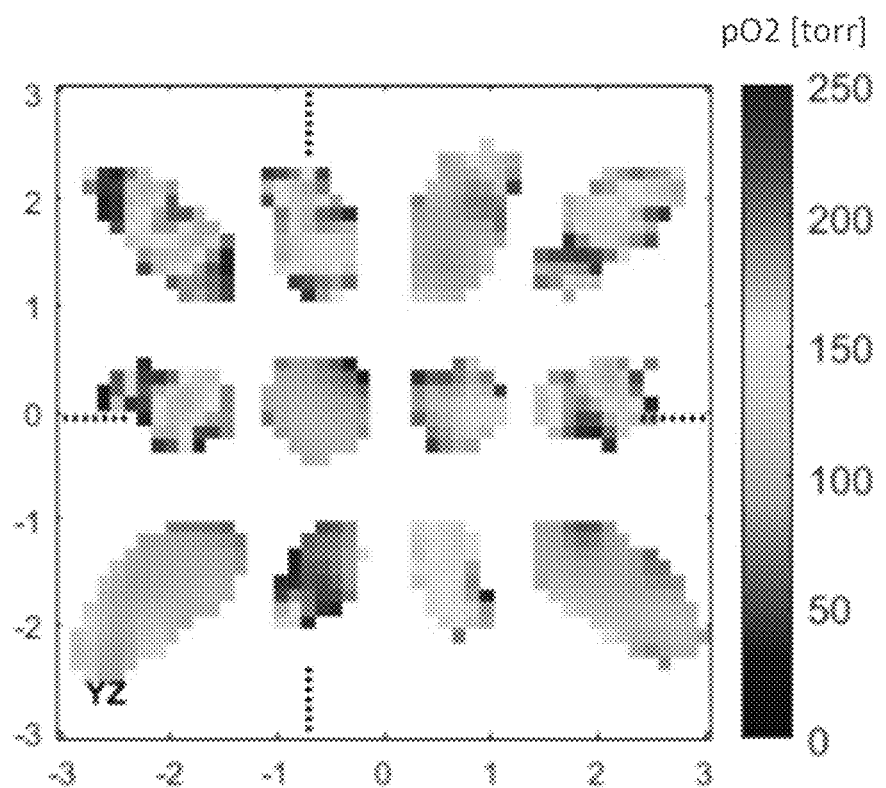
FIG. 22A shows a pO2 map of Jurkat cells (densities 5K and 50K) with cell media as control.
Figure 22B:
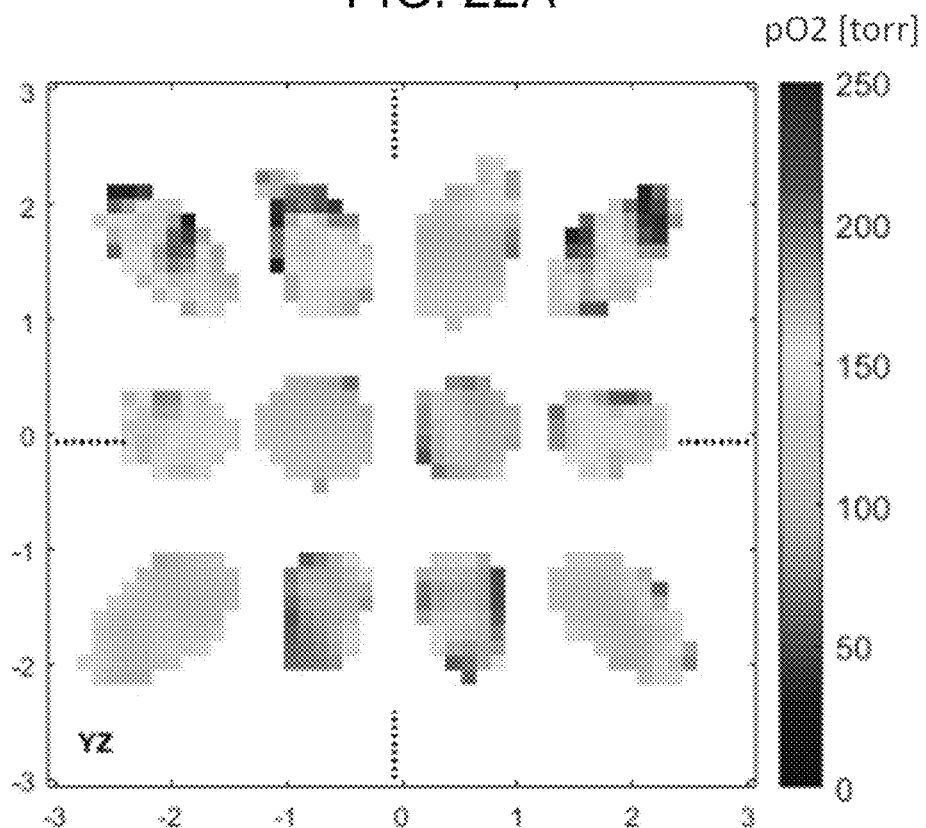
FIG. 22B shows a $pO_2$ map of cells immediately after removing from the BOD cell culture incubator.
Figure 22C:
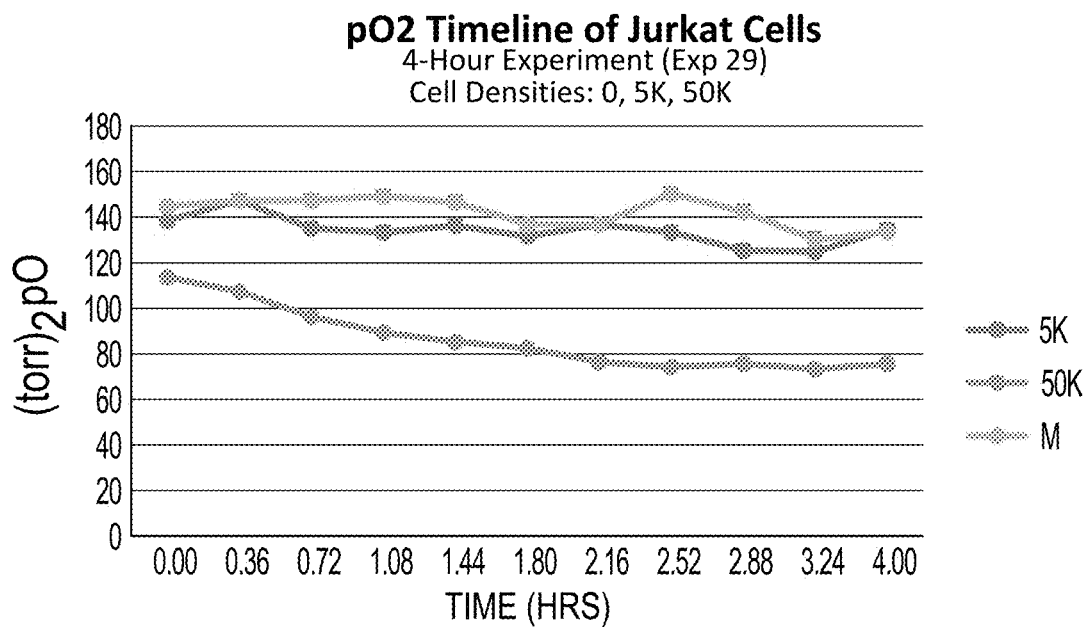
FIG. 22C shows a $pO_2$ timeline of the Jurkat cells.

Multiple cell densities were imaged a cell viability system with a multi-well apparatus and 42 mm resonator for 4 hours, with a constant 95% air and 5% $CO_2$ gas mixture delivered at 3.75 ccm, and constant temperature maintained at 37° C. FIG. 22A shows a pO$_2$ map of Jurkat cells (densities 5K and 50K) with cell media as control and FIG. 22B shows a pO$_2$ map of cells immediately after removing from the BOD cell culture incubator. Trityl (1 mM) was added to each well before imaging. Both pO2 maps show a distinct difference in media, 5K, and 50K cell densities. Higher metabolic activity in wells seeded with 50K Jurkat cells showed higher oxygen consumption, and therefore, lower pO2 compared to lower cell density and cell media. FIG. 22C shows a pO$_2$ timeline of the Jurkat cells. Table 5 shows the pattern of the cell densities in the multi-well apparatus in YZ.

TABLE 5

| Pattern in YZ | | | |
|---|---|---|---|
| M | 5K | 50K | M |
| 5K | 50K | M | 5K |
| 50K | M | 5K | 50K |

Figure 22D:
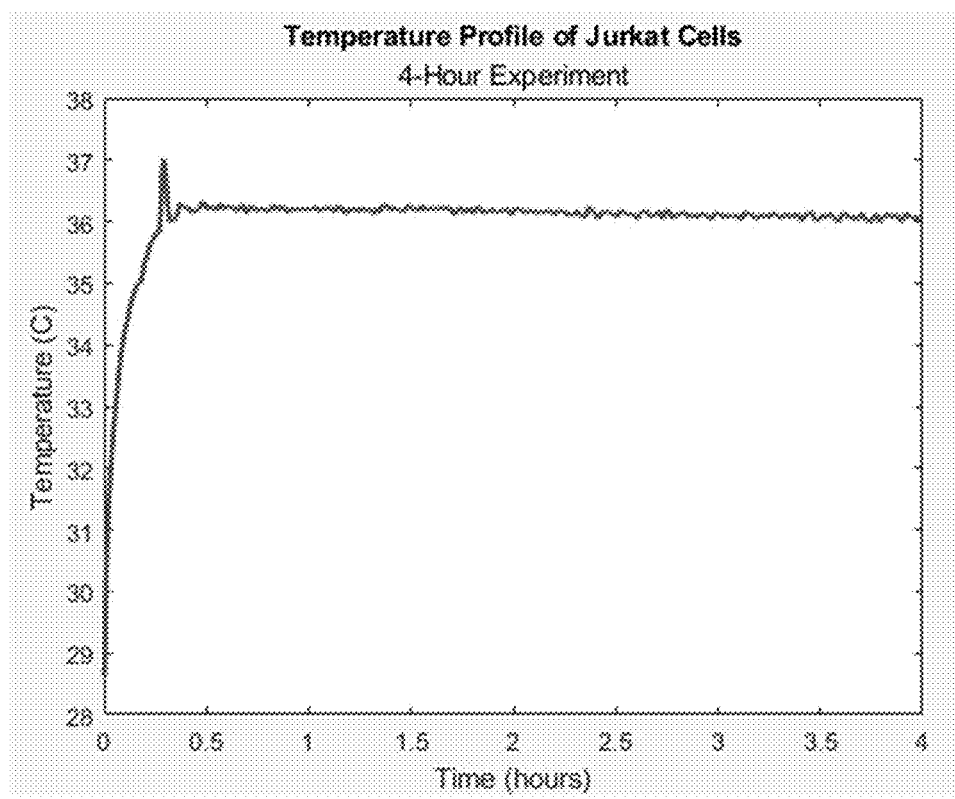
FIG. 22D is a temperature profile of a multi-well apparatus during a 4-hour experiment with Jurkat cells.

FIG. 22D is a temperature profile of a multi-well apparatus during a 4-hour experiment with Jurkat cells. The integrated heat system used feedback from the temperature probe placed on the multi-well plate cover to maintain 37° C. required by cells. Table 6 shows a pH comparison of cell media and Jurkat cells at 0, 5K and 50K densities between the multi-well apparatus (95% air, 5% $CO_2$ delivered at 3.75 ccm, 37° C.) and lab cell culture incubator.

TABLE 6 pH comparison

| | Multi-well Plate Incubator (pH) | BOD Cell Culture Incubator (pH) |
|---|---|---|
| Media | 8.01 | 7.97 |
| 5K | 7.93 | 7.97 |
| 50K | 7.80 | 7.87 |

Figure 22E:
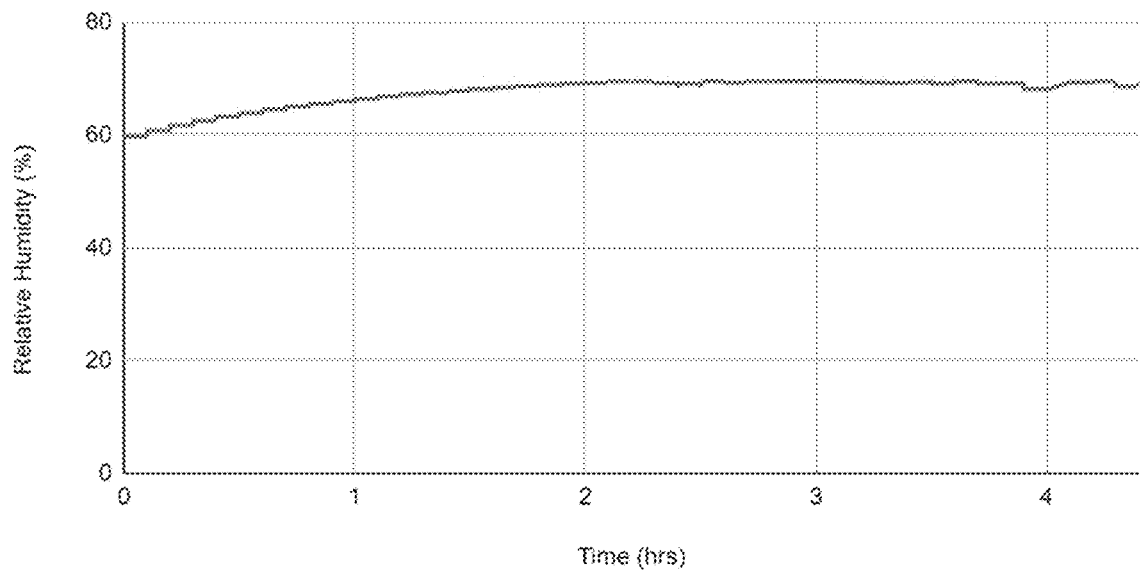
FIG. 22E shows relative humidity (%) measured at the outlet of the multi-well apparatus cover.
Figure 22F:
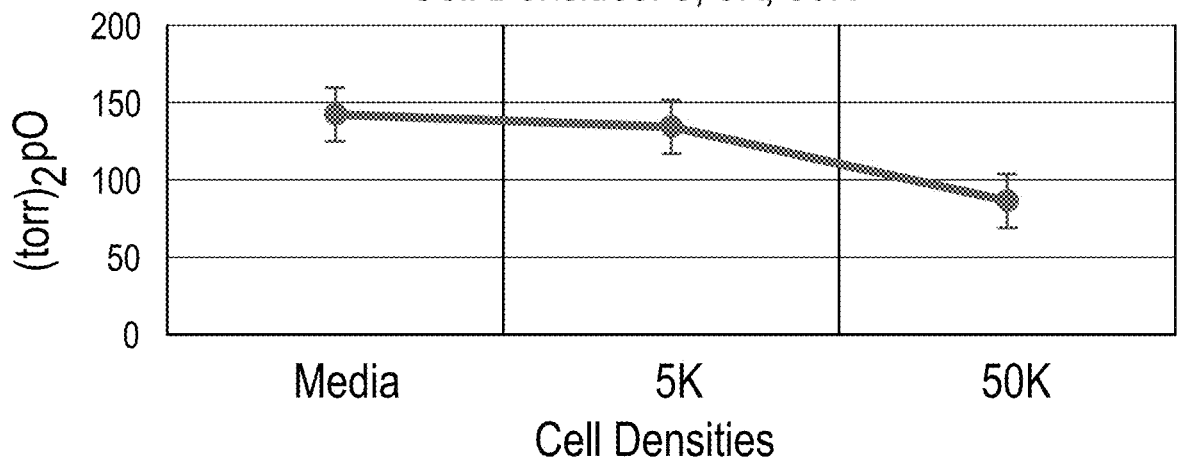
FIG. 22F shows pO2 [torr] vs Cell Density of the Jurkat cells.
Figure 22G:
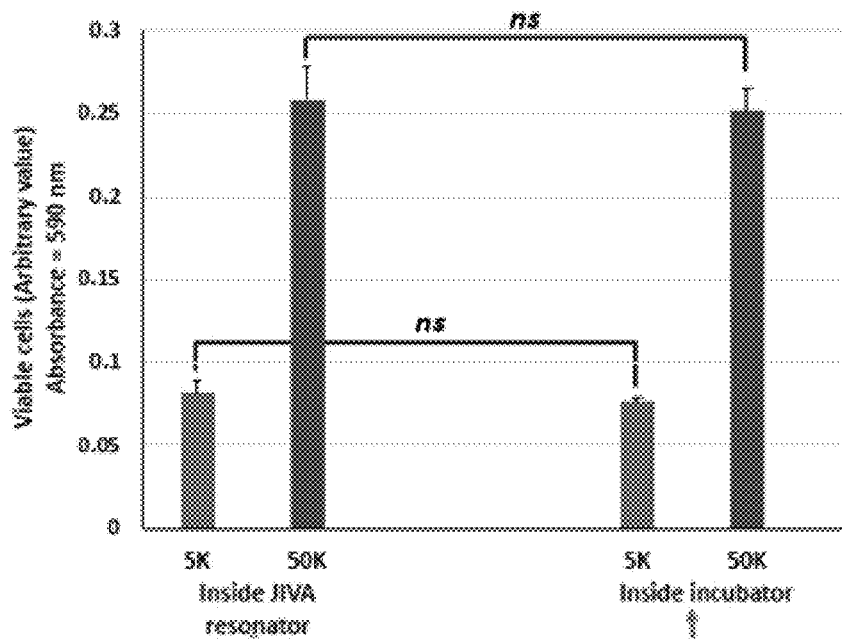
FIG. 22G shows cell viability after 4 hours using MTT in the system and in an incubator.
Figure 22H:
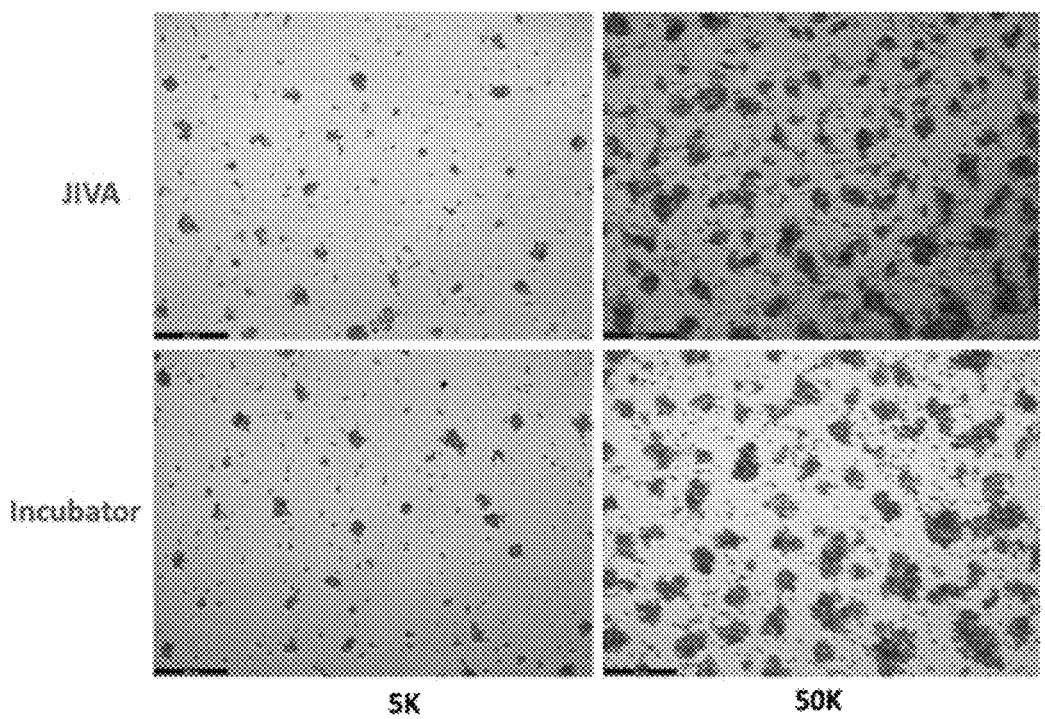
FIG. 22H shows the cell morphology of cells after 4 hours of imaging in the system or in an incubator.

FIG. 22E shows relative humidity (%) measured at the outlet of the multi-well apparatus cover. Delivering the 95% air and 5% $CO_2$ gas mixture required by cells at a total flow rate of 3.75 sccm prevents excess condensation inside the wells and allows the pH to remain constant. FIG. 22F shows pO2 [torr] vs Cell Density of the Jurkat cells.

Example 10

Figure 23A:
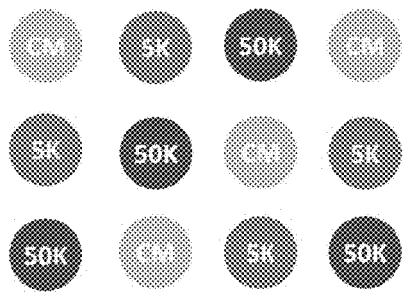
FIG. 23A shows the cell density placement for the cell viability assessment of FIG. 23B.
Figure 23B:
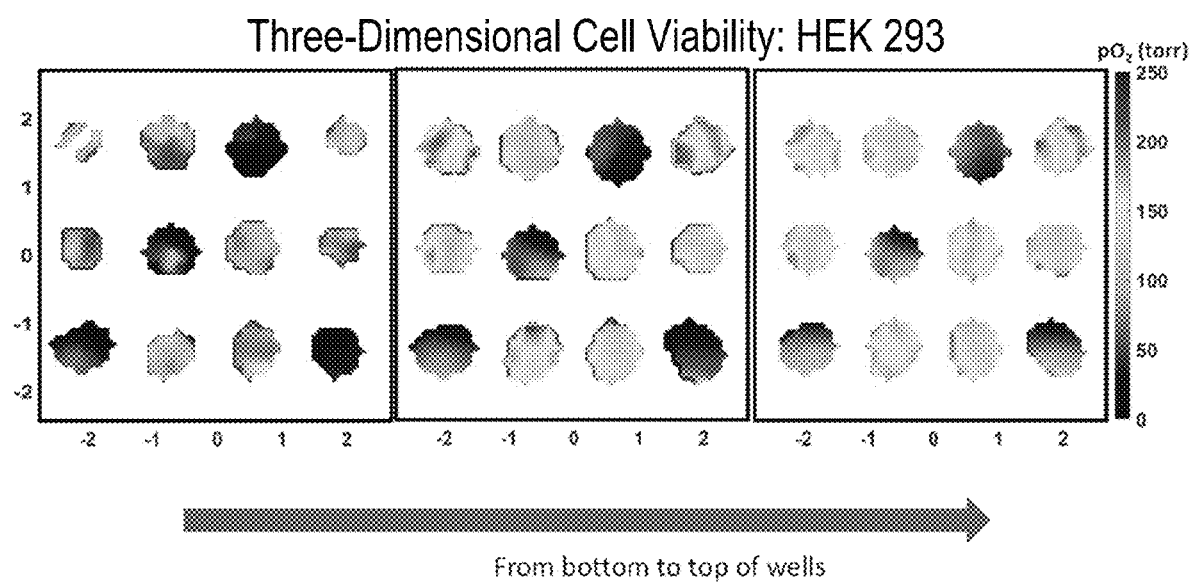
FIG. 23B shows three-dimensional cell viability of HEK293 cells at different depths within the wells.

FIG. 23A shows the cell density placement for the cell viability assessment of FIG. 23B. FIG. 23B shows three-dimensional cell viability of HEK293 cells at different depths within the wells.

From the results of Examples 1-10, it was that three-dimensional oxygen imaging provides assessment of viable cells nondestructively. The cells can be used for further processing after viability test. The method can be extended to any cell+scaffold construct providing unfiltered peek into viable cells for tissue engineering medical products. Cell viability using oxygen imaging maybe a better predictor of outcome of cell therapy and TEMPs than currently used methods. EPROI allows cell viability assessment in tissues of arbitrary size and shape, that could be a useful predictor of success for tissue engineered medical products.

EXEMPLARY EMBODIMENTS

Embodiment 1: A method for non-destructively assessing in situ cell viability, the method comprising: placing a sample of cells, tissue, or an organ into an oxygen imaging system; circulating a humidified gas mixture around the sample; circulating conditioned air through the oxygen imaging system to maintain a temperature around the sample; and acquiring a three-dimensional oxygen map of the cells, tissue, or organ, wherein the oxygen map provides a quantitative measure of cell viability and functionality.

Embodiment 2: The method of embodiment 1, wherein the tissue or the organ is artificial.

Embodiment 3: The method of embodiment 1, wherein the tissue or the organ is natural.

Embodiment 4: The method of embodiment 1, wherein the oxygen imaging system is an electron paramagnetic resonance oxygen imaging system.

Embodiment 5: The method of embodiment 1, wherein at least 90% of cells alive at the beginning of the assessment survive the in situ cell viability assessment.

Embodiment 6: The method of embodiment 1, wherein the oxygen map is a $pO_2$ map that represents viable cells.

Embodiment 7: The method of embodiment 6, wherein $pO_2$ values in the $pO_2$ map are higher for cells that are not viable than cells that are viable.

Embodiment 8: The method of embodiment 7, further comprising characterizing different cell types in the sample.

Embodiment 9: The method of embodiment 8, wherein the different cell types have different equilibrium $pO_2$ values for a particular cell density.

Embodiment 10: The method of embodiment 1, wherein the oxygen map includes a color representation of cell viability.

Embodiment 11: The method of embodiment 1, further comprising obtaining a signal amplitude map.

Embodiment 12: The method of embodiment 1, wherein the sample comprises a cell and scaffold system, wherein the scaffold comprises a biocompatible material.

Embodiment 13: The method of embodiment 12, wherein for each cell type, the cell and scaffold system has an equilibrium $pO_2$ for a certain cell density.

Embodiment 14: The method of embodiment 13, further comprising characterizing the cell density and assessing the cell viability without destroying the cell and scaffold system.

Embodiment 15: A method for non-destructively assessing in situ cell viability, the method comprising: placing a multi-well apparatus comprising a plurality of wells into an oxygen imaging system, wherein one or more wells contain a sample of cells, tissue, and/or a three-dimensional scaffold; circulating a humidified gas mixture through each well via a cover of the multi-well apparatus; circulating conditioned air through the oxygen imaging system to maintain a temperature within the multi-well apparatus; and acquiring a three-dimensional oxygen map of the sample in the one or more wells, wherein the oxygen map provides a quantitative measure of cell viability and functionality.

Embodiment 16: The method of embodiment 15, wherein the oxygen imaging system is an electron paramagnetic resonance oxygen imaging system.

Embodiment 17: The method of embodiment 15, wherein at least 90% of cells alive at the beginning of the assessment survive the in situ cell viability assessment.

Embodiment 18: The method of embodiment 15, wherein the oxygen map is a $pO_2$ map that represents viable cells.

Embodiment 19: The method of embodiment 18, wherein $pO_2$ values in the $pO_2$ map are higher for cells that are not viable than cells that are viable.

Embodiment 20: The method of embodiment 19, further comprising characterizing different cell types in the one or more wells.

Embodiment 21: The method of embodiment 20, wherein different cell types have different equilibrium $pO_2$ values for a particular cell density.

Embodiment 22: The method of embodiment 15, wherein the oxygen map includes a color representation of cell viability.

Embodiment 23: The method of embodiment 15, further comprising obtaining a signal amplitude map.

Embodiment 24: The method of embodiment 15, wherein the sample comprises a cell and scaffold system, wherein the scaffold comprises a biocompatible material.

Embodiment 25: The method of embodiment 24, wherein for each cell type, the cell and scaffold system has an equilibrium $pO_2$ for a certain cell density.

Embodiment 26: The method of embodiment 25, further comprising characterizing the cell density and assessing the cell viability without destroying the cell and scaffold system.

Embodiment 27: The method of embodiment 15, wherein the oxygen imaging system comprises a resonator comprising a body and an intake connector, the resonator body configured to circulate the conditioned air around the multi-well apparatus within the resonator body.

Embodiment 28: The method of embodiment 27, further comprising mixing two air flows in a mixing area of a heating interface to produce the conditioned air, wherein the heating interface is configured to connect to the resonator body via the intake connector.

Embodiment 29: The method of embodiment 15, wherein the cover seals the plurality of wells.

Embodiment 30: The method of embodiment 15, wherein the apparatus is a closed system.

Embodiment 31: The method of embodiment 15, wherein the humidified gas mixture comprises 95% air and 5% $CO_2$.

Embodiment 32: The method of embodiment 15, wherein the humidified gas mixture has a relative humidity of 70%-100%.

Embodiment 33: The method of embodiment 15, further comprising: receiving the humidified gas mixture in an inlet in the cover; and exhausting the humidified gas mixture through an outlet in the cover; wherein a plurality of channels connect the inlet, the plurality of wells, and the outlet.

Embodiment 34: The method of embodiment 33, wherein the plurality of channels comprises at least one gas inlet channel and at least one gas outlet channel.

Embodiment 35: The method of embodiment 34, wherein each well is fluidly connected to a gas inlet channel and a gas outlet channel.

Embodiment 36: The method of embodiment 35, wherein the cover comprises a plurality of manifolds configured to fluidly connect each well to a gas inlet channel and a gas outlet channel, wherein the number of wells matches the number of manifolds.

Embodiment 37: The method of embodiment 36, wherein each manifold comprises a groove configured to receive an O-ring to seal the manifold to the well and a gas exchange protrusion comprising a well gas inlet fluidly connected to the gas inlet channel and a well gas outlet fluidly connected to the gas outlet channel.

Embodiment 38: The method of embodiment 37, wherein the gas exchange protrusion extends into the well.

Embodiment 39: The method of embodiment 38, wherein the well gas inlet extends further into the well than the well gas outlet.

Embodiment 40: The method of embodiment 15, wherein the conditioned air is maintained at a temperature of 37±1° C.

Embodiment 41: A system for non-destructively assessing in situ cell viability, the system comprising: a resonator for electron paramagnetic resonance oxygen imaging, the resonator comprising a body and an intake connector, the resonator body configured to circulate conditioned air around a multi-well apparatus within the resonator body; and the multi-well apparatus comprising a plurality of wells and a cover configured to seal the plurality of wells, wherein the plurality of wells are configured to hold a sample of cells, tissue, and/or a three-dimensional scaffold, and wherein the cover is configured to circulate a humidified gas mixture through each well.

Embodiment 42: The system of embodiment 41, wherein the multi-well apparatus is a closed system.

Embodiment 43: The system of embodiment 41, wherein the humidified gas mixture comprises 95% air and 5% $CO_2$.

Embodiment 44: The system of embodiment 41, wherein the humidified gas mixture has a relative humidity of 70%-100%.

Embodiment 45: The system of embodiment 41, further comprising a humidity sensor.

Embodiment 46: The system of embodiment 41, wherein the cover comprises: an inlet for receiving the humidified gas mixture; an outlet for exhausting the humidified gas mixture; and a plurality of channels connecting the inlet, the plurality of wells, and the outlet.

Embodiment 47: The system of embodiment 46, wherein the plurality of channels comprises at least one gas inlet channel and at least one gas outlet channel.

Embodiment 48: The system of embodiment 47, wherein each well is fluidly connected to a gas inlet channel and a gas outlet channel.

Embodiment 49: The system of embodiment 47, wherein the cover comprises a plurality of manifolds configured to fluidly connect each well to a gas inlet channel and a gas outlet channel, wherein the number of wells matches the number of manifolds.

Embodiment 50: The system of embodiment 49, wherein each manifold comprises a groove configured to receive an O-ring to seal the manifold to the well and a gas exchange protrusion comprising a well gas inlet fluidly connected to the gas inlet channel and a well gas outlet fluidly connected to the gas outlet channel.

Embodiment 51: The system of embodiment 50, wherein the gas exchange protrusion extends into the well.

Embodiment 52: The system of embodiment 51, wherein the well gas inlet extends further into the well than the well gas outlet.

Embodiment 53: The system of embodiment 47, wherein the multi-well apparatus comprises three rows of wells and the cover comprises three gas inlet channels and three gas outlet channels.

Embodiment 54: The system of embodiment 53, further comprising a heating interface configured to connect to the resonator body via the intake connector, the heating interface comprising a mixing area configured to receive two air flows at different temperatures, mix the two air flows to produce the conditioned air, and output the conditioned air.

Embodiment 55: The system of embodiment 54, wherein the mixing area comprises a plurality of mixing fins.

Embodiment 56: The system of embodiment 41, wherein the conditioned air is maintained at a temperature of 37±1° C.

Embodiment 57: The system of embodiment 41, further comprising a temperature sensor.

Embodiment 58: The system of embodiment 41, further comprising a tray configured to support the plurality of wells.

Embodiment 59: The system of embodiment 58, wherein the tray further comprises at least one standoff configured to releasably connect with the cover.

Embodiment 60: The system of embodiment 59, wherein the cover comprises at least one cutout on a lower surface, the at least one cutout configured to receive the at least one standoff.

Embodiment 61: The system of embodiment 59, wherein the at least one standoff is integrated with the tray.

Embodiment 62: The system of embodiment 59, wherein the at least one standoff comprises threads and is configured to be screwed into the tray and/or the cover.

Embodiment 63: The system of embodiment 41, wherein the resonator is square.

Embodiment 64: The system of embodiment 63, wherein the resonator further comprises a square resonator block and a resonator shield.

Embodiment 65: The system of embodiment 63, wherein the resonator further comprises air directors, front and back covers, and/or a heater interface bracket.

Embodiment 66: The system of embodiment 63, wherein the resonator further comprises a match box mount and a match box configured to hold the multi-well apparatus.

Embodiment 67: The system of embodiment 66, wherein the match box is made of copper.

Embodiment 68: The system of embodiment 66, wherein the match box mount comprises: a slot cut-out for installation of the match box; a tuning wheel; a lip configured to provide mechanical support for the tuning wheel; and a hole for the tuning wheel.

VARIOUS NOTES

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system for non-destructively assessing cell viability, the system comprising:
   a resonator configured for electron paramagnetic resonance oxygen imaging, the resonator having a body configured to circulate conditioned air received at an intake connector around a multi-well apparatus within the resonator body; and
   the multi-well apparatus including a plurality of wells and a cover configured to seal the plurality of wells from an ambient atmosphere;
   wherein the plurality of wells are configured to hold a sample and wherein the cover is configured to circulate a humidified gas mixture through each well.

2. The system of claim 1 wherein the cover is configured to circulate the gas mixture individually through each well.

3. The system of claim 1 wherein the cover includes a gas mixture inlet port.

4. The system of claim 1 wherein the cover includes a gas mixture outlet port.

5. The system of claim 1 further comprising a humidity sensor coupled to the multi-well apparatus at an inlet.

6. The system of claim 1 further comprising a humidity sensor coupled to the multi-well apparatus at an outlet.

7. The system of claim 1 wherein the cover includes a plurality of channels, wherein at least one channel of the plurality of channels is fluidly coupled to an inlet port, to the plurality of wells, and to an outlet port.

8. The system of claim 1 further including a manifold coupled to a well, wherein the manifold includes a protrusion having a gas inlet port and a gas outlet port.

9. The system of claim 8 wherein the gas inlet port has an inlet length and the gas outlet port has an outlet length and wherein the inlet length and the outlet length differ.

10. The system of claim 1 further including a heating interface coupled to the resonator.

11. The system of claim 10 wherein the heating interface includes a mixing region configured to receive a first air flow at a first temperature and to receive a second air flow at a second temperature, wherein the first air temperature differs from the second air temperature.

12. The system of claim 1 further including a heater configured to heat the conditioned air.

13. The system of claim 12 wherein the heater is configured to heat the conditioned air to 37° C.

14. The system of claim 1 wherein the resonator includes an inner volume of rectangular shape.

15. The system of claim 1 wherein the resonator includes an inner volume configured to receive the multi-well apparatus.

16. The system of claim 1 wherein the resonator includes a copper shield.

* * * * *